United States Patent
Hotta et al.

(10) Patent No.: US 9,839,377 B2
(45) Date of Patent: Dec. 12, 2017

(54) SUBJECT PERSON SPECIFYING APPARATUS AND SUBJECT PERSON SPECIFYING METHOD

(71) Applicant: FUJITSU LIMITED, Kawasaki-shi, Kanagawa (JP)

(72) Inventors: Shinji Hotta, Kawasaki (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 77 days.

(21) Appl. No.: 14/840,800

(22) Filed: Aug. 31, 2015

(65) Prior Publication Data
US 2016/0058328 A1 Mar. 3, 2016

(30) Foreign Application Priority Data
Sep. 3, 2014 (JP) ................. 2014-179040

(51) Int. Cl.
*A61B 5/02* (2006.01)
*A61B 5/117* (2016.01)
*A61B 5/024* (2006.01)
*A61B 5/00* (2006.01)

(52) U.S. Cl.
CPC .............. *A61B 5/117* (2013.01); *A61B 5/024* (2013.01); *A61B 5/4848* (2013.01); *A61B 5/4866* (2013.01); *A61B 5/7264* (2013.01); *A61B 5/7278* (2013.01); *A61B 2560/0475* (2013.01)

(58) Field of Classification Search
CPC ..... A61B 5/117; A61B 5/7264; A61B 5/4848; A61B 5/4866; A61B 5/7278; A61B 5/024; A61B 2560/0475
See application file for complete search history.

(56) References Cited

U.S. PATENT DOCUMENTS

2014/0266696 A1* 9/2014 Addison ................ A61B 5/117
340/539.12

FOREIGN PATENT DOCUMENTS

| EP | 1092453 A2 | 4/2001 |
|---|---|---|
| JP | 06-142065 | 5/1994 |
| JP | 11-197136 | 7/1997 |
| JP | 2001-202524 | 7/2001 |
| JP | 2004-310207 | 11/2004 |

(Continued)

OTHER PUBLICATIONS

EESR—The Extended European Search Report dated Jan. 26, 2016 issued in the corresponding European application No. 15183037.9.

(Continued)

*Primary Examiner* — Rex R Holmes
(74) *Attorney, Agent, or Firm* — Fujitsu Patent Center

(57) ABSTRACT

A subject person specifying apparatus includes a processor, and a memory storing a program causing the processor to perform acquiring characteristic quantities of variations of heart rate related to a meal of a subject person from heart rate data of the subject person as a target of an individual specifying process, calculating a distribution range of history values of the characteristic quantities associated with a plurality of candidates, and extracting the candidate corresponding to the subject person from within the plurality of candidates, based on a relation between the characteristic quantities acquired from the subject person and the distribution range of the history values of the characteristic quantities.

18 Claims, 42 Drawing Sheets

(56) References Cited

FOREIGN PATENT DOCUMENTS

| JP | 2006-218033 | 8/2006 |
| JP | 2007-213196 | 8/2007 |
| WO | 2004/096045 | 11/2004 |

OTHER PUBLICATIONS

Kasahara et al., "A Study on the Personal Authentication Using Sensor Data of Mobile Terminal", IEICE, Proceedings of Biometrics Workshop, Aug. 27-28, 2012, pp. 45-50 (6 pages), with English Abstract.

* cited by examiner

FIG. 15

| HEART RATE CHARACTERISTIC QUANTITY | |
|---|---|
| AREA SIZE RATIO | RATIO OF FIRST AREA SIZE TO SECOND AREA SIZE |
| AMPLITUDE | FIRST PEAK AMPLITUDE<br>SECOND PEAK AMPLITUDE |
| RESPONSE SPEED | FIRST PEAK RISING RESPONSE SPEED<br>FIRST PEAK RESTORATION RESPONSE SPEED<br>SECOND PEAK RISING RESPONSE SPEED<br>SECOND PEAK RESTORATION RESPONSE SPEED |
| RESPONSE TIME | FIRST PEAK RISING RESPONSE TIME<br>FIRST PEAK RESTORATION RESPONSE TIME<br>SECOND PEAK RISING RESPONSE TIME<br>SECOND PEAK RESTORATION RESPONSE TIME |

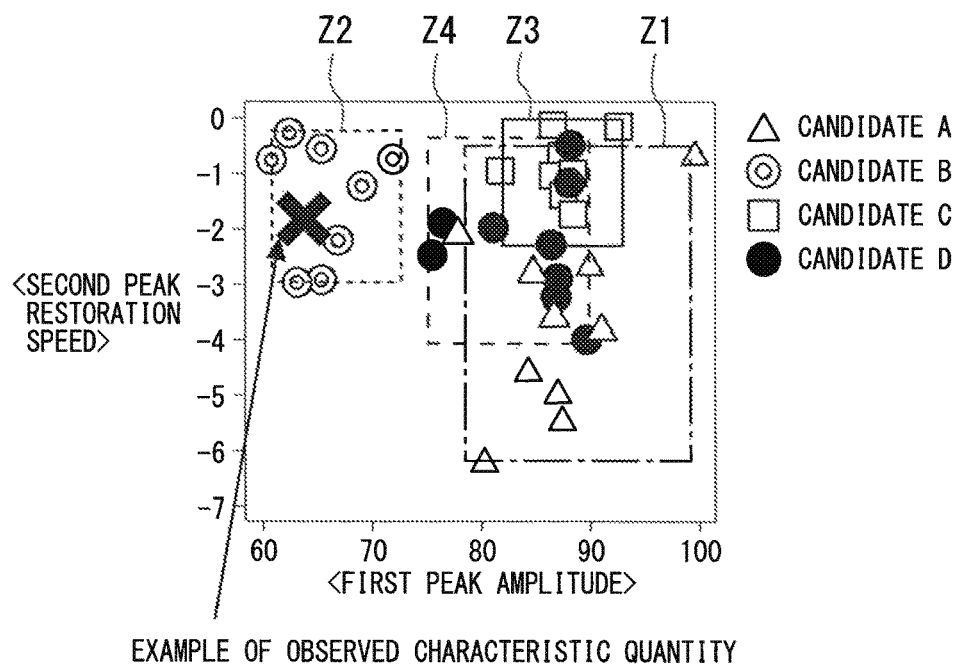

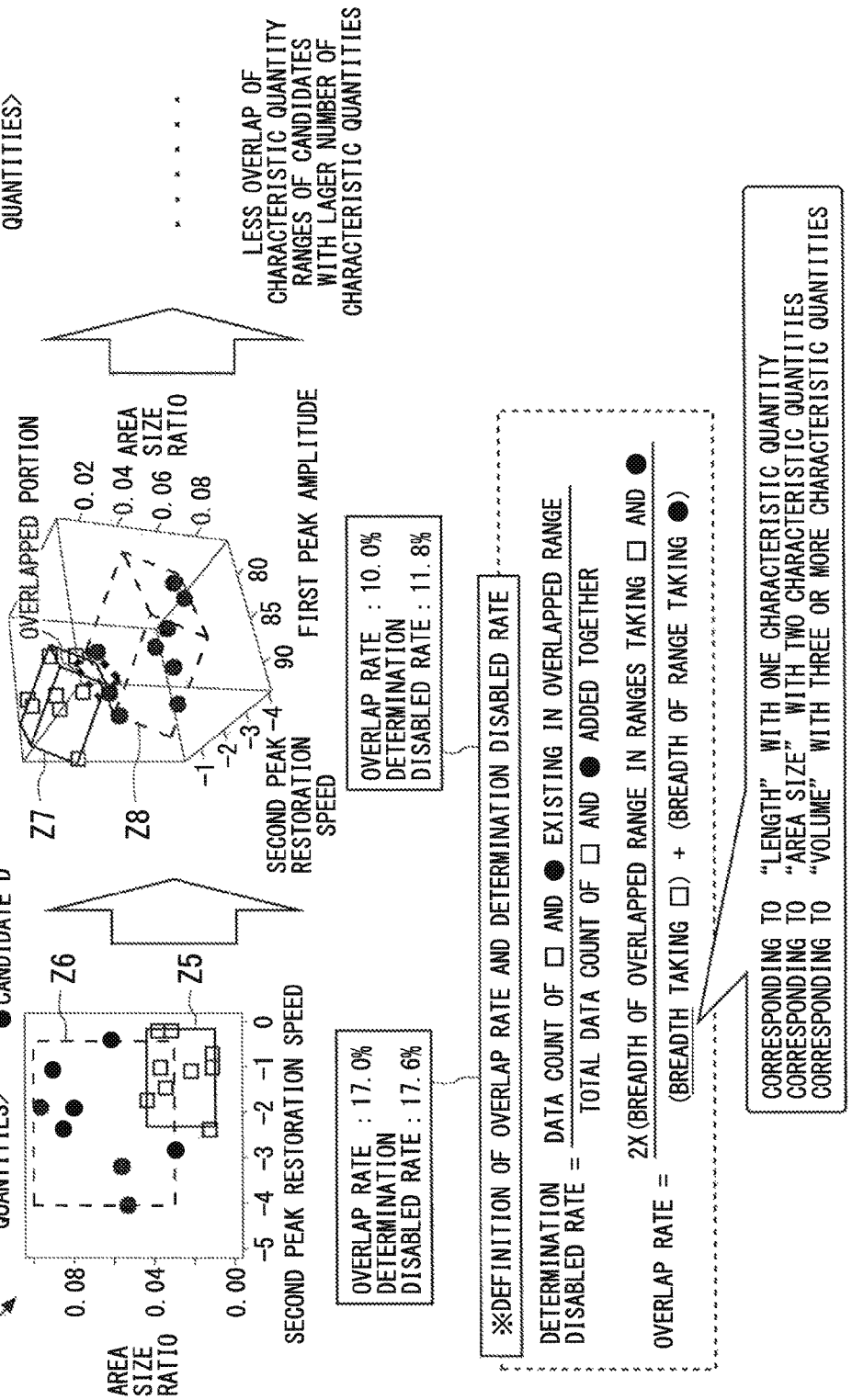

FIG. 26

< TABLE: MEAL CHARACTERISTIC QUANTITY TABLE >

[EQUIPMENT NUMBER: B]

| CHARACTERISTIC QUANTITY | CALCULATION RESULT |
|---|---|
| AREA SIZE RATIO | 0.82 |
| FIRST PEAK AMPLITUDE | 85.2 |
| FIRST PEAK RISING RESPONSE TIME | 7 |
| FIRST PEAK RISING RESPONSE SPEED | 75.3 |
| FIRST PEAK RESTORATION RESPONSE TIME | 45.7 |
| FIRST PEAK RESTORATION RESPONSE SPEED | - 34.4 |
| SECOND PEAK AMPLITUDE | 83.7 |
| SECOND PEAK RISING RESPONSE TIME | 27 |
| SECOND PEAK RISING RESPONSE SPEED | 17.1 |
| SECOND PEAK RESTORATION RESPONSE TIME | 231.5 |
| SECOND PEAK RESTORATION RESPONSE SPEED | - 6.4 |

<(1) CALCULATION FLOW OF AREA SIZE CHARACTERISTIC QUANTITY>

<(2) CALCULATION FLOW OF AMPLITUDE CHARACTERISTIC QUANTITY>

<(4) CALCULATION FLOW OF TIME CHARACTERISTIC QUANTITY>

MAXIMUM HEARTBEAT TIME IN POSTPRANDIAL PERIOD

| TIME | 09-02 12:52:00 | ... | 09-02 13:19:00 | ... | 09-02 16:59:00 |
|---|---|---|---|---|---|
| HEART RATE | 65.3 | ... | 83.7 | ... | 75.3 |
| MEAL PERIOD | 0 | ... | 0 | ... | 0 |

⇨ CALCULATION OF AMPLITUDE AND RISING RESPONSE TIME ⇨

| CHARACTERISTIC QUANTITY | CALCULATION RESULT |
|---|---|
| AMPLITUDE | 83.7 |
| RISING RESPONSE TIME (MIN) | 27 |

| | CALCULATION RESULT |
|---|---|
| MAXIMUM HEART RATE (bpm) | 83.7 |
| BASELINE (bpm) | 59.0 |
| HEART RATE DIFFERENCE (bpm) | 24.7 |
| RESTORATION RESPONSE SPEED (bpm/hour) | -6.4 |
| RESTORATION RESPONSE TIME (MIN) | 231.5 |

FIG. 61

<TABLE: UNIQUE RANGE LIST OF CANDIDATES>

"a" IN [a, b] IN TABLE CORRESPONDS TO MINIMUM VALUE, WHILE "b" CORRESPONDS TO MAXIMUM VALUE

| CHARACTERISTIC QUANTITY | CANDIDATE A | CANDIDATE B | ... |
|---|---|---|---|
| AREA SIZE RATIO | [0.62, 1.00] | [1.32, 1.60] | ... |
| FIRST PEAK AMPLITUDE | [71.3, 92.1] | [62.1, 70.0] | ... |
| FIRST PEAK RISING RESPONSE TIME | [4, 9.5] | [3, 9.5] | ... |
| FIRST PEAK RISING RESPONSE SPEED | [58.9, 86.3] | [50.3, 90.3] | ... |
| FIRST PEAK RESTORATION RESPONSE TIME | [31, 50] | [32, 38] | ... |
| FIRST PEAK RESTORATION RESPONSE SPEED | [-43.7, -34.0] | [-43.2, -29.5] | ... |
| SECOND PEAK AMPLITUDE | [83.7, 91.1] | [57.1, 65.8] | ... |
| SECOND PEAK RISING RESPONSE TIME | [27, 40] | [36, 50] | ... |
| SECOND PEAK RISING RESPONSE SPEED | [11.2, 17.1] | [2.3, 5.6] | ... |
| SECOND PEAK RESTORATION RESPONSE TIME | [156.5, 231.5] | [128.5, 421] | ... |
| SECOND PEAK RESTORATION RESPONSE SPEED | [-10.7, -3.4] | [-3.7, -0.7] | ... |

SET LOGICAL PRODUCT OF ALL OF MAXIMUM AND MINIMUM RANGES
$(F^{(j)} = [\min(f^{(j)}_1), \max(f^{(j)}_1)] \times \cdots \times [\min(f^{(j)}_{11}), \max(f^{(j)}_{11})])$
AS UNIQUE RANGE $F^{(j)}$ OF CANDIDATE "j"

SUBJECT PERSON SPECIFYING APPARATUS AND SUBJECT PERSON SPECIFYING METHOD

CROSS-REFERENCE TO RELATED APPLICATION

This application is based upon and claims the benefit of priority of the prior Japanese Patent Application No. 2014-179040, filed on Sep. 3, 2014, the entire contents of which are incorporated herein by reference.

FIELD

The embodiments discussed herein are related to a subject person specifying apparatus and a subject person specifying method.

BACKGROUND

With an increase in number of aged persons, a number of patients commuting to a variety of medical institutions tends to rise. On the other hand, such a situation is presumed that medical workers engaging in the medical institutions will be deficient in number for the increased number of patients. It is considered for coping with the deficiency in number of medical workers to reduce a load on the medical worker by acquiring biological information instanced by a heart rate and other equivalent data of the patient as a medical treatment target person and continuously grasping a health state of the individual patient. The health state at a resting time can be grasped by continuously acquiring the biological information. Upon detecting an abnormal value in the biological information acquired from the patient on a basis of the biological information at the resting time, the medical worker is notified of this abnormal value and is thereby enable to promptly perform a treatment against the abnormal value.

A use of a wearable sensor, which is worn to an arm region, a chest region and other equivalent regions of the patient and is capable of acquiring the biological information exemplified by vital information (a body temperature, a heartbeat, breathing, a blood pressure and other equivalent vital data), is assumed as a method of continuously acquiring the biological information of the patient. The wearable sensor is capable of acquiring the biological information exemplified by the vital information and other equivalent vital data through a variety of sensors in contact with patient's body. However, the wearable sensor based method of continuously acquiring the biological information of the patient might cause the patients to wear incorrect wearable sensors as the case may be. If the wearable sensor is incorrectly worn or another equivalent event happens, it is desirable to confirm that the wearer of the wearable sensor is a true wearer from the biological information acquired via the wearable sensor.

Proposed as a method of specifying the individual from the acquired biological information are a method of using short-time biological features instanced by electrocardiographic waveforms and other equivalent features, and a method of using long-time biological features instanced by a resting heart rate, a maximum blood pressure, a minimum blood pressure and other equivalent features. Proposed further as a method of continuously specifying a user from data acquired from the sensor and other equivalent devices is a method of using a user's behavior pattern instanced by user's motion characteristics of a stride, a posture, a hand waving manner and other equivalent motions, and a positional history, which are detected by an acceleration sensor mounted on a portable equipment and other equivalent equipments.

Note that the following patent documents are given as prior art documents containing descriptions of technologies related to a technology to be described in the present specification.

Non-Patent Document

[Non-Patent document 1] "A Study on the Personal Authentication Using Sensor Data of Mobile Terminal", Hiroki Kasahara and five others, [online], August in 2012, the Institute of Electronics, Information and Communication Engineers, the first study meeting for biometrics, [searched on May 30, 2014, Internet <URL: https://www.ieice.org/~biox/limited/2012/001-kenkyukai/pdf/Bio X2012-09.pdf>

Patent Document

[Patent document 1] International Publication Pamphlet No. WO 2004/096045
[Patent document 2] Japanese Laid-Open Patent Publication No. 2004-310207
[Patent document 3] Japanese Laid-Open Patent Publication No. 2007-213196
[Patent document 4] Japanese Laid-Open Patent Publication No. H11-197136
[Patent document 5] Japanese Laid-Open Patent Publication No. H6-142065

SUMMARY

An aspect of the embodiments is exemplified by a configuration of a subject person specifying apparatus that follows. To be specific, the subject person specifying apparatus includes a processor, and a memory storing a program causing the processor to perform acquiring characteristic quantities of variations of heart rate related to a meal of a subject person from heart rate data of the subject person as a target of an individual specifying process, calculating a distribution range of history values of the characteristic quantities associated with a plurality of candidates, and extracting the candidate corresponding to the subject person from within the plurality of candidates, based on a relation between the characteristic quantities acquired from the subject person and the distribution range of the history values of the characteristic quantities.

The object and advantages of the invention will be realized and attained by means of the elements and combinations particularly pointed out in the claims. It is to be understood that both the foregoing general description and the following detailed description are exemplary and explanatory and are not restrictive of the invention.

BRIEF DESCRIPTION OF THE DRAWINGS

FIG. 15 is an explanatory diagram of a table to store the characteristic quantities of the heartbeats pertaining to the meal;

FIG. 16 and FIG. 17 are explanatory diagrams of narrowing down the subject person by use of the characteristic quantities of the heartbeats pertaining to the meal;

FIG. 18 is an explanatory diagram of narrowing down the subject person by use of the characteristic quantities of the heartbeats pertaining to the meal;

FIG. 26 is an explanatory diagram of a table to store the characteristic quantities of the heartbeats pertaining to the meal;

FIG. 61 is a diagram illustrating one example of a unique range list generated based on experimental values;

DESCRIPTION OF EMBODIMENTS

Figure 1:
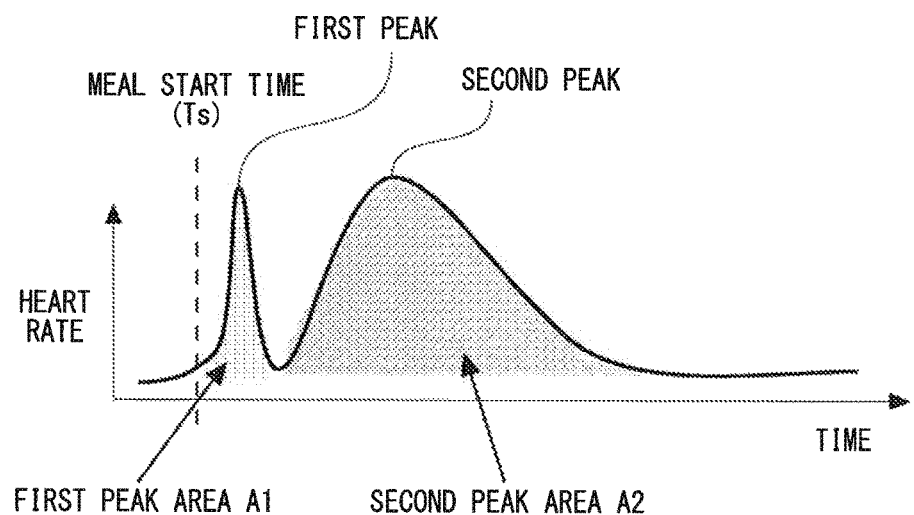
FIG. 1 is an explanatory diagram of characteristics of heartbeats pertaining to a meal.

The wearer of the wearable sensor is specified by the method using the biological features, in which case the short-time biological features instanced by the electrocardiographic waveforms tend to be affected by a deviation of wearing position and a contact state of the sensor. Consequently, erroneous authentication might occur, e.g., when the sensor is re-worn or performing an exercise instanced by going up and down stairs, and other exercises.

Moreover, the deviation of the wearing position and other equivalent states are not of any problem when using the vital information instanced by the resting heart rate and other equivalent information, and, however, the wearer is not specified as a true wearer in every aspect because of there being a situation in which another person different from the wearer has similar vital information. As a result, when the wearable sensor is mistakenly worn or other equivalent states occur, the erroneous authentication of deeming the wearer as the true wearer might be passed.

Further, when specifying the true wearer of the wearable sensor from a characteristic of action instanced by walking, the wearer can be impersonated as the true wearer by simulating the walking characteristic. When specifying the true wearer of the wearable sensor from the behavior pattern instanced by the positional history, and when there are less of variations of the behavior pattern (behaviors within the medical institution instanced by a hospital and other equivalent institutions), an individual difference is hard to occur as a tendency. Consequently, the wearer is not specified as the true wearer in every aspect as the case may be.

A subject person specifying apparatus according to one embodiment will hereinafter be described with reference to the drawings. A configuration of the following embodiment is an exemplification, and the subject person specifying apparatus is not limited to the configuration of the embodiment.

The subject person specifying apparatus will hereinafter be described based on the drawings in FIGS. 1 through 70.

EXAMPLE 1

An inventor of the present application found that a characteristic of heartbeats associated with meals tend to fall within a fixed range irrespective of an amount of meals, digestive easiness of foods ingested at meals and other equivalent properties, and that the characteristic of heartbeats associated with the meals has differences among individuals. The inventor of the present application further found that a comparison between the characteristics of heartbeats associated with meals, serves to specify the individual without using items of information instanced by a physical constitution (height, weight), an age, a distinction of sex, a race and other equivalent information and also other items of information instanced by 24-hour circadian rhythm data on a month/year basis and other equivalent data of the subject persons, the characteristics being acquired from a plurality of subject persons.

The characteristics of heartbeats associated with meals will hereinafter be described as biological features according to the present embodiment with reference to the drawings illustrated in FIGS. 1-4. FIG. 1 illustrates an explanatory diagram of a variation of heartbeats that occurs after a start of meals. FIG. 1 represents a graph of the variation of heartbeats after the start of meals, in which an axis of ordinates indicates the heartbeats per unit time, while an axis of abscissa indicates elapse time (a period of time) since just before the start of meals.

As illustrated in FIG. 1, with the subject person's action to take a meal, there exist two peaks at which the heartbeats rises (increases) and falls (decreases) in turn with the time elapse in the variation of heartbeats after the start of meals. Note that an anterior peak of heartbeats with the time elapse since a meal start time (Ts) is referred to as a "first peak", while a posterior peak of heartbeats is referred to as a "second peak". A predetermined area including the "first peak" is termed a "first peak area A1", while a predetermined area including the "second peak" is termed a "second peak area A2. Note that the predetermined areas will be described later on in conjunction with FIG. 7.

In the two peaks of heartbeats that occur after the start of meal as illustrated in FIG. 1, the first peak is the rise of heartbeats associated with the action to take the meal and is presumed as a rise of heartbeats due to a peristaltic movement of, e.g., an esophageal. The second peak is presumed as a rise of heartbeats due to a digestive activity within a digestive organ (gastrointestinal and other equivalent organs) with respect to an acquisition (foods and other equivalent elements) acquired by the action to take the meal. Therefore, the action to take the meal, the peristaltic movement and the digestive activity tend to have individual differences about the following points (a)-(c). The following discussion will give exemplifications based on this presumption in order to explain the variation of heartbeats and the individual differences.

(a) Digestive Speed

Figure 2:
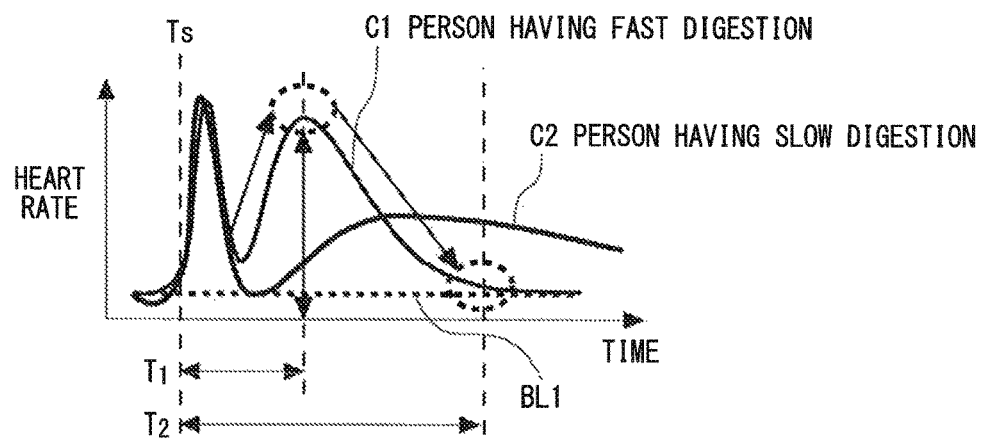
FIG. 2 is an explanatory diagram of a heart rate variation pertaining to a digestive activity and other equivalent activities.

FIG. 2 illustrates an explanatory diagram of the variation associated with the digestive activity and other equivalent activities. Similarly to the explanatory diagram illustrated in FIG. 1, the explanatory diagram of FIG. 2 represents a graph of the variation of heartbeats after the start of meal, in which the axis of ordinates indicates the heartbeats per unit time, while the axis of abscissa indicates the elapse time (the period of time) since just before the start of meal. Note that the same is applied to explanatory diagrams in FIGS. 3 and 4.

In the explanatory diagram illustrated in FIG. 2, a curve C1 represents a variation of heartbeats of a subject person having a high digestive speed, while a curve C2 represents a variation of heartbeats of a subject person having a low digestive speed. A broken line BL1 parallel to the axis of abscissa represents a baseline of the heartbeats. Herein, a heartbeat value serving as the baseline may be exemplified by an average value of the heartbeats for a predetermined period of time instanced by 10 minutes, one hour and other equivalent time values before the start of meal. The heartbeat value serving as the baseline may be further exemplified by the heartbeats upon the start of meal of the subject person and the heartbeats being minimized between the first peak and the second peak. A method of setting the baseline of the heartbeats may be sufficient if common between or among the plurality of subject persons.

In comparison of the variation of heartbeats between the curve C1 and the curve C2, the curve C1 tends to be relatively short compared with the curve C2 in period till reaching the second peak, and also to be relatively shorter in period till reaching the heartbeat value set as the baseline BL1 after the second peak than the curve C2. In other words, the curve C1 tends to be relatively high (steep gradient) in speed (rising speed) kept rising till reaching the second peak of the heartbeats, and also to be relatively high (steep gradient) in speed (restoration speed) till reaching the baseline BL1 from the second peak.

The curve C1 tends to be relatively large in variation width till reaching the heartbeats of the second peak. Further, the curve C1 tends to be short in period T1 till reaching the heartbeats of the second peak since the meal start time (Ts), and also to be short in period T2 till reaching the baseline BL1 after the second peak since the meal start time (Ts).

Presumption of a reason for occurrence of the tendencies described above lies in that the subject person having a high digestive speed has a large quantity of secretes instanced by digestive juice and other equivalent secretes within the gastrointestinal, and exhibits a steep rise in quantity of blood flow to the gastrointestinal and other equivalent organs and a steep fall thereafter. It therefore follows that the subject person having the high digestive speed consumes a large quantity of energy related to the digestion in a short period of time during the digestive activity as compared with the subject person having a low digestive speed. The subject person having the high digestive speed tends to cause a short-period variation of heartbeats, following the consumption of energy.

(b) Energy Related to Digestion

Figure 3:
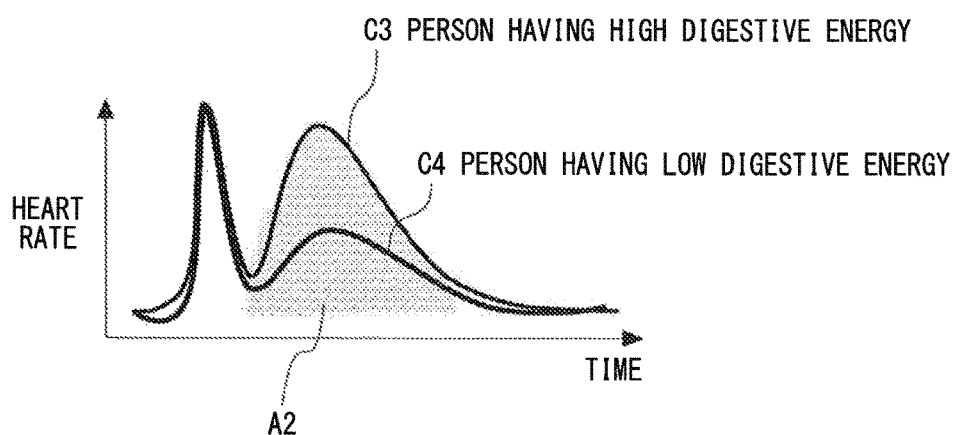
FIG. 3 is an explanatory diagram of the heart rate variation pertaining to the digestive activity and other equivalent activities.

FIG. 3 illustrates an explanatory diagram of the variation of heartbeats associated with the digestive activity and other equivalent activities. In the explanatory diagram illustrated in FIG. 3, a curve C3 represents a variation of heartbeats of a subject person having high energy related to the digestion (digestive energy), while a curve C4 represents a variation of heartbeats of a subject person having low energy related to the digestion.

In comparison of the variation of heartbeats between the curve C3 and the curve C4, the curve C3 tends to be relatively high compared with the curve C4 in heartbeats of the second peak and to be relatively easy to rise in variation of heartbeats. Further, the curve C3 tends to be relatively large in overall area size of the second peak area A2 in relation to the heartbeats, and also tends to be relatively large in maximum variation width till reaching the second peak.

Presumption of a reason for occurrence of the tendencies described above lies in that the subject person having the high energy related to the digestion is large in total amount of digestive juice secreted for the digestion and is also large in quantity of blood flow to the gastrointestinal and other equivalent organs during a digestive activity period throughout. Therefore, the subject person having the high energy related to the digestion is large in total amount of energy consumed during the digestive activity period throughout as compared with a subject person having low energy related to the digestion. The subject person having the high energy related to the digestion tends to be high in total sum of the heartbeats varied during the digestive activity period.

(c) Peristaltic Movement and Activity Load Ratio of Digestive Activity

Figure 4:
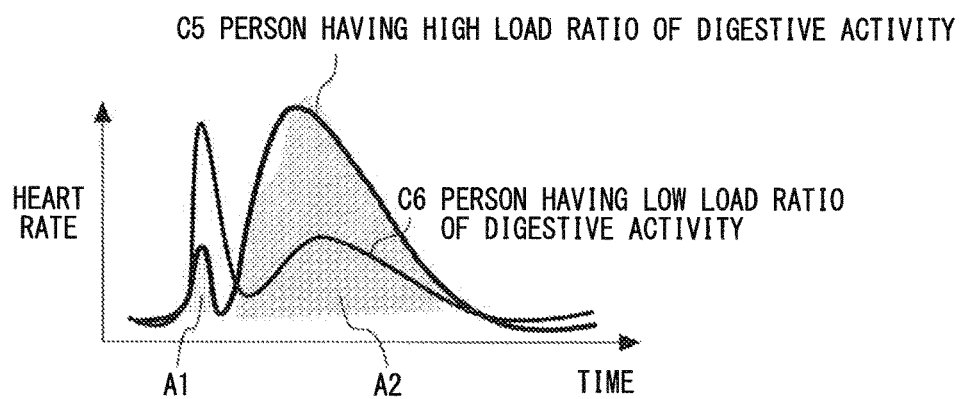
FIG. 4 is an explanatory diagram of the heart rate variation pertaining to the digestive activity and other equivalent activities.

FIG. 4 illustrates an explanatory diagram of the variation of heartbeats associated with the digestive activity and other equivalent activities. In the explanatory diagram illustrated in FIG. 4, a curve C5 represents a variation of heartbeats of a subject person having a high activity load ratio of the digestive activity, while a curve C6 represents a variation of heartbeats of a subject person having a low activity load ratio of the digestive activity. Herein, the activity load ratio represents a ratio of total energy related to the peristaltic movement of the subject person to total energy related to the digestive activity.

In comparison of the variation of heartbeats between the curve C5 and the curve C6, the curve C5 tends to be high compared with the curve C6 in total energy (area size of the second peak area A2) for the digestion but low in total energy (area size of the first peak area A1) for the peristaltic movement. The curve C5 also tends to be relatively high in area ratio of the area size of the second peak area A2 to the area size of the first peak area A1. The subject person having the high activity load ratio of the digestive activity tends to be high in total energy for the digestion but low in total energy for the peristaltic movement. Note that the area sizes of the first peak area A1 and the second peak area A2 will be described with reference to FIG. 7.

As described in (a)-(c), the characteristic tendencies derived from the peristaltic movement and the digestive activity and other equivalent activities of the subject person, appear in the two peaks of the variations of heartbeats that occur after the start of meal. It is therefore feasible to narrow down candidates for specifying the individual from within the plurality of candidates by using characteristic quantities with respect to the two peaks of the variations of heartbeats that occur, e.g., after the start of meal. The individual (correct result) narrowed down from the plurality of candidates will hereinafter be call the subject person.

Figure 5:
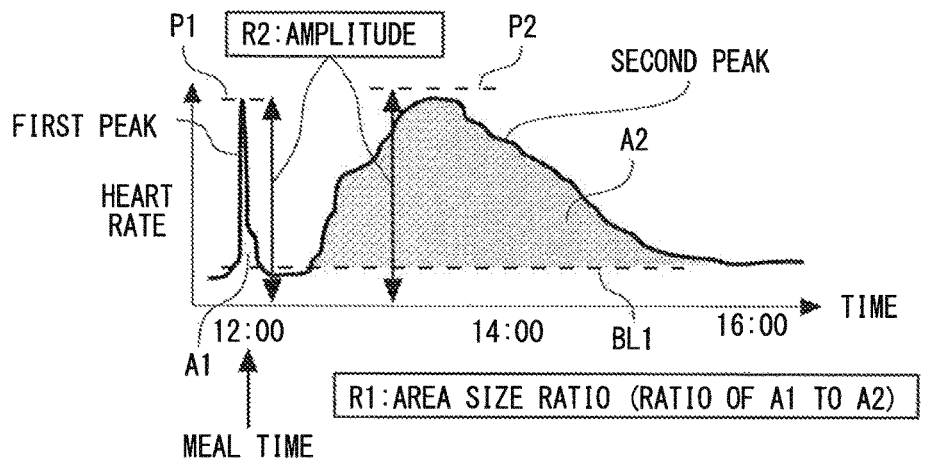
FIG. 5 is an explanatory diagram of characteristic quantities of the heartbeats pertaining to the meal.
Figure 6:
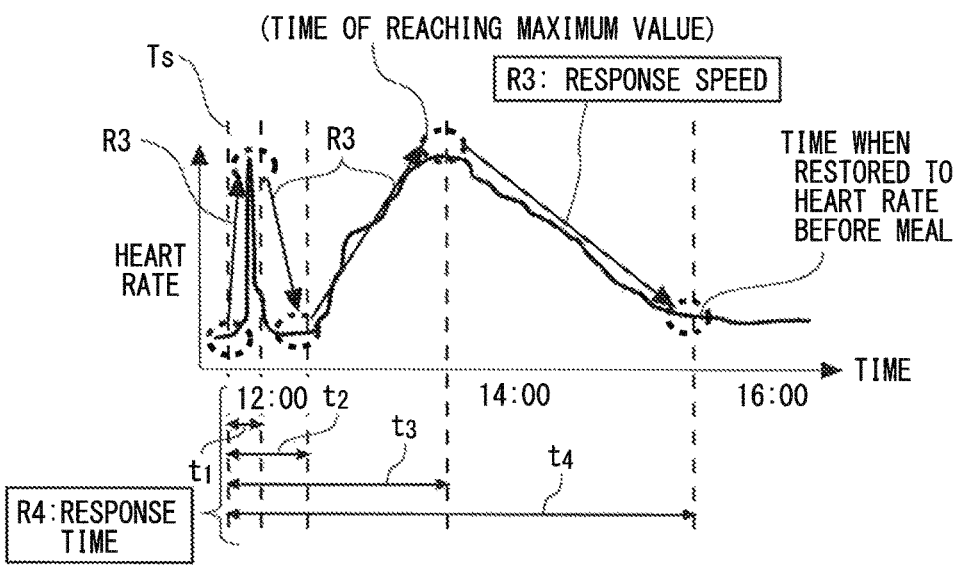
FIG. 6 is an explanatory diagram of the characteristic quantities of the heartbeats pertaining to the meal.

For example, following characteristic quantities R1-R4 can be defined with respect to the two peaks of the variations of heartbeats that occur after the start of meal described in (a)-(c). FIGS. 5 and 6 illustrate explanatory diagrams of the characteristic quantities R1-R4 with respect to the two peaks of the variations of heartbeats that occur after the start of meal as being defined according to the embodiment. Note that FIGS. 5 and 6 illustrate graphs of the variation of heartbeats after the start of meal when having a lunch, in which the axis of ordinates indicates the heartbeats per unit time, while the axis of abscissa indicates the elapse time (the period of time) since just before the start of meal.

FIG. 5 illustrates an explanatory diagram of the characteristic quantities R1, R2 with respect to the two peaks of the variations of heartbeats that occur after the start of meal when having the lunch. As described in (a)-(c), the peristaltic movement and the activity load ratio of the digestive activity differ per subject person, and hence, e.g., as illustrated in FIG. 5, an area size ratio of the first peak area A1 to the second peak area A2 after the start of meal can be set as a characteristic quantity (characteristic quantity R1). Note that the area sizes of the first peak area A1 and the second peak area A2 will be described in FIG. 7.

Every subject person has difference characteristics of the peristaltic movement and the digestive activity, and therefore, e.g., as illustrated in FIG. 5, each of maximum heartbeat values P1, P2 at each of the first peak and the second peak can be set as the characteristic quantity (characteristic quantity R2). Note that the maximum heartbeat value at each of the first peak and the second peak is referred to also as an "amplitude".

FIG. 6 illustrates an explanatory diagram of the characteristic quantities R3, R4 with respect to the two peaks of the variations of heartbeats that occur after the start of meal when having the lunch. As described in (a)-(c), every subject person has different characteristics of the peristaltic movement and the digestive activity, and hence, e.g., as illustrated in FIG. 5, the rising speed of the heartbeats till reaching the maximum heartbeat values P1, P2 at each of the first peak and the second peak can be set as a characteristic quantity (characteristic quantity R3).

Similarly, e.g., as illustrated in FIG. 6, a restoration speed to restore the heartbeats from the maximum heartbeat values P1, P2 at each of the first peak and the second peak can be set as the characteristic quantity (characteristic quantity R3). Note that a characteristic quantity embracing the rising speed and the restoration speed at the first peak and the second peak is referred to also as a "response speed". At the first peak and the second peak, the rising speed is also termed a "rising response speed", and the restoration speed is termed a "restoration response speed". Note that in-depth descriptions of the various response speeds at the first peak and the second peak will be made in FIGS. 9-12.

As illustrated in FIG. 6, the peristaltic movement and the digestive activity at the first peak and the second peak have different characteristics per subject person, and hence, various response times since the meal start time (Ts) can be set as a characteristic quantity (characteristic quantity R4), the various response times at the first peak may include, e.g., an elapse time (t1) till reaching the maximum heartbeat value P1 since the meal start time (Ts) and an elapse time (t2) till a restoration of the heartbeats having reached the maximum heartbeat value P1 since the meal start time (Ts). The various response times at the second peak may include, e.g., an elapse time (t3) till reaching the maximum heartbeat value P2 since the meal start time (Ts) and an elapse time (t4) till the restoration of the heartbeats having reached the maximum heartbeat value P2 since the meal start time (Ts).

Note that a magnitude relation between the various response times since the meal start time (Ts) is given by t1<t2<t3<t4. Herein, at every peak, the elapse time till reaching the maximum heartbeat value since the meal start time (Ts) is referred to also as a "rising response time", and the elapse time till the restoration of the heartbeats having reached the maximum heartbeat value P1 since the meal start time (Ts) is referred to also as a "restoration response time" since the meal start time (Ts). It is to be noted that in-depth descriptions of the various response speeds at the first peak and the second peak will be made in FIGS. 13-14.

According to the embodiment, biological features related to the heartbeats of the plurality of candidates can be narrowed down by detecting the characteristic quantity R1 defined with respect to the first peak area A1 and the second peak area A2, e.g., after the start of meal. Similarly, the biological features related to the heartbeats of the plurality of candidates can be narrowed down by detecting at least one of the characteristic quantities R2-R4 defined with respect to each of the first peak and the second peak after the start of meal. For example, at least one of the characteristic quantities R1-R4 can be used as a parameter for narrowing down to the subject person from within the plurality of candidates. Detection and other equivalent processes of the characteristic quantities R1-R4 will next be described.

[Detection of Characteristic Quantity R1]

Figure 7:
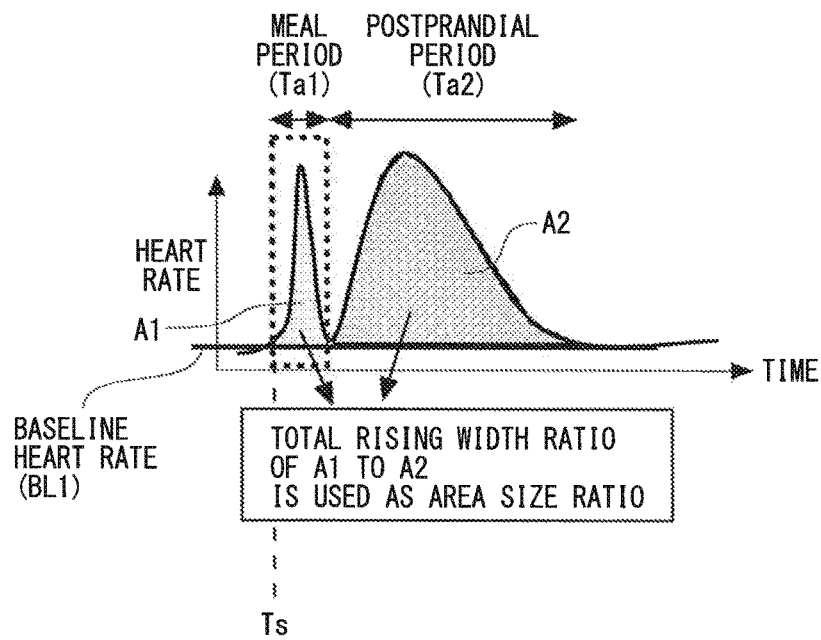
FIG. 7 is an explanatory diagram of an area size ratio between a first peak area and a second peak area.

FIG. 7 illustrates an explanatory diagram of detection of the characteristic quantity (1) as an area size ratio of the first peak area A1 to the second peak area A2 after the start of meal. The explanatory diagram illustrated in FIG. 7 is a graph of the variation of heartbeats after the start of meal, in which the axis of ordinates indicates the heartbeats per unit time, while the axis of abscissa indicates the elapse time (the period of time) since just before the start of meal.

In the explanatory diagram illustrated in FIG. 7, an area size (S1) of the first peak area A1 may be deemed as a total of rise widths of the heartbeats for, e.g., a meal period (Ta1). Herein, as indicated by a broken line, the meal period (Ta1) may be exemplified by a period for which the heartbeats having risen since the meal start time (Ts) are restored to the baseline heartbeats (BL1) via the first peak. Note that the baseline heartbeats (BL1) may adopt, e.g., the heartbeats upon the start of meal of the subject person or an average value of the average value of the heartbeats for the predetermined period instanced by 10 minutes, one hour and other equivalent periods before the start of meal. A method of setting the baseline heartbeats for calculating the area size (S1) of the first peak area A1 may be sufficient if common between or among the plurality of subject persons.

Note that the first peak area A1 involves assuming such a case that the heartbeats having risen since after the start of meal are not restored to the baseline heartbeats (BL1) via the first peak because of being affected by the peristaltic movement of the subject person. Therefore, the meal period (Ta1) may adopt, e.g., a period for which the heartbeats having varied since the meal start time (Ts) reach minimum heartbeats between the first peak and the second peak. Further, the meal period (Ta1) may adopt a period obtained by adding, a meal end time, a fixed period (e.g., 10-20 minutes) expended for the peristaltic movement as the elapse time since the meal start time (Ts) because of being affected by the peristaltic movement of the subject person. Similarly to the setting of the baseline heartbeats, a method of setting the meal period (Ta1) for calculating the area size (S1) of the first peak area A1 may be sufficient if common between or among the plurality of subject persons.

An area size (S2) of the second peak area A2 may be deemed as a total of rise widths of the heartbeats for, e.g., a postprandial period (Ta2). Herein, the postprandial period (Ta2) may be exemplified by, e.g., a period for which the heartbeats having risen since end time of the meal period (Ta1) in the first peak area A1 are restored to the baseline heartbeats (BL1) via the second peak.

Note that the second peak area A2 involves assuming such a case that the heartbeats having risen since after the start of meal are not restored to the baseline heartbeats (BL1) via the second peak because of being affected by the digestive activity of the subject person. Therefore, the postprandial period (Ta2) may be delimited into a fixed period (e.g., 4 hours or thereabout) expended for the digestive activity. For instance, the fixed period expended for the digestive activity since the end time of the meal period (Ta1) of the first peak area A1 may be set as the postprandial period (Ta2). Similarly to the setting of the meal period (Ta1), a method of setting the postprandial period (Ta2) for calculating the area size (S2) of the first peak area A2 may be sufficient if common between or among the plurality of subject persons.

The characteristic quantity (1) can be detected by "S1/S2" from the area size (S1) calculated in the first peak area A1 and the area size (S2) calculated in the second peak area A2.

[Detection of Characteristic Quantity R2]

Figure 8:
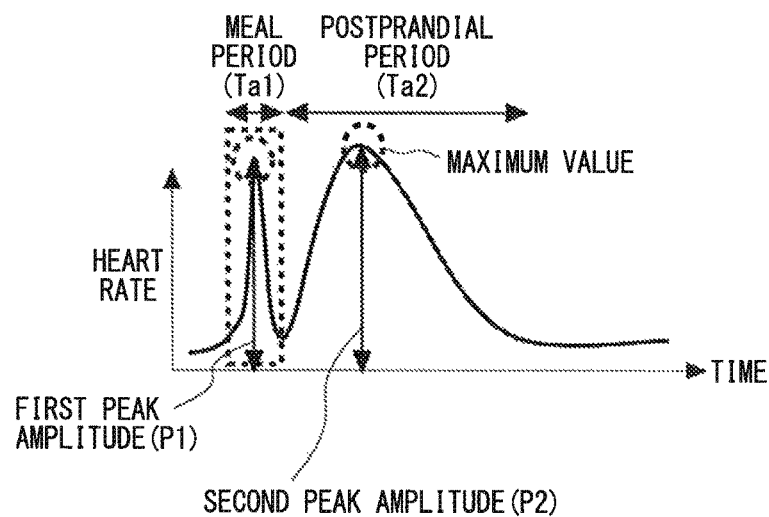
FIG. 8 is an explanatory diagram of amplitudes of a first peak and a second peak.

FIG. 8 illustrates an explanatory diagram of detection of the characteristic quantity R2 as an amplitude at each of the first peak and the second peak. The explanatory diagram illustrated in FIG. 8 is a graph of the variation of heartbeats after the start of meal, in which the axis of ordinates indicates the heartbeats per unit time, while the axis of abscissa indicates the elapse time (the period of time) since just before the start of meal.

In the explanatory diagram illustrated in FIG. 8, the amplitude of the first peak can be detected as, e.g., the maximum heartbeat value (P1) in the meal period (Ta1). Similarly, the amplitude of the second peak can be detected as, e.g., the maximum heartbeat value (P2) in the postprandial period (Ta2).

Note that the detection of the amplitude of the first peak may involve detecting a maximum value of the heartbeat rising width from the baseline heartbeats (BL1) illustrated in FIG. 7 in the meal period (Ta1). Similarly, the detection of the amplitude of the second peak may involve detecting a maximum value of the heartbeat rising width from the baseline heartbeats (BL1) illustrated in FIG. 7 in the postprandial period (Ta2).

Note that a time zone for detecting the maximum heartbeat value (P2) in, e.g., the postprandial period (Ta2) may be limited to a time zone in which the digestive activity will become most active because of being affected by the digestive activity of the subject person at the second peak. The time zone in which the digestive activity will become most active may be exemplified by a period of, e.g., 30-80 minutes after the meal start time (Ts).

[Detection of Characteristic Quantity R3]

FIGS. 9-12 illustrate explanatory diagrams of detection of the characteristic quantity R3 as each of the various response speeds at the first peak and the second peak. Each of the explanatory diagrams illustrated in FIGS. 9-12 is a graph of the variation of heartbeats after the start of meal, in which the axis of ordinates indicates the heartbeats per unit time, while the axis of abscissa indicates the elapse time (the period of time) since just before the start of meal.

Figure 9:
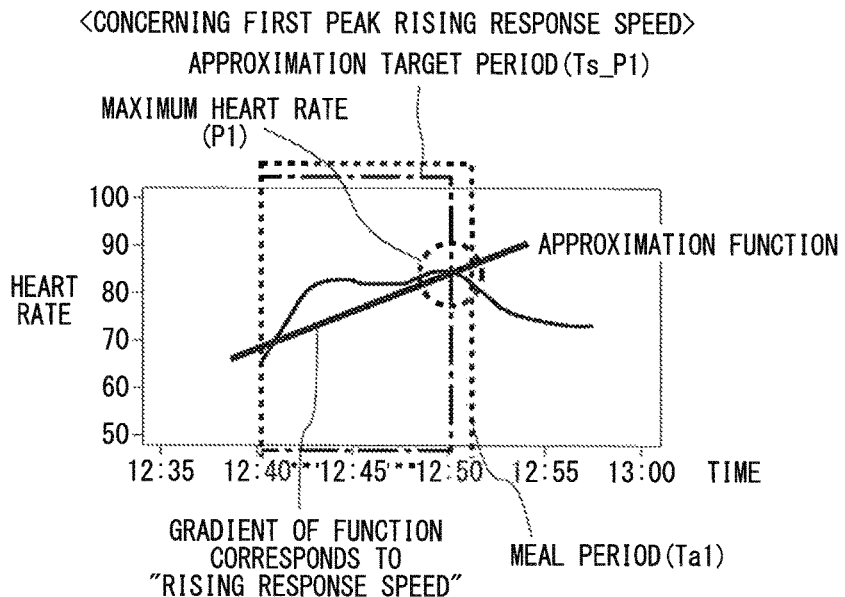
FIG. 9 is an explanatory diagram of a rising response speed of the first peak.
Figure 10:
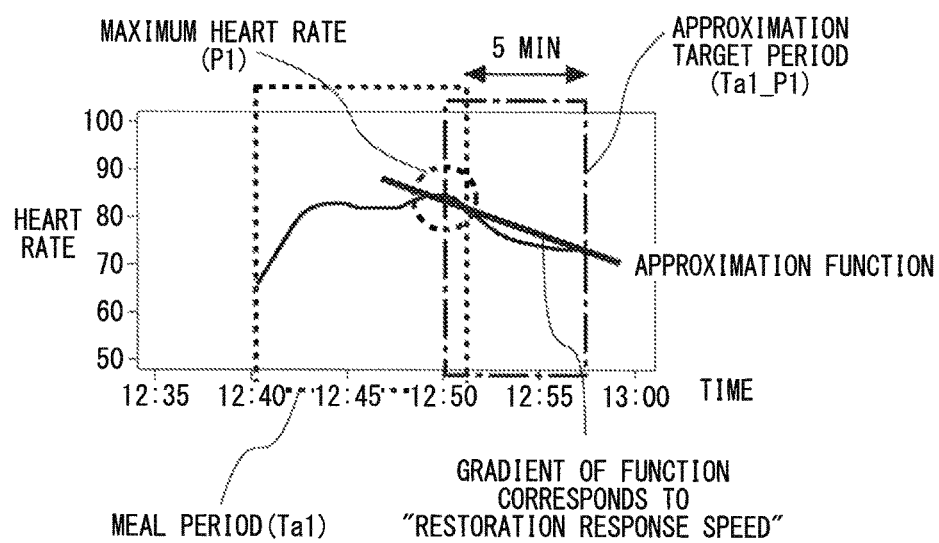
FIG. 10 is an explanatory diagram of a restoration response speed of the first peak.
Figure 11:
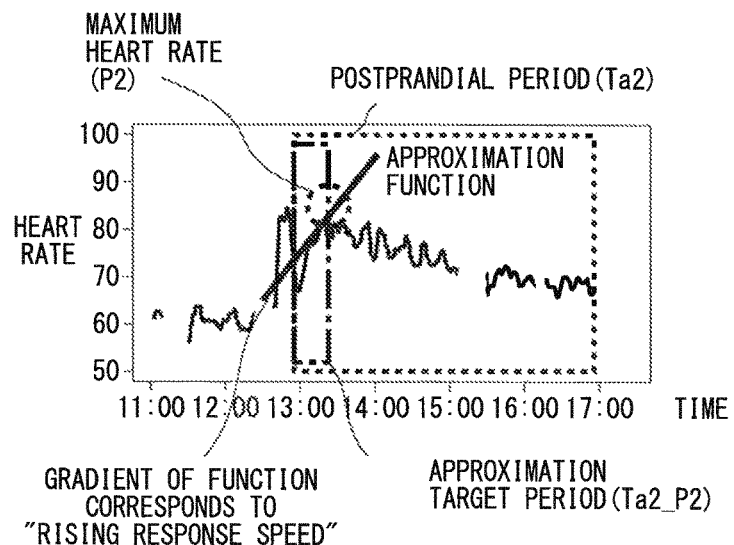
FIG. 11 is an explanatory diagram of a rising response speed of the second peak.
Figure 12:
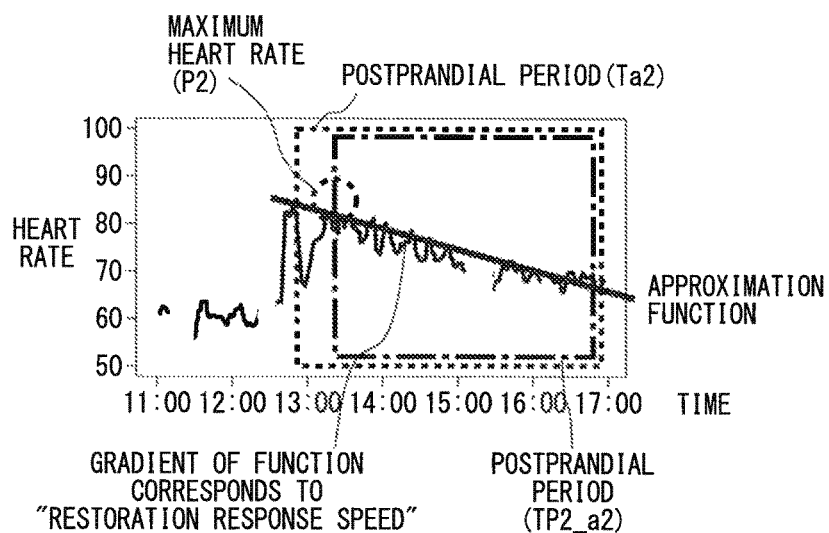
FIG. 12 is an explanatory diagram of the restoration response speed of the second peak.

FIG. 9 is the explanatory diagram of detection of the rising response speed at the first peak, and FIG. 10 is the explanatory diagram of detection of the restoration response speed at the first peak. The maximum heartbeats P1 defined as the amplitude of the first peak exist within a circle indicated by a broken line in each of FIGS. 9 and 10. A rectangular area indicated by a broken line in each of FIGS. 9 and 10 represents the meal period (Ta1). Similarly, FIG. 11 is an explanatory diagram of the detection of the rising response speed at the second peak, and FIG. 12 is an explanatory diagram of the detection of the restoration response speed at the second peak. The maximum heartbeats P2 defined as the amplitude of the second peak exist within a circle indicated by a broken line in each of FIGS. 11 and 12. A rectangular area indicated by a broken line in each of FIGS. 11 and 12 represents the postprandial period (Ta2).

In the explanatory diagram illustrated in FIG. 9, the rising response speed at the first peak may be detected as, e.g., a rising variation speed of the heartbeats since the meal start time (Ts) on the basis of the time when reaching the maximum heartbeats (P1) in the meal period (Ta1). For instance, a period till reaching maximum heartbeats (P1) since the meal start time (Ts) is set as an "approximate target period (Ts_P1)" (an area encompassed by a one-dotted chain line in FIG. 9). Then, a transition of the heartbeats in the approximate target period (Ts_P1) is extracted, and approximation of functions based on a linear function and other equivalent functions is conducted about the extracted transition of the heartbeats. Obtained subsequently is a gradient of the function approximated to the transition of the heartbeats in the approximate target period (Ts_P1), and this gradient can be detected as the rising response speed of the first peak.

The restoration response speed of the first peak can be likewise detected. In the explanatory diagram illustrated in FIG. 10, for instance, the restoration response speed of the first peak can be detected as a restoration variation speed of the heartbeats till the fixed period has elapsed after the end of meal since the time when reaching the maximum heartbeats (P1) in the meal period (Ta1). For example, a period till the elapse of the fixed period after the end of meal since the time when reaching the maximum heartbeats (P1) is set as an "approximate target period (Ta1_P1)" (an area encompassed by a one-dotted chain line in FIG. 10). Herein, the fixed period after the end of meal may be exemplified by a minute-base period instanced by 5 minutes.

Then, a transition of the heartbeats in the approximate target period (Ta1_P1) is extracted, and the approximation of functions based on the linear function and other equivalent functions is conducted about the extracted transition of the heartbeats. Obtained subsequently is a gradient of the function approximated to the transition of the heartbeats in the approximate target period (Ta1_P1), and this gradient can be detected as the restoration response speed of the first peak.

The detections of the rising response speed and the restoration response speed at the second peak will next be described with reference to FIGS. 11 and 12. The rising response speed and the restoration response speed at the second peak can be detected based on, e.g., the time when reaching the maximum heartbeats (P2) in the postprandial period.

In the explanatory diagram illustrated in FIG. 11, the rising response speed of the second peak can be detected as arising variation speed of the heartbeats since the start time of postprandial period (Ta2) (the end time of the meal period) on the basis of the time when reaching the maximum heartbeats (P2) in, e.g., the postprandial period (Ta2). For example, a period till the time when reaching the maximum heartbeats (P1) since the start time of the postprandial period (Ta2) is set as an "approximate target period (Ta2_P2) (an area encompassed by a one-dotted chain line in FIG. 11). Then, a transition of the heartbeats in the approximate target period (Ta2_P2) is extracted, and the approximation of functions based on the linear function and other equivalent functions is conducted about the extracted transition of the heartbeats. Obtained subsequently is a gradient of the function approximated to the transition of the heartbeats in the approximate target period (Ta2_P2), and this gradient can be detected as the rising response speed of the second peak.

In the explanatory diagram illustrated in FIG. 12, e.g., the restoration response speed of the second peak can be detected as a restoration variation speed of the heartbeats till a digestion end time since the time when reaching the maximum heartbeats (P2) in the postprandial period (Ta2). The digestion end time may be set as an end time of the postprandial period (Ta2). For instance, a period till the end time of the postprandial period since the time when reaching the maximum heartbeats (P2) in the postprandial period (Ta2) is set as an "approximate target period (TP2_a2)" (an area encompassed by a one-dotted chain line in FIG. 12). Then, a transition of the heartbeats in the approximate target period (TP2_a2) is extracted, and the approximation of functions based on the linear function and other equivalent functions is conducted about the extracted transition of the heartbeats. Obtained subsequently is a gradient of the function approximated to the transition of the heartbeats in the approximate target period (TP2_a2), and this gradient can be detected as the restoration response speed of the second peak.

[Detection of Characteristic Quantity R4]

Figure 13:
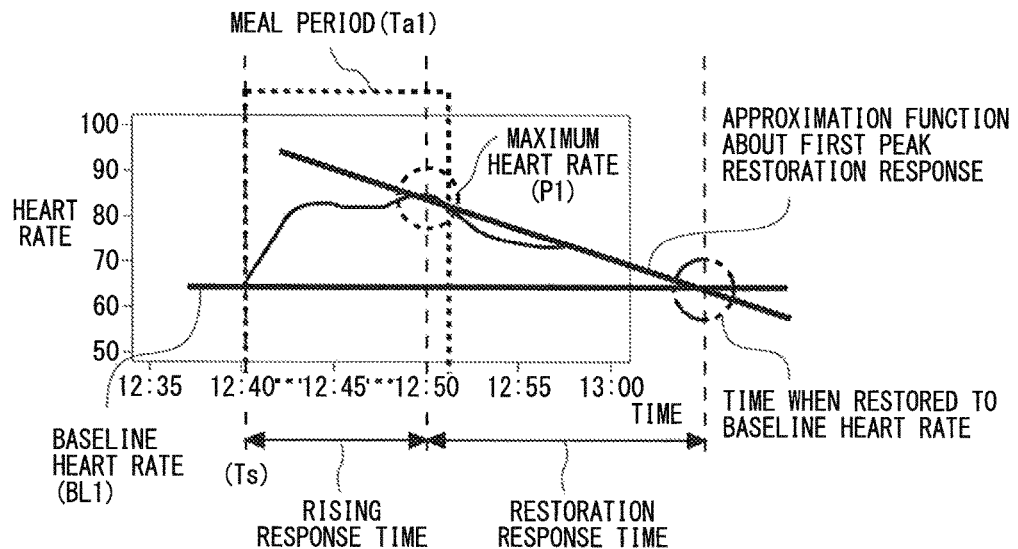
FIG. 13 is an explanatory diagram of the rising response time and the restoration response time of the first peak.
Figure 14:
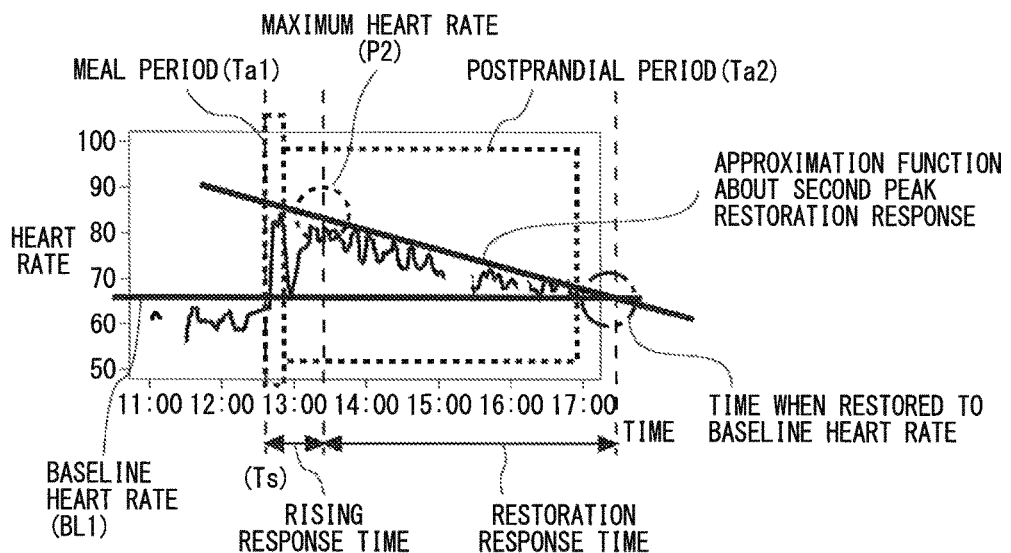
FIG. 14 is an explanatory diagram of the rising response time and the restoration response time of the second peak.

FIGS. 13-14 illustrate explanatory diagrams of detection of the characteristic quantity R4 as each of the various response times at the first peak and the second peak. Each of the explanatory diagrams illustrated in FIGS. 13-14 is a graph of the variation of heartbeats after the start of meal, in which the axis of ordinates indicates the heartbeats per unit time, while the axis of abscissa indicates the elapse time (the period of time) since just before the start of meal. FIG. 13 is an explanatory diagram of detecting the rising response time and the restoration response time of the first peak, and FIG. 14 is an explanatory diagram of detecting the rising response time and the restoration response time of the second peak.

In the explanatory diagram illustrated in FIG. 13, an area encompassed by a short broken line represents the meal period (Ta1), and the maximum heartbeats P1 defined as the amplitude of the first peak exists within a region encircled by a broken line in the area encompassed by the short broken line. The rising response time of the first peak can be detected as a period of time till the time when reaching the maximum heartbeats (P1) in the meal period (Ta1) since the start time (the meal start time (Ts)) of, e.g., the meal period (Ta1).

Further, the restoration response time of the first peak can be detected as a period of time till the heartbeats are restored to the baseline heartbeats (BL1) since the time when reaching the maximum heartbeats P1 in, e.g., the meal period (Ta1). Note that the first peak involves assuming such a case that the heartbeats are not restored to the baseline heartbeats (BL1) for a period till reaching the second peak because of being affected by the peristaltic movement of the subject person. Therefore, the restoration response time of the first peak may also be obtained by using the restoration response speed of the first peak in the characteristic quantity R3 described in, e.g., FIG. 10.

The restoration response speed of the first peak described in FIG. 10 is detected as, e.g., a gradient of the approximate function approximated from the transition of the heartbeats to be restored after the first peak. In other words, as illustrated in FIG. 13, an elapse time till a time variation of the heartbeats to transition with the gradient of the approximate function from the heartbeats (the maximum heartbeats P1) of the first peak reaches the baseline heartbeats (BL1), may be detected as the restoration response time of the first peak.

In the explanatory diagram illustrated in FIG. 13, the elapse time till reaching the baseline heartbeats (BL1) in the approximate function representing the restoration variation of the heartbeats that intersects the maximum heartbeats P1, is exemplified as a "restoration response time". Note that a circle indicated by the one-dotted chain line represents an intersection between the approximate function representing the restoration variation intersecting the maximum heartbeats P1 and the baseline heartbeats (BL1). The restoration response time of the first peak can be detected by, e.g., obtaining a differential heartbeat between the maximum heartbeats P1 in the meal period (Ta1) and the baseline heartbeats (BL1), and dividing this differential heartbeat by the gradient of the approximate function defined as the restoration response speed of the first peak.

The rising response time and the restoration response time of the second peak can be likewise detected. In the explanatory diagram illustrated in FIG. 14, the areas encompassed by the short broken lines represent the meal period (Ta1) and the postprandial period (Ta2), and the circle indicated by the broken line of the postprandial period (Ta2) contains the maximum heartbeats P2 defined as an amplitude of the second peak. The rising response time of the second peak can be detected as, e.g., a period of time till the time when reaching the maximum heartbeats (P2) in the postprandial period (Ta2) since the start time (the meal start time (Ts)) of the meal period (Ta1).

The restoration response time of the second peak can be detected as, e.g., a period of time till the heartbeats are restored to the baseline heartbeats (BL1) since the time when reaching the maximum heartbeats P2 in the postprandial period (Ta2). Herein, the second peak involves assuming such a case that the heartbeats are note restored to the baseline heartbeats (BL1) from the second peak onward because of being affected by the digestive activity of the subject person. Consequently, the restoration response time of the second peak may also be obtained by using the restoration response speed of the second peak in the characteristic quantity R3 described in, e.g., FIG. 12.

The restoration response speed of the second peak described in FIG. 12 is detected as a gradient of the approximate function approximated from the transition of the heartbeats to be restored, e.g., after the second peak. To be specific, as illustrated in FIG. 14, the elapse time till the time variation of the heartbeats to transition with the gradient of the approximate function from the heartbeats (the maximum heartbeats P2) of the second peak reaches the baseline heartbeats (BL1), may be detected as the restoration response time of the second peak.

In the explanatory diagram illustrated in FIG. 14, the elapse time till reaching the baseline heartbeats (BL1) in the approximate function representing the restoration variation of the heartbeats that intersects the maximum heartbeats P2, is exemplified as a "restoration response time". Note that a circle indicated by the one-dotted chain line represents an intersection between the approximate function representing the restoration variation intersecting the maximum heartbeats P2 and the baseline heartbeats (BL1). The restoration response time of the second peak can be detected by, e.g., obtaining a differential heartbeat between the maximum heartbeats P2 in the postprandial period (Ta2) and the baseline heartbeats (BL1), and dividing this differential heartbeat by the gradient of the approximate function defined as the restoration response speed of the second peak.

FIG. 15 illustrates an example of a table in which the characteristic quantities R1-R4 detected at the first peak and the second peak after the start of the meal of the subject person are sorted as parameters for narrowing down the subject person.

In the example of the table illustrated in FIG. 15, the characteristic quantities R1-R4 detected at the first peak and the second peak after the start of the meal of the subject person are registered in a "heartbeat characteristic quantity" field. An "area size ratio" registered in the "heartbeat characteristic quantity" field corresponds to an area size ratio of the area size (S1) of the first peak area A1 (1) to the area size (S2) of the second peak area A2 of the characteristic quantity. Similarly, an "amplitude" corresponds to the maximum heartbeats P1 of the first peak and the maximum heartbeats P2 of the second peak of the characteristic quantity R2.

Further, in the example of the table of FIG. 15, a "response speed" registered in the "heartbeat characteristic quantity" field corresponds to the various response speeds of the characteristic quantity R3 at the first peak and the second peak, respectively. To be specific, the "response speed" responds to, with respect to the first peak, the rising response speed and the restoration response speed at the first peak, and corresponds to, with respect to the second peak, the rising response speed and the restoration response speed at the first peak. A "response time" registered in the "heartbeat characteristic quantity" field corresponds to the various response times about each of the first peak and the second peak in the characteristic quantity R4. To be specific, the "response time" corresponds, with respect to the first peak, the rising response time and the restoration response time at the first peak, and corresponds to, with respect to the second peak, the rising response time and the restoration response time at the first peak.

Eleven characteristic quantities of four categories illustrated in FIG. 15 are acquired as, e.g., parameters representing the characteristics of the heartbeats per candidate, and the thus-acquired parameters are managed as a database (DB) by being associated with the candidates. Upon occurrence of an event instanced by narrowing down the subject person and other equivalent events, the parameters of eleven characteristic quantities of four categories stored in the database and acquired from the individual candidates containing the subject person are checked with any one of the parameters of eleven characteristic quantities of four categories acquired from the subject person. The check of the characteristic quantity acquired from the subject person and representing the characteristic of the heartbeats with the characteristic quantities stored in the database, enables the candidates to be narrowed down, who may be deemed to be the subject persons, from within the plurality of candidates.

Note that the variation of heartbeats associated with the meal is assumed to be affected by, e.g., the time zone of the meal and the 24-hour circadian rhythm data of a human body. The characteristic quantities illustrated in FIG. 15 may also be managed by being associated a plurality of time zones. When narrowing down the subject person, a check with the characteristic quantity per time zone may be carried out. The use of the characteristic quantity per time zone enables the subject person to be narrowed done corresponding to a living habit of the subject person.

Division of the time zone for acquiring the characteristic quantities can be exemplified by segmentation into four time zones, e.g., a breakfast, a lunch, a supper and a late night snack. When segmented into the four time zones, for instance, the breakfast may be set to cover a time zone from 5:00 to 11:00, the lunch may be set to cover a time zone from 11:00 to 17:00, the supper may be set to cover a time zone from 17:00 to 24:00, and the late night snack may be set to cover a time zone from 24:00 to 5:00, respectively.

[Narrowing-Down of Subject Person]

Described next with reference to the drawing in FIGS. 16 and 17 are how the subject person is narrowed down by use of the eleven characteristic quantities of four categories representing the characteristic quantities R1-R4 of the heartbeats, the quantities being detected about the first peak and the second peak after the start of meal of the subject person. FIG. 16 illustrates an example of a plotted diagram configured by associating the respective characteristic quantities with each other by using the restoration speed of the second peak and the amplitude of the first peak in the eleven parameters of four categories. In FIG. 16, the axis of ordinates indicates the restoration speed of the second peak, while the axis of abscissa indicates the amplitude. The number of subject persons from whom the characteristic quantities are acquired is "4", a sample count with the characteristic quantities being acquired is "8", and a target time zone for acquiring the characteristic quantities is the time zone (11:00-17:00) for the lunch.

In the explanatory diagram illustrated in FIG. 16, a rectangular area Z1 represents a sample detection range of the characteristic quantities (the restoration speed of the second peak, the amplitude range of the first peak) detected about a candidate A. Similarly, a rectangular area Z2 represents a sample detection range of the characteristic quantities detected about a candidate B, a rectangular area Z3 is about a candidate C, and a rectangular area Z4 is about a candidate D.

As depicted in FIG. 16, the samples of the characteristic quantities detected from the individual candidates are scattered in predetermined detection ranges, and therefore result in having the range areas (the rectangular areas Z1-Z4) associated with, e.g., maximum values and minim values of the detected samples. It is then recognized that each of the rectangular areas specified from the range areas with the samples being scattered becomes the area unique to each candidate.

In the example of FIG. 16, the rectangular area Z1 defined as a range for detecting the characteristic quantity of the candidate A is a substantially broad area of the range, while the rectangular area Z3 defined as a range for detecting the characteristic quantity of the candidate C is a substantially narrow area of the range. It is recognized that in a relation between the restoration speed of the second peak and the amplitude range of the first peak of the candidate A, the detection values tend to be grouped over a broad range, while in the same relation therebetween about the candidate C, the detection values tend to be grouped concentratedly in a narrow range.

Further in the example of FIG. 16, the rectangular area Z1 of the candidate A, the rectangular area Z3 of the candidate C and the rectangular area Z4 of the candidate D have an overlapped area of the ranges; however, the rectangular area Z3 of the candidate B is overlapped with none of the rectangular areas Z1, Z2, Z4 of other candidates. It is understood that the rectangular area Z3 of the candidate B deviates relatively from the detection range of the characteristic quantities of other candidates. It is therefore construed that the candidates A, C, D are hard to be narrowed down for other candidates as the case may be, depending on the detected characteristic quantities, in the relation between the restoration speed of the second peak and the amplitude range of the first peak. While on the other hand, the candidate B can be narrowed down for the candidate B to a substantially high degree of coincidence with the detected characteristic quantities at least in the relation between the restoration speed of the second peak and the amplitude range of the first peak.

For example, when the characteristic quantity indicated by a mark "x" in FIG. 16 is detected, the subject person having the detected characteristic quantity among the plurality of candidates A-D can be associated with the candidate B to the substantially high degree of coincidence.

Thus, the subject person is narrowed down from within the plurality of candidates, in which case the range area is specified on a candidate-by-candidate basis, the range area being associated with the maximum value and the minimum value of the characteristic quantity detected with respect to each of the eleven characteristic quantities of four categories representing, e.g., the pre-acquired characteristic quantities R1-R4 of the heartbeats. Then, the specified range area of each of the parameters of the eleven characteristic quantities of four categories is checked with the characteristic quantity detected from the subject person. When the characteristic quantity detected from the subject person is detected from within a unique range area specified per candidate, the relevant candidate can be extracted as a candidate who may be deemed to be the subject person.

The explanatory diagram in FIGS. 16 and 17 have described so far that the range of the characteristic quantity detected on the candidate-by-candidate basis is unique by using the two characteristic quantities (parameters) in the eleven characteristic quantities of four categories for the convenience of representation to be visualized. The range areas, detected on the candidate-by-candidate basis, of the eleven characteristic quantities of four categories are further organized into pluralities of combinations (combinations of eleven parameters at the maximum), thereby enabling clarification of the range area unique to each candidate. In the explanatory example of FIG. 16, it is feasible to further clarify the respective characteristic quantities of the candidates A, C, D having the overlapped range area, and it is also possible to perform the narrowing-down among the candidates A, C, D with respect to the detected characteristic quantities.

FIG. 18 illustrates an explanatory diagram of the range area of the characteristic quantity when increasing the number of parameters. S01 in FIG. 18 is an explanatory diagram of the range area when using an area size ratio and the characteristic quantity of the restoration speed of the second peak with respect to the candidates C, D illustrated in FIG. 16. In S01 of FIG. 18, the axis of ordinates indicates the area size ratio, while the axis of abscissa indicates the restoration speed of the second peak, and a sample count of the characteristic quantity is set to 8 samples given by targeting on the lunch time zone. S02 in FIG. 18 is an explanatory diagram of the range area when adding a characteristic quantity of a first peak amplitude with respect to the candidates C, D. In the explanatory diagram of S02 in 18, a triaxial characteristic quantity space based on the area size ratio, the restoration speed of the second peak and a first peak amplitude is configured by adding a reference axis representing the first peak amplitude.

As illustrated in S01 of FIG. 18, a range area of a rectangular area Z5 about the candidate C is configured from the maximum value and the minimum value of the samples of the detected characteristic quantities (the area size ratio, the restoration speed of the second peak); and a range area of a rectangular area Z6 about the candidate D is thus configured. It is understood that the rectangular area Z5 of the candidate C and the rectangular area Z6 of the candidate D have an overlapped area in the vicinity of the area size ratio being, e.g., "0.04". It is also recognized that a majority of the rectangular area Z5 of the candidate C falls within a range with the area size ratio being roughly equal to or smaller than "0.04", while a majority of the rectangular area Z6 of the candidate D falls within a range with the area size ratio being roughly equal to or larger than "0.04".

For example, an assumption is that an overlap rate (%) and a determination disabled rate (%) of the detected characteristic quantity with respect to the overlapped area between the rectangular area Z5 and the rectangular area Z6 are to be obtained in the following Mathematical Expressions (A), (B).

Overlap Rate (%): (2×(Overlapped Area))/((Rectangular Area Z5)+(Rectangular Area Z6))     Mathematical Expression (A)

Determination Disabled Rate (%): (Sample Count Detected in Overlapped Area)/(Sample Count of Candidate C+Sample Count of Candidate D)     Mathematical Expression (B)

Herein, each rectangular area may be exemplified as a minimum rectangle (left upper point, left lower point) covering a sample data existing range per candidate. Note that the "area" in the mathematical expression (A) is defined by a range width (maximum value−minimum value) of the dispersion (distribution) of the characteristic quantity, e.g., when giving one set of the characteristic quantity for use. When giving two sets of the characteristic quantities for use, the area is expressed as a quantity of the two-dimensional area obtained by multiplying (combining) range widths of dispersions of the two sets of characteristic quantities; and when giving three sets of the characteristic quantities for use, the area is expressed as a quantity of the three-dimensional volume obtained by multiplying (combining) range widths of dispersions of the three sets of characteristic quantities.

Upon applying the overlap rate (%) in the mathematical expression (A) and the determination disabled rate (%) in the mathematical expression (B) to the characteristic quantities detected with respect to the candidates C, D in S01 of FIG. 18, for example, the overlap rate (%) becomes 17.0(%), and the determination disabled rate (%) becomes 17.6(%).

In S01 of FIG. 18, when adding next the first peak amplitude as the characteristic quantity, it follows that the area of the characteristic quantity unique to the candidate is, as illustrated in S02 of FIG. 18, expressed in the triaxial characteristic quantity space based on the area size ratio, the restoration speed of the second peak and the first peak amplitude. As depicted in S02 of FIG. 18, an area Z7 for the candidate C is configured from the maximum value and the minimum value of the samples of the detected characteristic quantities (the area size, the restoration speed of the second peak, the first peak amplitude), and an area Z8 for the candidate D is also thus configured.

Upon applying the overlap rate (%) in the mathematical expression (A) and the determination disabled rate (%) in the mathematical expression (B) to the characteristic quantities detected with respect to the candidates C, D in S02 of FIG. 18, the overlap rate becomes 10.0(%), and the determination disabled rate becomes 11.8(%). With respect to the eleven characteristic quantities of four categories detected on the candidate-by-candidate basis, the number of characteristic quantity sets to be used for specifying the range of the characteristic quantities unique to the individuals is increased to "3" from "2", in which case it is recognized that the overlap rate and the determination disabled rate are improved (decrease in numeric value).

As described above, the area overlapped between or among the candidates can be further reduced by obtaining a plurality of combinations (combinations of the eleven parameters at the maximum) of the range areas of the eleven characteristic quantities of four categories detected on the candidate-by-candidate basis, thereby enabling the overlap rate and the determination disabled rate to be improved. In other words, it is feasible to improve accuracy of extracting the candidates who can be deemed as the subject persons from within the plurality of candidates.

Note that a checking range suited to a purpose can be set as the range area of the each parameter used on the occasion of performing the narrowing-down. For example, in the explanatory diagram illustrated in FIG. 16, the rectangular area Z1 about the candidate A encompasses an area not overlapped with the candidates C, D, and the rectangular area Z4 about the candidate D encompasses an area not overlapped with the candidate C. For example, the range area to be checked about the restoration speed of the second peak illustrated in FIG. 16 is set to a range of "−4" through "−7", while the first peak amplitude is set to a range of "80" through "100", thereby enabling segmentation of checking data used for narrowing down the subject person.

EXAMPLE 2

Figure 19:
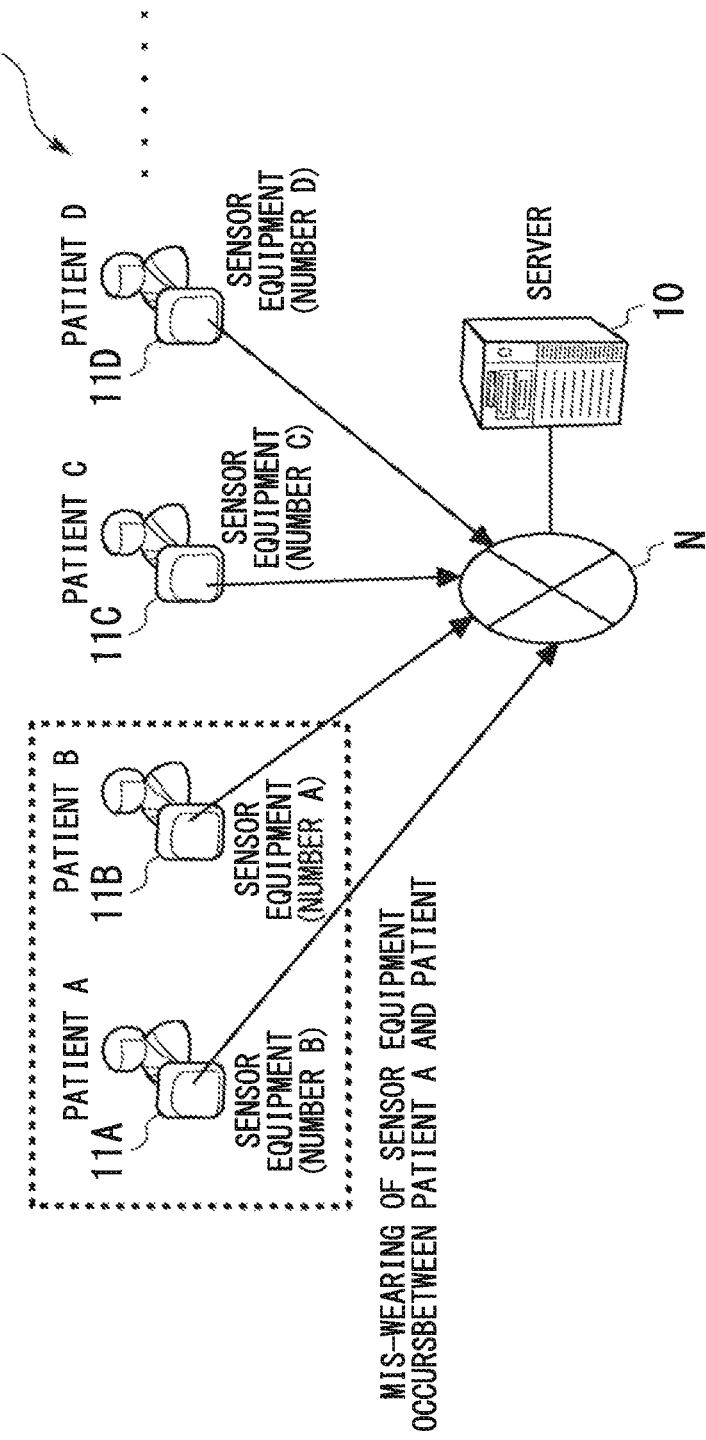
FIG. 19 is a diagram illustrating an information processing system according to an embodiment.

FIG. 19 illustrates one example of an information processing system 1 according to the embodiment. An information processing system 1 depicted in FIG. 19 detects characteristics of the heartbeats associated with the meals from, e.g., a plurality of patients (candidates). The information processing system 1 has a function to narrow down the candidates who can be deemed as the subject persons having the detected characteristics of the heartbeats by referring to pre-acquired characteristics of the heartbeats associated with the meals on a patient-by-patient basis from the detected characteristics of the heartbeats. The information processing system 1 narrows down the candidates from the detected characteristics of the heartbeats, thereby enabling confirmation of a true wearer of a sensor equipment 11 worn to every patient in order to continuously grasp a state of health of each patient.

The information processing system 1 illustrated in FIG. 19 includes an information processing apparatus 10 and a plurality of sensor equipments 11, which are connected to, e.g., a network N. The network N embraces a public network instanced by the Internet and other equivalent networks, a wireless network instanced by a mobile phone network and other equivalent networks, and a network instanced by LAN (Local Area Network) and other equivalent networks.

In the information processing system 1 of FIG. 19, the information processing apparatus 10 is exemplified by a computer instanced by a server, a personal computer (PC) and other equivalent apparatuses. The information processing apparatus 10 accepts the characteristics of the heartbeats associated with the meals, the characteristics being detected by the sensor equipments 11 connected thereto via the network N. The information processing apparatus 10 accepts the eleven characteristic quantities of four categories of the heartbeats associated with the meals, the characteristic quantities being illustrated in FIG. 15 and other equivalent Figures. The information processing apparatus 10 refers to the characteristic quantities associated with the meals on the patient-by-patient basis, which are stored beforehand in a database and other equivalent storages, and checks these characteristic quantities with the accepted characteristic quantities of the heartbeats.

The information processing apparatus 10 determines whether the characteristic quantities, accepted from the sensor equipments 11, of the heartbeats associated with the meals are embraced by a predetermined area specified by the maximum value and the minimum value of the characteristic quantities stored in the database and other equivalent storages, and narrows down the candidates who can be deemed to be the wearers of the sensor equipments 11. The information processing apparatus 10, when there is a discrepancy between an identification number allocated to the sensor equipment 11 and the candidate being narrowed down from the characteristic quantities of the heartbeats, issues an alert instanced by an alarm and other equivalent signals, and outputs a list of candidates who can be deemed to be the wearers of the sensor equipments 11. As a result, the information processing apparatus 10 can confirm the true wearer even when the sensor equipment 11 worn to each patient is erroneously worn due to a mistake and other equivalent errors.

The sensor equipment 11 is an information processing apparatus including an input unit equipped with a sensor to detect the characteristics of the heartbeats associated with the meals of the wearer. The identification number or other equivalent information for uniquely identifying the wearer is previously allocated to the sensor equipment 11. In the example of FIG. 19, an identification number "A" is allocated to the sensor equipment 11 worn to a patient A. Similarly, identification numbers "B", "C", "D" are allocated to patients B, C, D. In the following discussion, the sensor equipment 11 worn to the patient A is also referred to as a "sensor equipment 11A". The sensor equipments 11 worn to the patients B-D are likewise termed a "sensor equipment 11B", a "sensor equipment 11C", a "sensor equipment 11C" and a "sensor equipment 1D", respectively.

Note that the example in FIG. 19 illustrates a state in which the sensor equipment 11A to be worn to the patient A is mistakenly worn to the patient B, while the sensor equipment 11B to be worn to the patient B is mistakenly worn to the patient A.

The sensor equipment 11 includes a heartbeat sensor to detect a heart rate of the wearer per unit time, an acceleration sensor to detect vibrations (a variation in acceleration) of the wearer in vertical, bilateral and back-and-forth directions associated with actions in meal, and other equivalent sensors. The sensor equipment 11 detects, e.g., a time-series variation in heart rate per unit time, the heart rate being detected by the heartbeat sensor. The sensor equipment 11 specifies, e.g., a meal start time and other equivalent times from the vibrations and other equivalent actions in the vertical, bilateral and back-and-forth directions, the vibrations being detected by the acceleration sensor. The sensor equipment 11 specifies a kinetic activity instanced by patient's walking, going up and down stairs and other equivalent activities from the vibrations and other equivalent actions in the vertical, bilateral and back-and-forth directions, the vibrations being detected by the acceleration sensor.

The sensor equipment 11 detects, e.g., the eleven characteristic quantities of four categories illustrated in FIG. 15 from sensor information on the detected variation in heart rate, the detected variation in acceleration in the vertical, bilateral and back-and-forth directions, and other equivalent variations. The sensor equipment 11 associates the eleven characteristic quantities of four categories with, e.g., the identification number allocated to the sensor equipment 11, and thus outputs these characteristic quantities to the network N. The information processing apparatus 10 accepts the eleven characteristic quantities of four categories being output to the network N.

Note that the detection of the heart rate of the wearer wearing the sensor equipment 11 is not limited to using a contact type sensor to detect the heart rate by being brought into contact with the wearer. For example, the detection of the heart rate may also be specified from a time-series variation of captured images of the wearer of the sensor equipment 11, the variations being acquired at a time interval of 1/20 sec. The detection of the heart rate may further be specified by detecting a Doppler frequency associated with pulsations by use of, e.g., RF (Radio Frequency) and other equivalent frequencies. It may be sufficient that the variation of heartbeats after the start of meal of the subject person can be detected. However, the sensor equipment 11 may notify the information processing apparatus 10 of detection values of the variations of the heart rate, the acceleration and other equivalent variations, and the information processing apparatus 10 may calculate physical quantities based on the detection values.

[Configuration of Apparatus]

Figure 20:
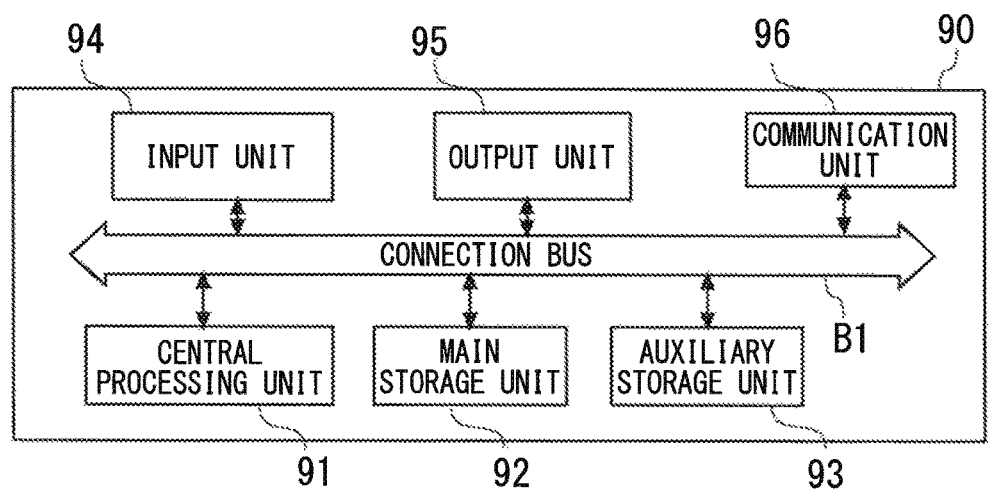
FIG. 20 is an explanatory diagram illustrating an example of a hardware configuration of an information processing apparatus.

FIG. 20 illustrates a hardware configuration of an information processing apparatus 90. The information processing apparatus 90 illustrated in FIG. 20 has a configuration of a so-called general computer. The information processing apparatus 10 and the sensor equipment 11 depicted in FIG. 19 are attained by the information processing apparatus 90 illustrated in, e.g., FIG. 20.

The information processing apparatus 90 illustrated in FIG. 20 includes a CPU (Central Processing Unit) 91, a main storage unit 92, an auxiliary storage unit 93, an input unit 94, an output unit 95 and a communication unit 96, which are interconnected via a connection bus B1. The main storage unit 92 and the auxiliary storage unit 93 are non-transitory recording mediums being readable by the information processing apparatus 90.

The information processing apparatus 90 controls peripheral devices by the CPU 91 deploying a program stored in the auxiliary storage unit 93 into an operation area of the main storage unit 92 in an executable manner and executing the program. The information processing apparatus 90 is thereby enabled to attain functions suited to predetermined purposes.

In the information processing apparatus 90 illustrated in FIG. 20, the CPU 91 is a central processing unit to control the whole information processing apparatus 90. The CPU 91 executes processes based on the program stored in the auxiliary storage unit 93. The main storage unit 92 is a non-transitory storage medium that caches the program and data, and to deploys the operation area. The main storage unit 92 includes, e.g., a RAM (Random Access Memory) and a ROM (Read Only Memory).

The auxiliary storage unit 93 stores various categories of programs and various items of data on the non-transitory recording medium in a readable/writable manner. The auxiliary storage unit 93 is also called an external storage device. The auxiliary storage unit 93 stores Operating System (OS), the various categories of programs, various types of tables and other equivalent software components. The OS includes a communication interface program to transfer and receive the data to and from external devices and other equivalent devices connected via the communication unit 96. The external devices include, e.g., other information processing apparatuses instanced by the servers and other equivalent apparatuses, the external storage devices, and devices having communication functions and other equivalent devices.

The auxiliary storage unit 93 is exemplified by an EPROM (Erasable Programmable ROM), a solid state drive, a hard disk drive (HHD) and other equivalent storages. The auxiliary storage unit 93 may be instanced by a CD drive, a DVD drive, a BD (Blu-ray (registered trademark) Disc) drive and other equivalent drives. The recording medium is exemplified by a silicon disk including a nonvolatile semiconductor memory (flash memory), a hard disk, a CD, a DVD, a BD, a USB (Universal Serial Bus) memory, a memory card and other equivalent mediums.

The input unit 94 accepts an operation instruction and other events from a user or other equivalent persons. The input unit 94 is an input device exemplified by an input button, a keyboard, a pointing device, a wireless remote controller, a microphone, a camera and other equivalent devices. The input unit 94 includes a variety of sensors instanced by the heartbeat sensor to detect the heart rate of the wearer, and the acceleration sensor to detect the accelerations in the vertical, bilateral and back-and-forth directions. The input unit 94 notifies the CPU 91 of the information inputted from the input unit 94 via the connection bus B1.

The output unit 95 outputs the data to be processed by the CPU 91 and the data to be stored on the main storage unit 92. The output unit 95 is an output device instanced by a CRT (Cathode Ray Tube) display, an LCD (Liquid Crystal Display), a PDP (Plasma Display Panel), an EL (Electroluminescence) panel, an organic EL panel, a printer, a speaker and other equivalent devices. The communication unit 96 is an interface with, e.g., the network N and other equivalent networks.

Figure 21:
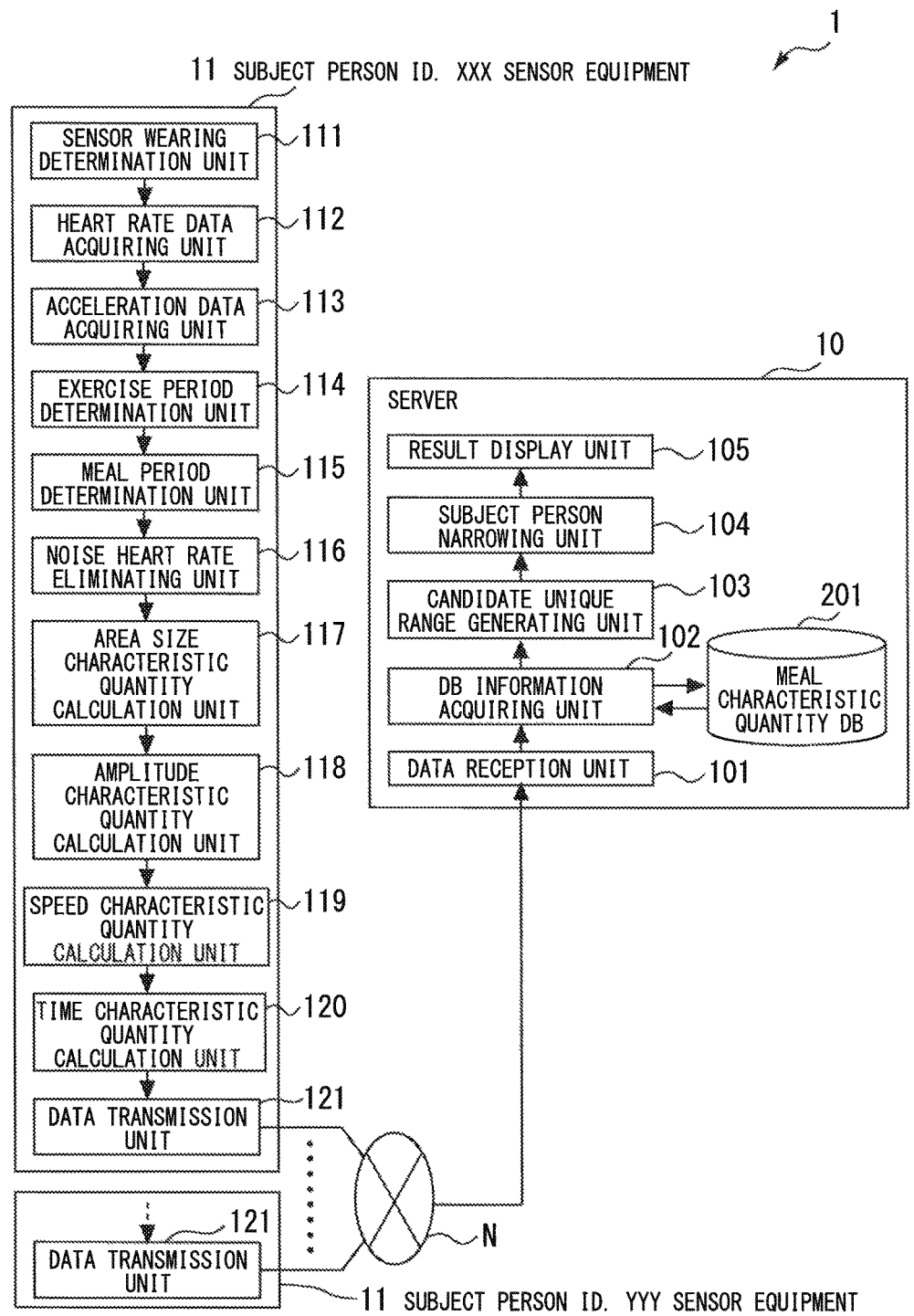
FIG. 21 is an explanatory diagram illustrating a configuration of functions of the information processing system according to the embodiment.

The information processing apparatus 10 attains a variety of processing units illustrated in FIG. 21 along with execution of target programs by the CPU 91 reading OS, the various categories of programs and the various items of data stored in the auxiliary storage unit 93 into the main storage unit 92 and executing these software components. Along with the execution of the target programs, the information processing apparatus 10 attains a data reception unit 101, a DB information acquiring unit 102, a candidate unique range generating unit 103, a subject person narrowing unit 104, and a result display unit 105 illustrated in FIG. 21. However, any or a part of these processing units illustrated in FIG. 21 may also be operated by hardware circuits.

Note that any of the processing units may be included in another information processing apparatus or another equivalent apparatus. For example, the information processing apparatus including the data reception unit 101, the information processing apparatus including the DB information acquiring unit 102, the information processing apparatus including the candidate unique range generating unit 103, and the information processing apparatus including the result display unit 105 may be interconnected via the network N or other equivalent networks. The information processing apparatus including the subject person narrowing unit 104 and a meal characteristic quantity DB 201 stored in the external storage device may be connected to the network N, resulting in functioning as the information processing apparatus 10. The information processing apparatus 10 can be attained as cloud computing, i.e., a group of computers on the network N, thereby enabling processing loads on the respective processing units to be reduced.

The sensor equipment 11 attains the respective processing units illustrated in FIG. 21 along with the execution of the target programs by the CPU 91 reading the OS, the various categories of programs and the various items of data stored in the auxiliary storage unit 93 into the main storage unit 92 and executing these software components. Along with the execution of the target programs, the sensor equipment 11 attains a sensor wearing determination unit 111, a heart rate data acquiring unit 112, an acceleration data acquiring unit 113, an exercise period determination unit 114, a meal period determination unit 115, and a noise heart rate eliminating unit 116 depicted in FIG. 21. Along with the execution of the target programs, the sensor equipment 11 further attains an area size characteristic quantity calculation unit 117, an amplitude characteristic quantity calculation unit 118, a speed characteristic quantity calculation unit 119, a time characteristic quantity calculation unit 120, and a data transmission unit 121 illustrated in FIG. 21. However, the sensor equipment 11 may also provide the processing units in FIG. 21 not by being installed with the OS but by using a control program for executing a control sequence and processing arithmetic operations, and using firmware or other equivalent software components.

Note that in the processing units of the sensor equipment 11, e.g., the information processing apparatus 10 may include other processing units exclusive of the sensor wearing determination unit 111, the heart rate data acquiring unit 112, the acceleration data acquiring unit 113 and the data transmission unit 121.

Further, the sensor equipment may also include the processing units, i.e., the DB information acquiring unit 102, the candidate unique range generating unit 103, the subject person narrowing unit 104 and the result display unit 105 of the information processing apparatus 10. The sensor equipment 11 including the aforementioned processing units of the information processing apparatus 10 may connect to the meal characteristic quantity DB 201 connected to the network N or other equivalent networks, thereby notifying the wearer of the sensor equipment 11 that the sensor equipment is mistakenly worn.

[Configuration of Processing Block]

FIG. 21 illustrates an explanatory diagram of processing blocks in the information processing system 1 according to the embodiment. In the explanatory diagram illustrated in FIG. 21, the information processing apparatus 10 includes the processing units, i.e., the data reception unit 101, the DB information acquiring unit 102, the candidate unique range generating unit 103, the subject person narrowing unit 104 and the result display unit 105. The information processing apparatus 10 includes the auxiliary storage unit 93 equipped with the meal characteristic quantity DB 201 as a storage location of the data to which the aforementioned processing units refer or the data to be managed by the processing units. History values of the meal characteristic quantities of each candidate are stored in the meal characteristic quantity DB 201.

In the explanatory diagram illustrated in FIG. 21, the sensor equipment 11 include the processing units, i.e., the sensor wearing determination unit 111, the heart rate data acquiring unit 112, the acceleration data acquiring unit 113, the exercise period determination unit 114, the meal period determination unit 115 and the noise heart rate eliminating unit 116. The sensor equipment 11 further includes the processing units, i.e., the area size characteristic quantity calculation unit 117, the amplitude characteristic quantity calculation unit 118, the speed characteristic quantity calculation unit 119, the time characteristic quantity calculation unit 120 and the data transmission unit 121. The sensor equipment 11 receives allocation of the identification number or other equivalent information for uniquely identifying the wearers of the sensor equipments 11.

[Sensor Equipment]

The sensor wearing determination unit 111 illustrated in FIG. 21 determines a state of wearing the sensor equipment 11, based on a peak interval of electrocardiographic waveforms detected per unit time (e.g., 10 sec). For example, the sensor equipment 11 previously acquires a resting heart rate of the wearer of the sensor equipment 11 specified by the identification number and other equivalent information, and stores the acquired heart rate in the auxiliary storage unit 93. The sensor equipment 11 refers to the resting heart rate stored in the auxiliary storage unit 93, and may determine that the wearing state of the sensor equipment 11 is normal, based on the peak interval of the electrocardiographic waveforms determined per unit time.

The sensor wearing determination unit 111 may determine the wearing state of the sensor equipment 11 from an event that a sensor output for a predetermined period instanced by 10 sec and 1 min is acquired from the acceleration sensor. The sensor wearing determination unit 111 may determine that the wearing state of the acceleration sensor is normal when outputting of a value in the vicinity of "0" as the output value of the acceleration sensor does not continue over the predetermined period. When the wearing state of the sensor equipment 11 is not normal, the sensor wearing determination unit 111 may notify the wearer via the output unit 95 by emission of a sound of alarm, flickering of an LED and other equivalent signaling.

The heart rate data acquiring unit 112 acquires the heart rate detected per unit time, and temporarily stores the acquired heart rate in a predetermined location of the main storage unit 92 by associating the acquired heart rate with time information. The time information contains calendar time of a year, a month, a day, an hour, a minute and other equivalent time information. Note that the heart rate detected per unit tine may be expressed by, e.g., bpm (beats per minute) and other equivalent notations. The acceleration data acquiring unit 113 acquires the accelerations detected per unit tine in the vertical, bilateral and back-and-forth directions, and temporarily stores the acquired acceleration value in a predetermined location of the main storage unit 92 by associating the acquired acceleration value with the time information. The time information contains the calendar time of the year, the month, the day, the hour, the minute and other equivalent time information.

The exercise period determination unit 114 specifies an exercise period of walking, running, going up and down the stairs and other equivalent exercises from time series of the accelerations in the vertical, bilateral and back-and-forth directions, the accelerations being acquired by the acceleration data acquiring unit 113. The exercise period determination unit 114 temporarily stores start time information and end time information related to the specified exercise period in a predetermined location of the main storage unit 92.

Figure 22:
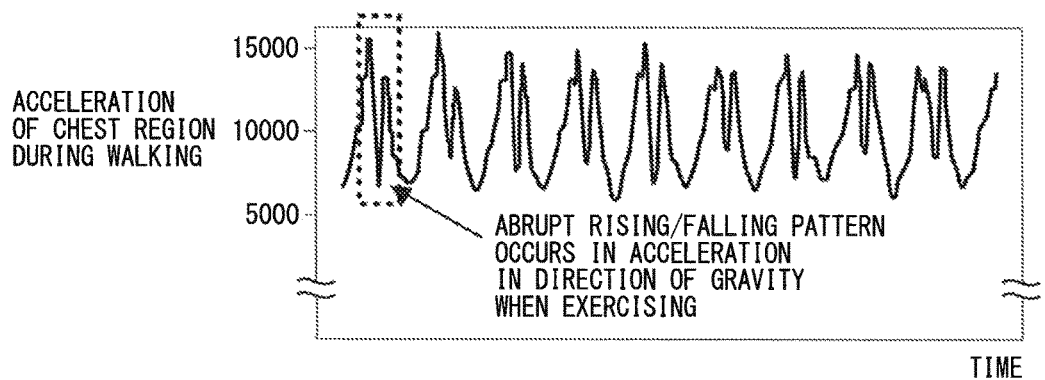
FIG. 22 is an explanatory diagram illustrating a variation of acceleration detected when performing an exercise.

FIG. 22 illustrates an explanatory diagram of a variation of the acceleration in the vertical direction (direction of gravity), the acceleration being detected when exercising. An explanatory diagram illustrated in FIG. 22 is a graph of the variation of the acceleration in the direction of gravity, in which the axis of ordinates indicates the acceleration in the direction of gravity, while the axis of abscissa indicates the elapse time (the period of time) when exercising. Note that the subject person wears the sensor equipment 11 including the sensor to detect the acceleration in the vertical direction, the sensor equipment 11 being attached to a region of chest of the subject person.

In the explanatory diagram of FIG. 22, as indicated in a rectangular area encompassed by a broken line, when performing walking, running, going up and down the stairs and other equivalent exercises, the subject person receives a reactive force from the ground or other equivalent foundations upon legs kicking out while touching the ground, and hence there are detected rapid rising/falling variations of the acceleration value in the vertical direction. Then, as illustrated in FIG. 22, the variations in the vertical direction during an exercise period are periodically detected, these variations being accompanied with the rapid rising/falling variations of the acceleration value.

The exercise period determination unit 114 detects a pattern of the rapid rising/falling variations of the acceleration value about the detected acceleration values in the vertical direction, and specifies the exercise activity of the wearer when the pattern is detected as the time series of the acceleration at an interval of a predetermined period. It may be herein sufficient that the predetermined period is set by experimentally acquiring a cycle of the variations of the acceleration in the vertical direction when the wearer performs the exercise activity in a state of wearing the sensor equipment 11 beforehand, the acceleration variations being accompanied with the rapid rising/falling variations of the acceleration value in association with the exercise activity. Then, the predetermined period may be set from the experimentally acquired cycle of the variations of the acceleration in the vertical direction, the acceleration variations being accompanied with the rapid rising/falling variations of the acceleration value in association with the exercise activity. It may be sufficient that the thus-set predetermined period is stored in the auxiliary storage unit 93 by being associated with, e.g., identifying information of the wearer. The exercise period determination unit 114 may specify the exercise activity of the wearer by referring to, e.g., the set value for the predetermined period, the value being stored in the auxiliary storage unit 93.

The exercise period determination unit 114, when the exercise activity of the wearer is specified, may specify the exercise start time and the exercise end time from, e.g., the time information associated with acceleration value. The exercise period determination unit 114 can specify the exercise period, based on the exercise start time and the exercise end time.

Referring back to the explanatory diagram illustrated in FIG. 21, the meal period determination unit 115 specifies a meal action period associated with the meal of the wearer from the time series of the accelerations in the vertical, bilateral and back-and-forth directions, the accelerations being acquired by the acceleration data acquiring unit 113. The meal period determination unit 115 obtains the meal period by adding, e.g., a fixed period expended for the peristaltic movement explained in FIG. 7 to the specified meal action period. The meal period determination unit 115 temporarily stores, e.g., pieces of information on meal period start time and meal period end time counted from the obtained meal period in a predetermined location of the main storage unit 92.

Figure 23:
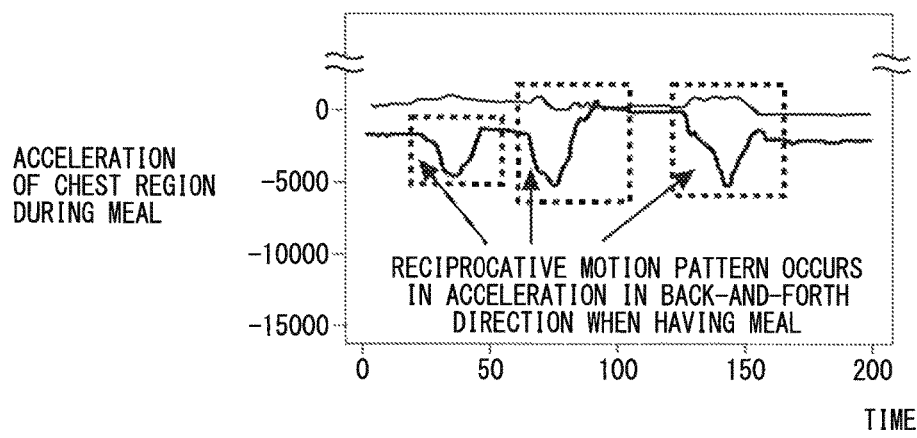
FIG. 23 is an explanatory diagram illustrating a variation of acceleration detected when having the meal.

FIG. 23 illustrates an explanatory diagram of variations, detected when conducting the meal action, of acceleration in the back-and-forth direction. The explanatory diagram illustrated in FIG. 23 is a graph of the variations of the acceleration in the back-and-forth direction, in which the axis of ordinates indicates the acceleration in the back-and-forth direction, while the axis of abscissa indicates the elapse time (the period of time) when conducting the meal action. Note that the subject person wears the sensor equipment 11 including the sensor to detect the acceleration in the back-and-forth direction, the sensor equipment 11 being attached to the region of chest of the subject person.

In the explanatory diagram illustrated in FIG. 23, as indicated in a rectangular area encompassed by a broken line, the meal action involves repeating a motion for taking an acquisition to a region of lip, and consequently there is repeatedly detected such a pattern that the acceleration value in the back-and-forth direction rises after falling, and a post-rising acceleration value continues for a fixed period and again falls.

The meal period determination unit 115 detects a pattern of falling/rising variations of the detected acceleration value in the back-and-forth direction, and specifies the meal action of the wearer when this pattern is detected a predetermined number of times or more within a fixed period of time as the time series of the acceleration. Herein, the fixed period of time is a period expended for the meal and can be exemplified by a period of time, e.g., 10 through 30 minutes. Further, the predetermined number of times may involve setting an experimentally acquired number of detections with repetition of a pattern of the falling/rising variations associated with the meal action conducted by the wearer in the state of wearing the sensor equipment 11 beforehand. The predetermined number of times may be set from the experimentally acquired number of detections. The predetermined number of times being thus set may be stored in the auxiliary storage unit 93 by being associated with, e.g., the identifying information of the wearer. The meal period determination unit 115 may specify the meal action of the wearer by referring to, e.g., a set value of the predetermined number of times, which is stored in the auxiliary storage unit 93.

The meal period determination unit 115 may specify, when the meal action of the wearer is specified, the meal action start time and the meal action end time from the time information associated with, e.g., the acceleration value. The meal period determination unit 115 can specify the meal period based on the meal action start time, the meal action end time and the fixed period of time expended for the peristaltic movement.

Referring back to the explanatory diagram illustrated in FIG. 21, the noise heart rate eliminating unit 116 specifies a rising variation of the heart rate pertaining to the kinetic activity that affects the time-series variations of the detected heart rate, noise variations of the heart rate, which are occur randomly during the meal period and the postprandial period. The noise heart rate eliminating unit 116 eliminates heart rate data detected in relation to the specified rising variations of the heart rate pertaining to the kinetic activity, and the noise variations or other equivalent variations of the heart rate, which occur randomly during the meal period and the postprandial period from the time series of the heart rate acquired by the heart rate data acquiring unit 112.

Figure 24:
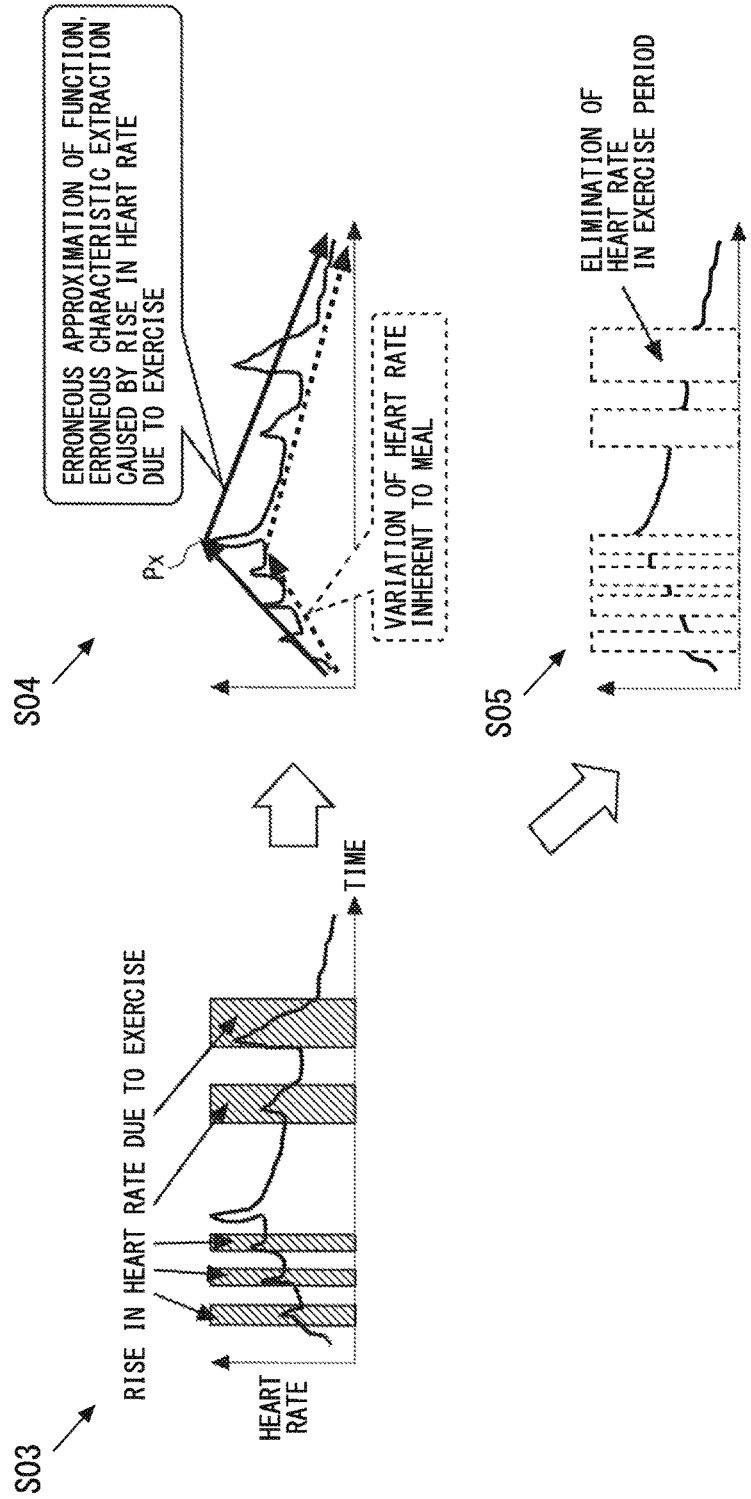
FIG. 24 is an explanatory diagram illustrating a rising variation of the heart rate pertaining to the exercise.

S03-S05 in FIG. 24 illustrate explanatory diagrams of the rising variations of the heart rate due to the exercise. The explanatory diagrams illustrated in S03-S05 of FIG. 24 are graphs of the variations of the heart rate, in which the axis of ordinates indicates the heart rate per unit time, while the axis of abscissa indicates the elapse time (the period of time) including the meal time and the postprandial period.

As indicated in a rectangular area of a right upward oblique line in S03 of FIG. 24, in a transition of the heart rate to be acquired in time series, there are detected the rising variation of the heart rate and a restoration variation of the rising heart rate due to the time elapse during the exercise period. Therefore, with respect to a long-term transition of the heart rate associated with the digestive activity during, e.g., the postprandial period, this results in detecting the rising/restoration variations of the heart rate due to the exercise in superposition on the transition of the heart rate. It is assumed that characteristics of the variations, associated with the meal, of the heart rate does not be grasped from the characteristic quantity of the heartbeats associated with the meal when the variations of the heart rate related to the exercise are superposed because of detecting variations of transition of the heart rate acquired over a long period of time.

In the explanatory diagram illustrated in S04 of FIG. 24, a transition variation of the heart rate indicated by a broken line with an arrow represents a transition not accompanied with the rising/restoration variation of the heart rate related to the exercise. For example, the transition accompanied with the rising/restoration variation of the heart rate related to the exercise results in detecting a heart rate overlapped with the heart rate corresponding to the rising/restoration variation related to the exercise with respect to the transition variation of the heart rate indicated by the broken line with the arrow. This likely leads to a false detection of the characteristic quantities of the amplitude, the response speed (the rising response speed, the restoration response speed) and the response time (the rising response time, the restoration response time) about, e.g., the second peak.

It is assumed that a heart rate value of, e.g., Px is to be detected as the amplitude (the maximum heart rate) about the second peak in S04 of FIG. 24. As indicated by a solid line with an arrow, it is also assumed that the response speed (the rising response speed, the restoration response speed) and the response time (the rising response time, the restoration response time) about the second peak are detected based on the transition variation of the heart rate overlapped with the rising/restoration variation of the heart rate related to the exercise.

For preventing the overlap of the rising/restoration variation of the heart rate related to the exercise, the noise heart rate eliminating unit 116 specifies, e.g., the exercise period and eliminates the heart rate data associated with the time information of the exercise period. The noise heart rate eliminating unit 116 specifies the exercise period based on exercise start time and exercise end time, the exercise period being (originally) specified by the exercise period determination unit 114. The noise heart rate eliminating unit 116 calculates an elimination period related to the exercise by adding a fixed period till the heart rate rising due to the exercise is restored since, e.g., the exercise end time to the exercise end time. Herein, the fixed period till the heart rate rising due to the exercise is restored since the exercise end time can be exemplified by an experimentally acquired period of time. The fixed period may involve setting minutes, e.g., 5 minutes and 10 minutes as a time unit in common among all of the subject persons from whom the heart rates associated with the meals are acquired.

The noise heart rate eliminating unit 116 eliminates the heart rate data, based on the time information corresponding to the elimination period, from the heart rate data associated with the meal, which is acquired by the heart rate data acquiring unit 112. S05 of FIG. 24 depicts such an example of graph that the heart rate corresponding to the elimination period is elimination from the heart rate data illustrated in S03 of FIG. 24. A rectangular area encompassed by a broken line in S05 of FIG. 24 represents the elimination period. In the example of graph of S05 of FIG. 24, a transition of the heart rate associated with the meal does not include the rising/restoration variation of the heart rate due to the exercise, which is detected in superposition on the transition of the heart rate associated with the meal, the heart rate being acquired for the elimination period. It is therefore feasible to detect the characteristic quantity of the heart rate variation associated with the meal without being affected by the rising/restoration variation of the heart rate due to, e.g., the exercise. The noise heart rate eliminating unit 116 temporarily stores, in a predetermined location of the main storage unit 92, the heart rate data from which the heart rate data corresponding to the elimination period is eliminated.

Note that the time-series variation of the heart rate associated with the meal tends to, as indicated by the broken line with the arrow in S04 of FIG. 24, transition along a relative lower limit of the detected heart rate. Consequently, the heart rate values being anterior and posterior in time series are compared with each other, there is grasped such variation points that a differential value between the anterior heart rate value and the posterior heart rate value becomes equal to or larger or smaller than a predetermined threshold value, and an interval specified by this variation points may also be set as the elimination period.

Figure 25:
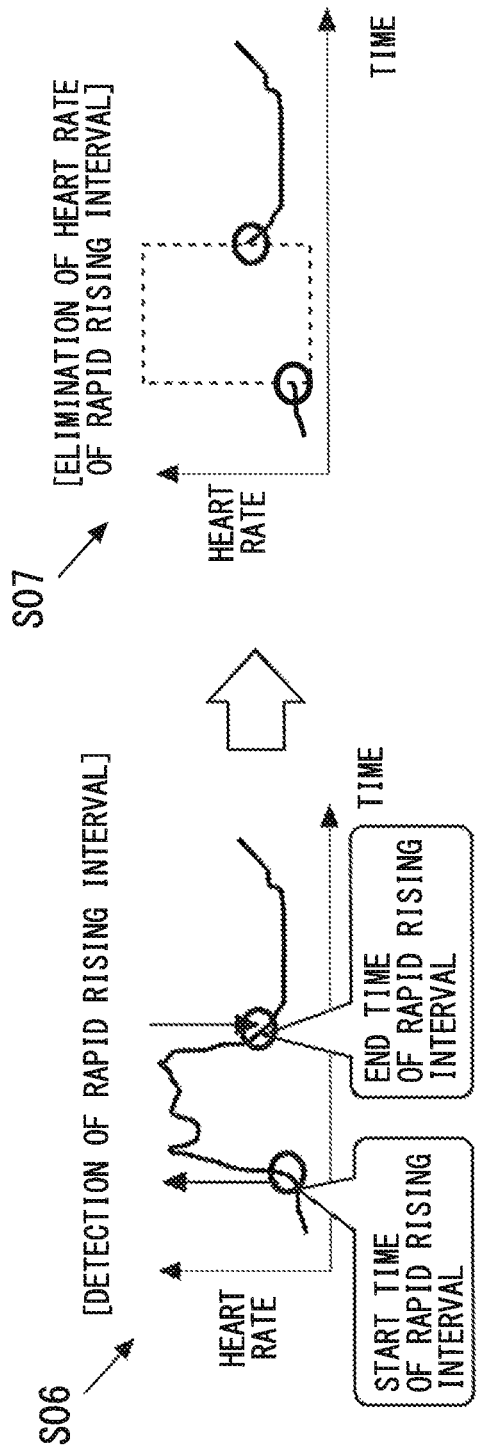
FIG. 25 is an explanatory diagram illustrating an elimination period of the heart rate.

S06 and S07 in FIG. 25 illustrate explanatory diagrams of the elimination period based on the variation points. The explanatory diagrams of S06 and S07 in FIG. 25 illustrate graphs of the variations of the heart rate, in which the axis of ordinates indicates the heart rate per unit time, while the axis of abscissa indicates transition time of the heart rate. In the explanatory diagram of S06 of FIG. 25, rapid rising/falling variation points of the heart rate transitioning in time series are indicated in areas encircled by solid lines.

The noise heart rate eliminating unit 116 compares, e.g., the anterior and posterior heart rate values in time series with each other, and specifies such variation points that the differential value between the anterior heart rate value and the posterior heart rate value becomes equal to or larger or smaller than the predetermined threshold value. The noise heart rate eliminating unit 116 allocates, e.g., the identification numbers to the specified variation points, the identification numbers each uniquely identifying the variation point. The noise heart rate eliminating unit 116 temporarily stores, in a predetermined location of the main storage unit 92, the identification number allocated to the variation point by being associated with the heart rate value being anterior in time series and the time information when detecting the anterior heart rate value when the differential value between the anterior and posterior heart rate values becomes equal to or larger than the predetermined threshold value. Further, the noise heart rate eliminating unit 116 temporarily stores, in the predetermined area of the main storage unit 92, the identification number allocated to the variation point by being associated with the heart rate value being posterior in time series and the time information when detecting the posterior heart rate value when the differential value between the anterior and posterior heart rate values becomes equal to or smaller than the predetermined threshold value.

The noise heart rate eliminating unit 116 specified the elimination period from the time information associated with the variation point at which the differential value between the anterior and posterior heart rate values becomes equal to or larger than the predetermined threshold value, and from the time information associated with the variation point at which the differential value between the anterior and posterior heart rate values becomes equal to or smaller than the predetermined threshold value. Note that such a case is assumed that the variation point at which the differential value between the heart rate values becomes equal to or larger than the predetermined value, is consecutively detected in time series. In the consecutive case of the variation points at which the differential value between the heart rate values becomes equal to or larger than the predetermined threshold value in time series, for example, the variation point with the heart rate value being anterior in time series or the variation point with the lower (smaller) heart rate value associated with the variation point, may be set as the start time of the elimination period. Similarly, in such a case that the variation point at which the differential value between the heart rate values becomes equal to smaller than the predetermined threshold value is consecutively detected in time series, for example, the variation point with the heart rate value being posterior in time series or the variation point with the lower (smaller) heart rate value associated with the variation point, may be set as the end time of the elimination period.

S07 of FIG. 25 illustrates an example of graph, in which the heart rate corresponding to the elimination period is eliminated from the heart rate data depicted in S06 of FIG. 25.

A rectangular area encompassed by a broken line in S07 of FIG. 25 represents the elimination period. The example of graph of S07 of FIG. 25 does not include the heart rate values acquired in the elimination period. It is therefore possible to detect the characteristic quantities of the heart rate variation associated with the meal without being affected by the rising/restoration variation of the heart rate in, e.g., elimination period. For example, it is feasible to eliminate the heart rate data like a noise instanced by the rising/restoration variation of the heart rate, which occurs randomly during the meal period and the postprandial period.

Referring back to FIG. 21, the area size characteristic quantity calculation unit 117 calculates an area size ratio between the first peak area and the second peak area as, e.g., a characteristic quantity R1 of the heartbeats associated with the meal. The area size characteristic quantity calculation unit 117 calculates the characteristic quantity R1 targeting on the heart rate data obtained by the noise heart rate eliminating unit 116 eliminating, e.g., an amount of variation of the heart rate with respect to the exercise period and other equivalent periods from the heart rate data acquired by the heart rate data acquiring unit 112. Note that the calculation of the area size ratio between the first peak area and the second peak area as the characteristic quantity R1 of the heartbeats associated with the meal, has been already described in FIG. 7.

The area size characteristic quantity calculation unit 117 temporarily stores, in a predetermined location of the main storage unit 92, the calculated area size ratio between the first peak area and the second peak area in association with a time zone of the meal. The time zone of the meal can be exemplified by the four time zones, i.e., the breakfast (5:00-1:00), the lunch (11:00-17:00), the supper (17:00-24:00) and the late night snack (24:00-5:00).

The amplitude characteristic quantity calculation unit 118 calculates, e.g., a first peak amplitude (maximum heart rate P1) and a second peak amplitude (maximum heart rate P2) as a characteristic quantity (2) of the heartbeats associated with the meal. The amplitude characteristic quantity calculation unit 118 calculates the characteristic quantity (2) targeting on the heart rate data obtained by the noise heart rate eliminating unit 116 eliminating, e.g., an amount of variation of the heart rate with respect to the exercise period and other equivalent periods from the heart rate data acquired by the heart rate data acquiring unit 112. Note that the calculation of the first and second peak amplitudes as the characteristic quantity (2) of the heartbeats associated with the meal, has been already described in FIG. 8. The amplitude characteristic quantity calculation unit 118 temporarily stores, in a predetermined location of the main storage unit 92, the calculated first and second amplitudes in association with the time zone of the meal.

The speed characteristic quantity calculation unit 119 calculates, e.g., the response speed (the rising response speed, the restoration response speed) of the first peak and response speed (the rising response speed, the restoration response speed) of the second peak as a characteristic quantity R3 of the heartbeats associated with the meal. The speed characteristic quantity calculation unit 119 calculates the characteristic quantity R3 targeting on the heart rate data obtained by the noise heart rate eliminating unit 116 eliminating, e.g., an amount of variation of the heart rate with respect to the exercise period and other equivalent periods from the heart rate data acquired by the heart rate data acquiring unit 112. Note that the calculation of the response speeds of the first and second peaks as the characteristic quantity R3 of the heartbeats associated with the meal, has been already described in FIGS. 9-12. The speed characteristic quantity calculation unit 119 temporarily stores, in a predetermined location of the main storage unit 92, the calculated response speeds of the first and second peaks in association with the time zone of the meal.

The time characteristic quantity calculation unit 120 calculates, e.g., the response time (the rising response time, the restoration response time) of the first peak and response time (the rising response time, the restoration response time) of the second peak as a characteristic quantity R4 of the heartbeats associated with the meal. The time characteristic quantity calculation unit 120 calculates the characteristic quantity R4 targeting on the heart rate data obtained by the noise heart rate eliminating unit 116 eliminating, e.g., an amount of variation of the heart rate with respect to the exercise period and other equivalent periods from the heart rate data acquired by the heart rate data acquiring unit 112. Note that the calculation of the response time of the first and the response time of the second peaks as the characteristic quantity R4 of the heartbeats associated with the meal has been already described in FIGS. 13-14. The time characteristic quantity calculation unit 120 temporarily stores, in a predetermined location of the main storage unit 92, the calculated response time of the first and the calculated response time of the second peaks in association with the time zone of the meal.

The data transmission unit 121 outputs, to the network N, the characteristic quantities R1-R4 calculated by the area size characteristic quantity calculation unit 117, the amplitude characteristic quantity calculation unit 118, the speed characteristic quantity calculation unit 119 and the time characteristic quantity calculation unit 120. The calculated characteristic quantities R1-R4 are output to the network N by associating these quantities with the identification number allocated to the wearers of the sensor equipments 11 and the time zone of the meal.

Note that the data transmission unit 121 may also register the eleven characteristic quantities of four categories, i.e., the calculated characteristic quantities R1-R4 in, e.g., records of the table illustrated in FIG. 15, which are associated with the respective characteristic quantities, and may thus output this table to the network N.

FIG. 26 illustrates an example of a meal characteristic quantity table having registered the eleven characteristic quantities of four categories related to the meal. The data transmission unit 121 registers the calculated eleven characteristic quantities of four categories in (four) "calculation result" fields associated with the four categories of characteristic quantities, thus generating the meal characteristic quantity table. Note that the meal characteristic quantity table illustrated in FIG. 26 may contain the identification number associated with the wearers of the sensor equipments 11 beforehand. The meal characteristic quantity table illustrated in FIG. 26 may also contain a field corresponding to the time zone of the meal. The data transmission unit 121 registers the identification number of the sensor equipment 11 and the time zone of the meal in the generated meal characteristic quantity table, and outputs the meal characteristic quantity table to the network N.

[Information Processing Apparatus]

The data reception unit 101 illustrated in FIG. 21 accepts the meal characteristic quantity table depicted in FIG. 26, which has been output to the network N from the sensor equipment 11. The accepted meal characteristic quantity table contains, e.g., the identification number associated with the wearers of the sensor equipments 11, the time zones of the meals at which the respective characteristic quantities are acquired, and other equivalent information. The data reception unit 101 temporarily stores the accepted meal characteristic quantity table in a predetermined location of the main storage unit 92.

The DB information acquiring unit 102 acquires the characteristic quantities associated with meal of every candidate registered beforehand by referring to, e.g., a meal characteristic quantity DB 201. The meal characteristic quantity DB 201 stores the meal characteristic quantity table (FIG. 15) per time zone of the meal as an actual result acquired from every candidate. The DB information acquiring unit 102 searches the meal characteristic quantity DB 201 for acquiring the characteristic quantity per candidate, which is coincident with the time zone of the meal, on the basis of the meal time zones registered in the meal characteristic quantity table accepted by the data reception unit 101. The DB information acquiring unit 102 temporarily stores, in a predetermined location of the main storage unit 92, the characteristic quantity per candidate, which is coincident with the time zone of the meal, the characteristic quantity being acquired from the meal characteristic quantity DB 201.

The DB information acquiring unit 102, when the meal characteristic quantity table accepted by the data reception unit 101 is of a true wearer of the sensor equipment 11, associates the meal characteristic quantity table with the true wearer and stores this table in the meal characteristic quantity DB 201. The DB information acquiring unit 102 updates the meal characteristic quantity DB 201, based on, e.g., the identification number of the sensor equipment and the time zone of the meal.

The candidate unique range generating unit 103 generates a unique range of each characteristic quantity about each candidate, based on the data of the characteristic quantities related to the meal of every candidate, the characteristic quantities being acquired from the meal characteristic quantity DB 201. The unique range of the characteristic quantity is generated by obtaining, e.g., the maximum value and the minimum value of the characteristic quantities. However, the unique range may entail using a 3σ range as broad as a standard deviation (σ) of the characteristic quantities in place of the maximum value and the minimum value. When calculating the unique range of each characteristic quantity detected per candidate, for example, an irregular abnormal value (e.g., a detection value derived from incorrectly wearing the sensor equipment 11, and other equivalent causes) can be eliminated.

The candidate unique range generating unit 103 compares the acquired data in magnitude per characteristic quantity in the eleven characteristic quantities of four categories of every candidate, and specifies the maximum value and the minimum value of the target characteristic quantities. The candidate unique range generating unit 103 temporarily stores, in a predetermined location of the main storage unit 92, the maximum value and the minimum value of every specified characteristic quantity by being associated with the candidate from whom the data are acquired.

The subject person narrowing unit 104 narrows down the wearer of the sensor equipment 11, based on the unique range of each of the eleven characteristic quantities of four categories per candidate, the unique range being generated by the candidate unique range generating unit 103. The subject person narrowing unit 104 determines whether each of the eleven characteristic quantities of four categories accepted from the sensor equipment 11 falls within the unique range of each candidate per characteristic quantity. The determination as to whether the characteristic quantity accepted from the sensor equipment 11 falls within the unique range of each candidate is made per candidate. Further, the determination about whether included in the unique range of the candidate is made based on the maximum value and the minimum value of the unique range and a magnitude relation of the characteristic quantity data accepted from the sensor equipment 11.

The subject person narrowing unit 104, when the characteristic quantities accepted from the sensor equipments 11 fall within the unique ranges of the characteristic quantities about the respective candidates, extracts all of the relevant candidates who may be deemed as the wearers (subject persons) of the sensor equipments 11. The subject person narrowing unit 104 temporarily stores, in a predetermined location of the main storage unit 92, all of the extracted candidates by being associated with the identification numbers of the sensor equipments 11.

The result display unit 105 outputs the candidates extracted by the subject person narrowing unit 104 to the output unit 95 of the information processing apparatus 10, the candidates being associated with the identification numbers or other equivalent information of the sensor equipments 11. For example, the result display unit 105 displays the candidates extracted by the subject person narrowing unit 104 on a display screen of a CRT (Cathode Ray Tube) and other equivalent displays by being associated with the identification numbers of the sensor equipments 11, and other equivalent information.

Note that the extracted candidates may be displayed in any arbitrary display mode. For example, the arbitrary display mode can be exemplified by a display mode based on a table format in which names of the processing target candidates are associated with the identification numbers of the sensor equipments 11. Another arbitrary display mode may be such that the names of the extracted candidates and the identification numbers of the sensor equipments 11 are registered in a message prepared as a template beforehand, and this message is displayed on the display screen of the CRT and other equivalent displays to inform of erroneous wearing of the sensor equipment 11.

For example, an administrator or another equivalent person of the information processing system 1 can check wearing states of the sensor equipments 11 of the patients with occurrence of mis-wearing, based on the information displayed on the display screen of the CRT and other equivalent displays of the information processing apparatus 10. Further, the administrator or another equivalent person may accumulate the acquired characteristic quantity tables as update information when determining that the subject person wearing the sensor equipment 11 is the true wearer, based on the information displayed on the display screen of the CRT and other equivalent displays of the information processing apparatus 10. For example, the information processing apparatus 10 can store, in the meal characteristic quantity DB 201, the acquired characteristic quantity tables as the update information of the true wearers in accordance with an operation input accepted via the input unit 94 instanced by the keyboard and other equivalent devices. The characteristic quantity tables are stored in the meal characteristic quantity DB 201 via, e.g., the DB information acquiring unit 102.

[Processing Flow]
(Whole Processing)

Figure 27:
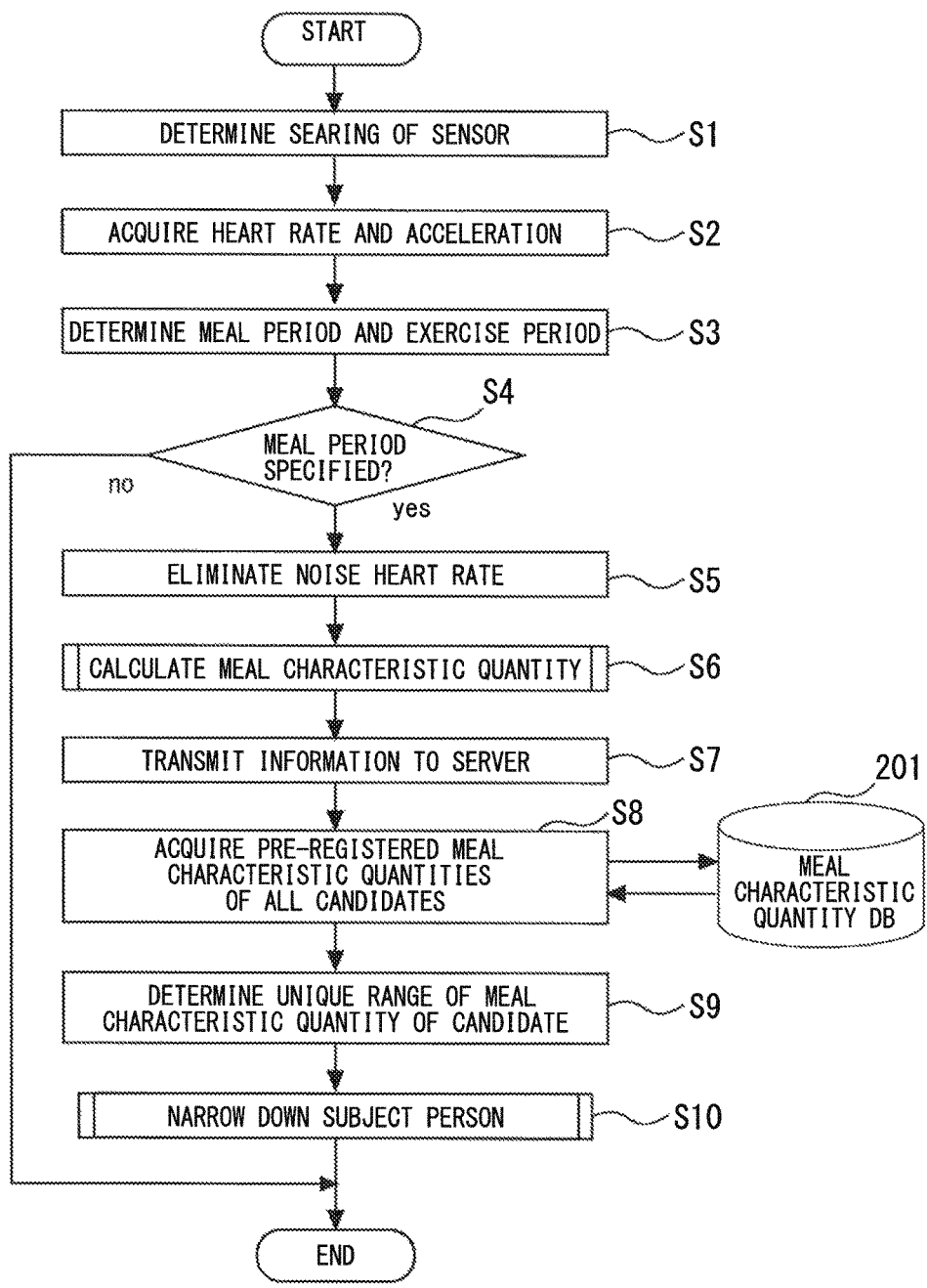
FIG. 27 is a flowchart of a whole subject person specifying process.

A subject person specifying process of the information processing system 1 in the embodiment will hereinafter be described with reference to the drawings illustrated in FIGS. 27-56. FIG. 27 illustrates a flowchart related to a whole of the subject person specifying process. In the flowchart illustrated in FIG. 27, the sensor equipment 11 depicted in FIG. 19 executes processes in S1-S7, and the information processing apparatus 10 executes processes in S8-S10.

It is to be noted that the subject person specifying process illustrated in FIG. 27 is not limited to the embodiment. For example, a configuration may be such that the respective sensor equipments 11 are connected to the meal characteristic quantity DB 201 via the network N, and each sensor equipment 11 executes the subject person specifying process in S1-S10. The sensor equipment 11 is connected to the meal characteristic quantity DB 201 via the network N and executes the subject person specifying process, in which case the process in, e.g., S7 illustrated in FIG. 27 may be skipped. Another available configuration is that the sensor equipment 11 is integrally configured to include the meal characteristic quantity DB 201. When the sensor equipment 11 includes the meal characteristic quantity DB 201, for example, in addition to skipping the process in S7, the subject person specifying process can be started and ended within the sensor equipment 11 without depending on a status of the meal characteristic quantity DB 201 connected thereto.

In the flowchart illustrated in FIG. 27, a timing for starting the subject person specifying process can be exemplified by detecting the heart rate corresponding to the time zone of the meal after, e.g., wearing the sensor equipment 11. The sensor equipment 11 determines a wearing state of the sensor equipment 11, based on a peak interval of the electrocardiographic waveforms detected per unit time (e.g., 10 sec) of the wearer. The sensor equipment 11 determines the wearing state of the sensor equipment 11 from an event that the acceleration value does not keep holding a value in the vicinity of "0" within a predetermined period instanced by 10 sec and 1 minute (S1). Incidentally, the determination about wearing the sensor has already been described in FIG. 21.

The sensor equipment 11 acquires the heart rates detected per unit time and the accelerations detected per unit time in the vertical, bilateral and back-and-forth directions (S2). The sensor equipment 11 temporarily stores, in a predetermined location of the main storage unit 92, the acquired heart rates and the accelerations in the vertical, bilateral and back-and-forth directions by being associated with, e.g., the time information. The time information contains the calendar time of the year, the month, the day, the hour, the minute and other equivalent time information. The main storage unit 92 accumulates the acquired heart rates and the accelerations in the vertical, bilateral and back-and-forth directions in time series. Incidentally, the acquisition of the heart rates and the acquisition of the accelerations in the vertical, bilateral and back-and-forth directions have already been described in FIG. 21.

The sensor equipment 11 specifies the meal period and the exercise period of the wearer from the acceleration in the back-and-forth direction and the acceleration in the vertical direction, which are acquired in the process of S2 (S3). The sensor equipment 11 temporarily stores the start time information and the end time information about the specified meal period in a predetermined location of the main storage unit 92. Similarly, the sensor equipment 11 temporarily stores the start time information and the end time information about the specified exercise period in a predetermined location of the main storage unit 92. Incidentally, the description of how the meal period and the exercise period are specified has already been made in FIGS. 22 and 23.

In the process of S4, the sensor equipment 11 determines whether the time-series heart rate data acquired in the process of S2 contain the meal period specified in the process of S3. For example, a case of not taking the meal even in the time zone (5:00-11:00) to take the breakfast, is assumed due to a habit of the wearer or for a reason of having no appetite. This is because the heart rate peak derived from the peristaltic movement and the digestive activity does not occur in the case of not taking the meal, and hence it is difficult to detect the eleven characteristic quantities of four categories of the heartbeats associated with the meals.

The sensor equipment 11 finishes the subject person specifying process in progress when the time-series heart rate data acquired in the process of S2 do not contain the meal period specified in the process of S3 (S4, no). Whereas when the time-series heart rate data acquired in the process of S2 contain the meal period specified in the process of S3 (S4, yes), the sensor equipment 11 shifts to S5 and continues the subject person specifying process in progress.

In the process of S5, the sensor equipment 11 eliminates the rapid rising/restoration variation of the heart rate to be superposed on the transition of the heart rate associated with the meal from the time-series heart rate data acquired in the process of S2. The sensor equipment 11 temporarily stores, in a predetermined location of the main storage unit 92, the heart rate data obtained by eliminating the rapid rising/restoration variation of the heart rate to be superposed on the transition of the heart rate associated with the meal from the time-series heart rate data acquired in the process of S2. Incidentally, the elimination of the noise heart rate has already been described in S03-S05 in FIG. 24 and S06-S07 in FIG. 25.

In the process of S6, the sensor equipment 11 calculates the eleven characteristic quantities of four categories (meal characteristic quantities) about the heart rates associated with the meals. The sensor equipment 11 calculates the eleven meal characteristic quantities of four categories, based on the heart rate data obtained by eliminating the rapid rising/restoration variation of the heart rate to be superposed on the transition of the heart rate associated with the meal in the process of S5. The sensor equipment 11 temporarily stores, in a predetermined location of the main storage unit 92, the calculated eleven meal characteristic quantities of four categories by being associated with the time zones of the meals and the identifying information of the sensor equipment 11. Note that the process of calculating the meal characteristic quantities in S6 will be described in FIGS. 28-32.

The sensor equipment 11 outputs the eleven meal characteristic quantities of four categories about the heart rates associated with the meals, which are calculated in the process of S6, to the network N (S7). The information processing apparatus 10 accepts the eleven meal characteristic quantities of four categories that are output to the network N. Incidentally, the process in S7 has already been described in FIG. 26.

In the process of S8, the information processing apparatus 10 accepts the eleven meal characteristic quantities of four categories associated with the meals of the wearer from the sensor equipment 11, the characteristic quantities having been output to the network N. The meal characteristic quantities contain, e.g., the time zones of the meals and the identifying information of the sensor equipment 11. The information processing apparatus 10 temporarily stores, in a predetermined location of the main storage unit 92, the accepted eleven meal characteristic quantities of four categories associated with the meals by being associated with the time zones of the meals and the identifying information of the sensor equipment 11.

As triggered by accepting the eleven meal characteristic quantities of four categories output from the sensor equipment 11, the information processing apparatus 10 acquires the meal characteristic quantities associated with the meals of every candidate registered beforehand by referring to the meal characteristic quantity DB 201. The information processing apparatus 10 searches the meal characteristic quantity DB 201, based on the meal time zones of the accepted meal characteristic quantities, and thus acquires the meal characteristic quantities of every candidate, which are matched with the time zones of the meals. The information processing apparatus 10 temporarily stores, in a predetermined location of the main storage unit 92, the characteristic quantities of every candidate, which are acquired from the meal characteristic quantity DB 201 and matched with the meal time zones.

In the process of S9, the information processing apparatus 10 compares the acquired data in magnitude per characteristic quantity with respect to the eleven characteristic quantities of four categories per candidate, which are acquired in the process of S8, thereby specifying the maximum value and the minimum value of the target characteristic quantities as the unique range. The information processing apparatus 10 temporarily stores, in a predetermined location of the main storage unit 92, the unique range (the maximum value, the minimum value) per specified characteristic quantity by being associated with the candidate from whom the meal characteristic quantities are acquired.

In the process of S10, the information processing apparatus 10 narrows down the wearer (subject person) of the sensor equipment 11 accepted in the process of S8, based on the unique range of the meal characteristic quantities per candidate, which are specified in the process of S9. Note that a subject person narrowing process in S10 will be described in FIG. 33.

The information processing apparatus 10, when the unique range of the meal characteristic quantities about each candidate embraces the meal characteristic quantities accepted from the sensor equipment 11, extracts all of the relevant candidates deemed as the wearers (subject persons) of the sensor equipments 11. The information processing apparatus 10 temporarily stores all of the extracted candidates in a predetermined location of the main storage unit 92 by being associated with the identification numbers of the sensor equipments 11.

The information processing apparatus 10 displays all of the candidates extracted in the process of S10 on the display screen of the CRT or other equivalent displays of the output unit 95 of the information processing apparatus 10 by being associated with the identification numbers and other equivalent information of the sensor equipments 11.

Herein, the processes in S1-S6 executed by the information processing apparatus 10 or the sensor equipment 11 are one example of acquiring characteristic quantities of variations of a heart rate pertaining to a meal of a subject person from heart rate data of the subject person defined as a target person of a process of specifying an individual. Further, the information processing apparatus 10 or the CPU 11 and other equivalent units of the sensor equipment 11 execute the processes in S1-S6 as one example of a unit to acquire characteristic quantities of variations of a heart rate pertaining to a meal of a subject person from heart rate data of the subject person defined as a target person of a process of specifying an individual.

The processes in S8-S9 executed by the information processing apparatus 10 or the sensor equipment 11 are one example of calculating a distribution range of history values of characteristic quantities associated with a plurality of candidates. Further, the information processing apparatus 10 or the CPU 11 and other equivalent units of the sensor equipment 11 execute the processes in S8-S9 as one example of calculating a distribution range of history values of characteristic quantities associated with a plurality of candidates.

The process in S10 executed by the information processing apparatus 10 or the sensor equipment 11 is one example of extracting a candidate corresponding to a subject person from within the plurality of candidates, based on a relation between the characteristic quantities acquired from the subject person and the distribution range of the history values of the characteristic quantities. Moreover, the information processing apparatus 10 or the CPU 11 and other equivalent units of the sensor equipment 11 execute the process in S10 one example of a unit to extract a candidate corresponding to a subject person from within the plurality of candidates, based on a relation between the characteristic quantities acquired from the subject person and the distribution range of the history values of the characteristic quantities.

(Calculation Process of Meal Characteristic Quantities)

A calculation process of the meal characteristic quantities in S3 illustrated in FIG. 27 will be described with reference to flowcharts depicted in FIGS. 28-32. The calculation process of the meal characteristic quantities illustrated in FIGS. 28-32 involve calculating the eleven meal characteristic quantities of four categories about the heart rates pertaining to the meals of the wearer of the sensor equipment 11.

Figure 28:
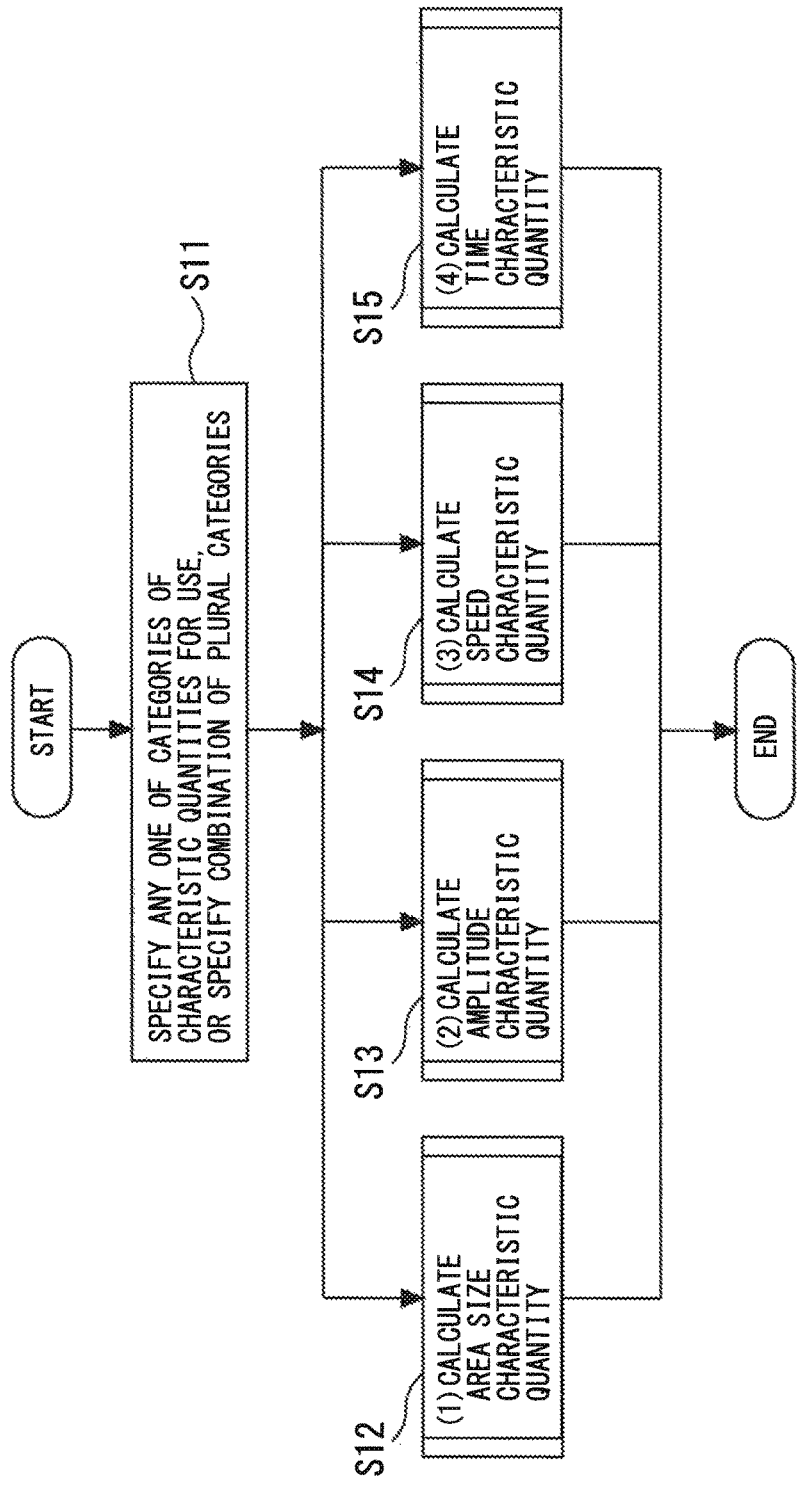
FIG. 28 is a flowchart of a process of calculating meal characteristic quantities in S3 of FIG. 27.

In the flowchart illustrated in FIG. 28, in the process of S11, the sensor equipment 11 determines a category of meal characteristic quantity to be processed within the eleven meal characteristic quantities of four categories. For example, the sensor equipment 11 determined the meal characteristic quantity as a processing target in accordance with the category of the meal characteristic quantity to be preset in the auxiliary storage unit 93 and other equivalent storages. The meal characteristic quantity to be preset may be set as anyone of the eleven meal characteristic quantities of four categories, and may also be set a combination of plural meal characteristic quantities (eleven quantities at the maximum) in the eleven meal characteristic quantities of four categories.

The sensor equipment 11 selects and executes the processes in S12-S14 in accordance with the category of the meal characteristic quantity determined in the process of S11. Note that the area size ratio between the first peak area and the second peak area is calculated as the characteristic quantity R1 of the heartbeats pertaining to the meal in the process in S12. The first peak amplitude (the maximum heart rate P1) and the second peak amplitude (the maximum heart rate P2) are calculated as the characteristic quantity (2) of the heartbeats pertaining to the meal in the process in S13. The response speed (the rising response speed, the restoration response speed) of the first peak and the response speed (the rising response speed, the restoration response speed) of the second peak are calculated as the characteristic quantity R3 of the heartbeats pertaining to the meal in the process in S14. The response time (the rising response time, the restoration response time) of the first peak and the response time (the rising response time, the restoration response time) of the second peak are calculated as the characteristic quantity R4 of the heartbeats pertaining to the meal in the process in S15.

For example, the area size ratio between the first peak area and the second peak area, and the restoration response speed of the second peak and the restoration response time of the second peak are set as the categories of the meal characteristic quantities to be processed, in which case the processes in S12, S14, S15 are selected. The sensor equipment 11 may calculate three sets of meal characteristic quantities by executing the processes in S12, S14, S15 in accordance with the categories of the meal characteristic quantities being set. Note that the process in S12 will be explained with reference to a flowchart in FIG. 29; the process in S13 will be explained with reference to a flowchart in FIG. 30; the process in S14 will be explained with reference to a flowchart in FIG. 31; and the process in S15 will be explained with reference to a flowchart in FIG. 32.

(Calculation of Area Size Characteristic Quantity)

Figure 29:
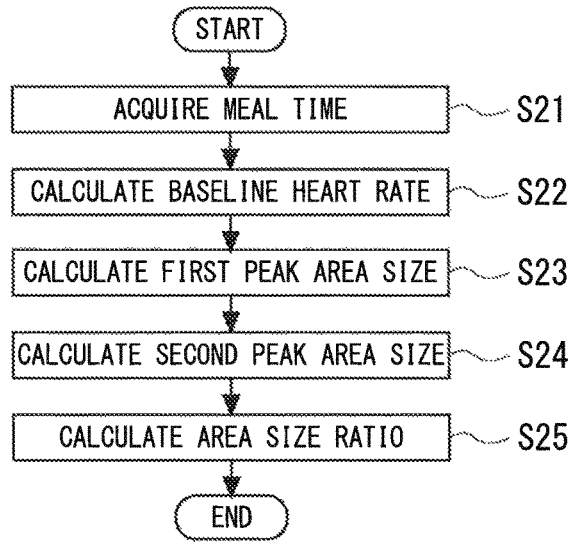
FIG. 29 is a flowchart of a process of calculating area size characteristic quantities in S12 of FIG. 28.

In the flowchart illustrated in FIG. 29, the sensor equipment 11 in the process of S21 acquires the meal period specified in the process of S2 in FIG. 27. The sensor equipment 11 calculates a baseline heart rate based on the meal period acquired in the process of S2 (S22). The sensor equipment 11 temporarily stores, in a predetermined location of the main storage unit 92, the baseline heart rate calculated in the process of S22 by being associated with the time zone of the meal and the identification number of the sensor equipment.

Figure 36:
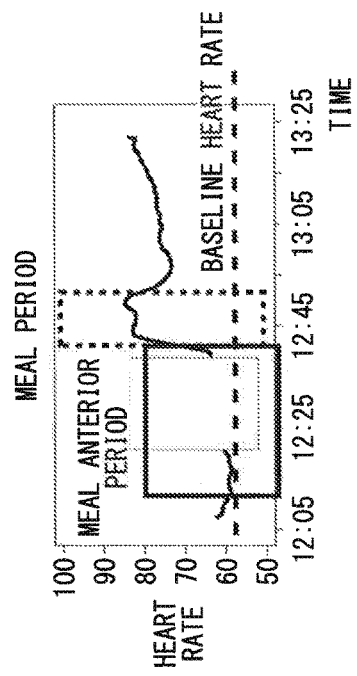
FIG. 36 is an explanatory diagram of a correlation between the meal anterior period, the meal period and the baseline heart rate.
Figure 35:
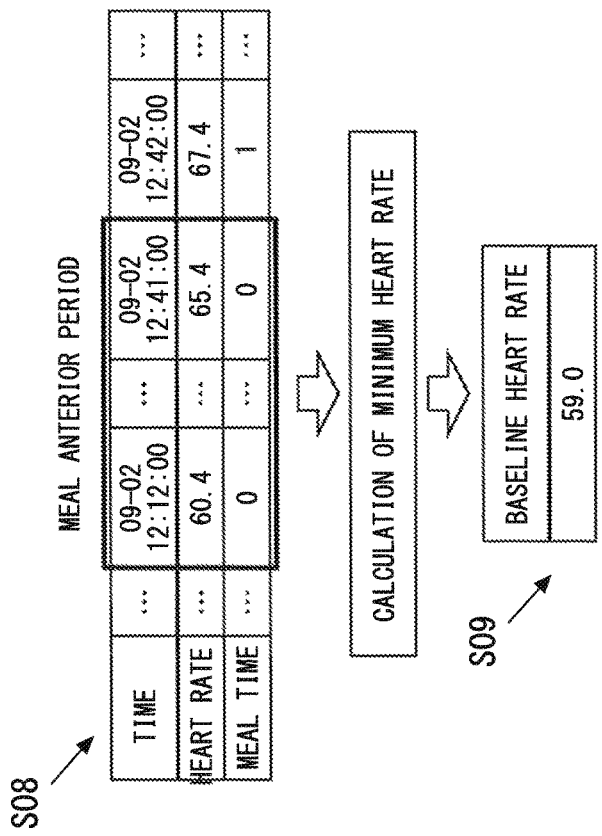
FIG. 35 is an explanatory diagram of a baseline heart rate.

FIGS. 35 and 36 illustrate explanatory diagrams of the baseline heart rate. The explanatory diagram illustrated in S08 of FIG. 35 indicates an example of the heart rate data from which to have eliminated the rapid rising/restoration variation of the heart rate superposed on the transition of the heart rate pertaining to the meal in the process of S5 in FIG. 27. In the example of the heart rate in S08 of FIG. 35, the detected heart rate per unit time is registered by being associated with the time information when the heart rate is detected. Note that the time information in S08 of FIG. 35 is expressed in a timestamp format of "month/day/hour/minute/second". The heart rate per unit time is associated with the meal period expressed in a binary status of "0" and "1". In the S08 of FIG. 35, "1" represents the meal period, while "0" represents a period other than the meal period.

The sensor equipment 11 specifies, as a meal anterior period, a predetermined period (e.g., 0 through 30 minutes) before the meal start time of the meal period. The sensor equipment 11 extracts the heart rate data in the meal anterior period from the heart rate data as depicted in a rectangular area encompassed by a bold line in S08 of FIG. 35. Then, the sensor equipment 11 compares the extracted sets of heart rate data with each other, thereby setting a minimum heart rate as the baseline heart rate. S09 in FIG. 35 illustrates an example of setting the minimum heart rate in the rectangular area encompassed by the bold line in S08 of FIG. 35 as the baseline heart rate. As illustrated in S09 of FIG. 35, the minimum heart rate in the rectangular area encompassed by the bold line in S08 of FIG. 35 is "59.0", in which this minimum heart rate is set as the baseline heart rate.

FIG. 36 depicts a correlation between the meal anterior period, the meal period and the baseline heart rate. FIG. 36 illustrates a graph of the transition of the heart rate, in which the axis of ordinates indicates the heart rate per unit time, while the axis of abscissa indicates the elapse time (the period of time). In FIG. 36, a rectangular area encompassed by a bold line indicates the meal anterior period, a rectangular area encompassed by a bold broken line indicates the meal period, and an elongate broken line parallel to the axis of abscissa indicates the baseline heart rate. Note that a rectangular area encompassed by a fine line indicates an elimination period targeted by the noise elimination process in S5.

FIGS. 35 and 36 illustrate examples of setting the baseline heart rate to the minimum heart rate in the meal anterior period. The baseline heart rate may be the heart rate at the meal start time as described in FIG. 2, and may also be an average value of the heart rates acquired during the meal anterior period. A setting method common between or among the plurality of subject persons may be sufficient for setting the baseline heart rate.

Referring back to the flowchart in FIG. 29, the sensor equipment 11 calculates the area size of the first peak area, based on the baseline heart rate calculated in the process of S22 (S23). The area size of the first peak area can be expressed as a total value of the rising widths of the heart rates in the meal period from the baseline heart rate. The sensor equipment 11 extracts, from the heart rate data, the heart rates in the meal period, which are acquired in the process of S2 in FIG. 27. Then, the sensor equipment 11 obtains differences between the extracted heart rates in the meal period and the baseline heart rate, and totalizes the differences of the heart rates with respect to the meal period. The sensor equipment 11 temporarily stores, in a predetermined location of the main storage unit 92, a total of the differences between the heart rates in the meal period and the baseline heart rate as the area size of the first peak area.

Note that the characteristic quantity R1 of the heart rate pertaining to the meal is an area size ratio between the first peak area and the second peak area. Herein, the area sizes of the first and second peak areas can be each obtained as a period-based total of the rising widths from the baseline heart rate. Therefore, in place of the respective area sizes, a period-based average may also be obtained by averaging the period-based totals of the rising widths from the baseline heart rate with the respective periods.

For example, the sensor equipment 11 divides the total of the differences between the heart rates in the meal period by the meal period, thereby calculating a period-based average of the rising widths. The sensor equipment 11 may replace the calculated period-based average of the rising widths with the area size of the first peak area for detecting the characteristic quantity R1 of the heart rate pertaining to the meal.

Similarly to the process in S21, the sensor equipment 11 calculates an area size of the second peak, based on the baseline heart rate calculated in the process of S22 (S24). The area size of the second peak area can be expressed as a total value of the rising widths of the heart rates in the postprandial period from the baseline heart rate. The postprandial period is described as a fixed period (e.g., 4 hours and thereabout) since the end time of the meal period. Incidentally, the postprandial period has already been explained in FIG. 7.

The sensor equipment 11 extracts, from the heart rate data, the heart rates in the postprandial period, which are acquired in the process of S2 in FIG. 27. Then, the sensor equipment 11 obtains differences between the extracted heart rates in the postprandial period and the baseline heart rate, and totalizes the differences of the heart rates with respect to the postprandial period. The sensor equipment 11 temporarily stores, in a predetermined location of the main storage unit 92, a total of the differences between the heart rates in the postprandial period and the baseline heart rate as the area size of the second peak area.

Note that the period-based average of the rising widths of the heart rates in the postprandial period from the baseline heart rate may also be applied to the area size of the second peak area similarly to the area size of the first peak area. It may be sufficient that the sensor equipment 11 calculate the period-based total of the rising widths and the period-based average of the rising widths with respect to the area sizes of the first and second peak areas in accordance with, e.g., a preset condition.

The sensor equipment 11 calculates the area size ratio between the first peak area and the second peak area from the area size of the first peak area and the area size of the second peak area, the area sizes being calculated in the processes of S22-S23 (S25). The sensor equipment 11 temporarily stores, in a predetermined location of the main storage unit 92, the area size ratio calculated in the process of S25 by being associated with, e.g., the time zone of the meal and the identification number of the sensor equipment. The sensor equipment 11 temporarily stores, in a predetermined location of the main storage unit 92, the area size ratio calculated in the process of S25 by being associated with the time zone of the meal and the identification number of the sensor equipment.

Figure 38:
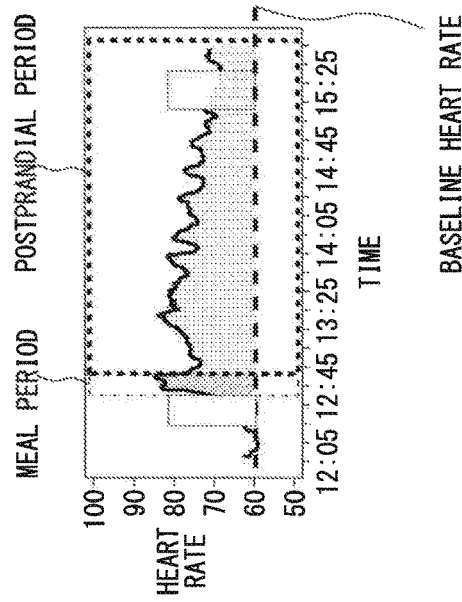
FIG. 38 is an explanatory diagram of a correlation between the meal period, the postprandial period and the baseline heart rate.
Figure 37:
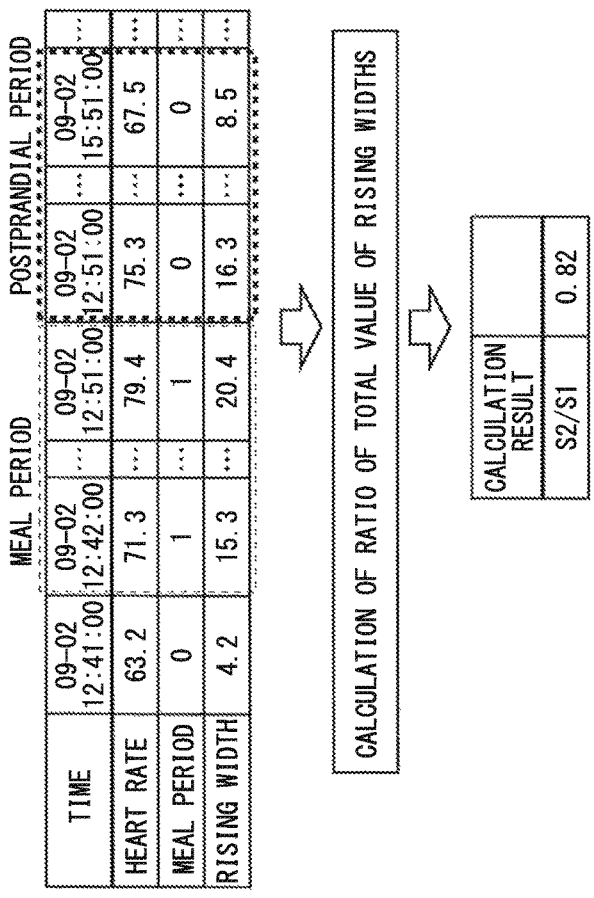
FIG. 37 is an explanatory diagram of an area size ratio between the first peak area and the second peak area.

FIGS. 37 and 38 illustrate explanatory diagrams of the area size ratio between the first peak area and the second peak area. FIG. 37 depicts an example of the heart rate data from which to have eliminated the rapid rising/restoration variation of the heart rate superposed on the transition of the heart rate pertaining to the meal in the process of S5 in FIG. 27. In the example of the heart rate in FIG. 37, the detected heart rate per unit time is registered by being associated with the time information when detecting the heart rate. Further, the heart rate per unit time is associated with each of the meal periods.

In the example of FIG. 37, the difference of the acquired heart rate from the baseline heart rate is associated with each heart rate as a "rising width". Further, a rectangular area encompassed by a thin broken line represents the meal period, while a rectangular area surrounded by a bold broken line represents the postprandial period. An area size of the first peak area is calculated as a total of the rising widths in the rectangular area encompassed by the thin broken line. An area size of the second peak area is calculated as a total of the rising widths in the rectangular area encompassed by the bold broken line.

In the example of FIG. 37, let "S1" be the area size of the first peak area and "S2" be the area size of the second peak area, the area size ratio between the first peak area and the second peak area is calculated by "S1/S2=0.82" as the characteristic quantity R1 of the heart rate pertaining to the meal.

FIG. 38 depicts a correlation between the meal period, the postprandial period and the baseline heart rate. FIG. 38 illustrates a graph of the transition of the heart rate, in which the axis of ordinates indicates the heart rate per unit time, while the axis of abscissa indicates the elapse time (the period of time). In FIG. 38, a rectangular area encompassed by a thin broken line indicates the meal period, a rectangular area encompassed by a bold broken line indicates the postprandial period, and an elongate broken line parallel to the axis of abscissa indicates the baseline heart rate. Note that a rectangular area encompassed by a fine line indicates an elimination period targeted by the noise elimination process in S5.

As seen in the postprandial period in FIG. 38, such a case is assumed that the heart rate data includes the elimination period derived from the exercise period and other equivalent periods when calculating the area size of the second peak area. When the postprandial period covers the elimination period in the calculation of the area size of the second peak area, the rising width of the heart rate can be approximated to the restoration with a fixed gradient from the heart rate of the start time of the elimination period to the heart rate of the end time thereof.

The sensor equipment 11 extracts the heart rate data of the start time of the elimination period and the heart rate data of the end time thereof, and calculates a difference between these two sets of heart rate data. Then, the sensor equipment 11 divides the calculated difference by the elimination period, thus calculating a restoration gradient to be approximated. Subsequently, the sensor equipment 11 may obtain the rising width of the heart rate data in the elimination period by using the approximated restoration gradient. In the example of FIG. 38, a total value of the rising widths of the heart rates in the elimination period is a value given by this calculation: (((Rising Width At Elimination Period Start Time)−(Rising Width At Elimination Period End Time))× (Elimination Period))/2)+((Rising Width At Elimination Period End Time)×(Elimination Period))).

(Calculation of Amplitude Characteristic Quantity)

Figure 39:
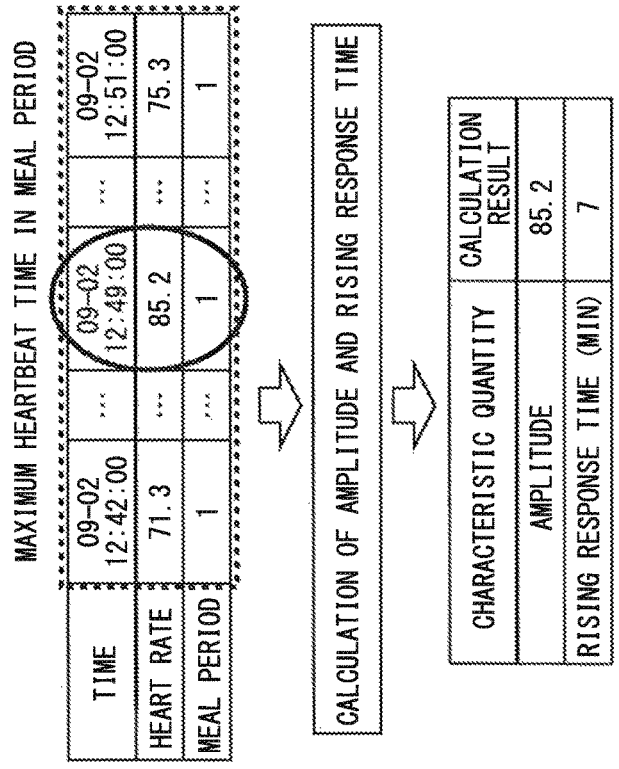
Figures 41, 42:
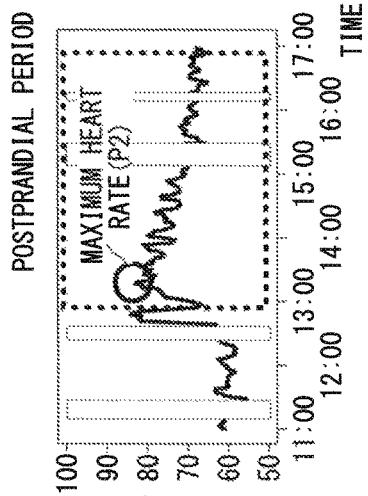
FIG. 41 and FIG. 42 are explanatory diagrams of calculating amplitude characteristic quantities of the second peak.

A calculation of an amplitude characteristic quantity will be described with reference to the flowchart illustrated in FIG. 30 and diagrams in FIGS. 39-42. FIGS. 39 and 41 illustrate examples of the heart rate data from which to have eliminated the rapid rising/restoration variation of the heart rate superposed on the transition of the heart rate pertaining to the meal in the process of S5 in FIG. 27. In the examples of the heart rates in FIGS. 39 and 41, the detected heart rate per unit time is registered by being associated with the time information when detecting the heart rate. Further, the heart rate per unit time is associated with each of the meal periods.

Figure 40:
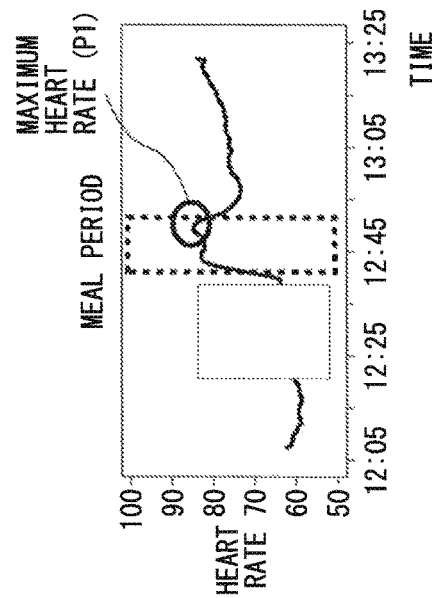
FIG. 39 and FIG. 40 are explanatory diagrams of calculating amplitude characteristic quantities of the first peak.

A rectangular area encompassed by a bold broken line in FIG. 39 represents the meal period, and the heart rate in an area surrounded by a bold line indicates a maximum heart rate (P1) in the meal period. Similarly, a rectangular area encompassed by a bold broken line in FIG. 41 represents the postprandial period, and the heart rate in an area surrounded by a bold line indicates a maximum heart rate (P2) in the postprandial period. FIGS. 40 and 42 are graphs of the transition of the heart rate, in which the axis of ordinates indicates the heart rate per unit time, while the axis of abscissa indicates the elapse time (the period of time).

Figure 30:
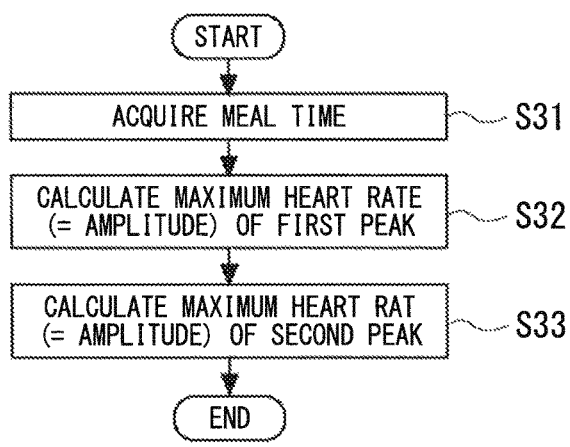
FIG. 30 is a flowchart of a process of calculating amplitude characteristic quantities in S13 of FIG. 28.

In the flowchart illustrated in FIG. 30, in a process of S31, the sensor equipment 11 acquires the meal period specified in the process of S2 in FIG. 27. The sensor equipment 11 extracts the heart rate data associated with the time information, based on the time information of the meal period acquired in the process of S31. The sensor equipment 11 calculates the maximum heart rate (P1) in the meal period by comparing extracted pieces of heart rate data in magnitude, and specifies the calculated maximum heart rate (P1) as the amplitude of the first peak (S32).

The sensor equipment 11 temporarily stores, in a predetermined location of the main storage unit 92, the first peak amplitude specified in the process of S32 by being associated with the time zone of the meal and the identifying information of the sensor equipment 11.

In the example of FIG. 39, the calculation of the maximum heart rate (P1) in the meal period results in "85.2". FIG. 40 depicts a correlation between the meal period and the maximum heart rate (P1) of the first peak. In FIG. 40, a rectangular area encompassed by a bold broken line indicates the meal period, and the heart rate data having the maximum heart rate (P1) exists in an area encircled by a bold line. Note that a rectangular area encompassed by a fine line indicates an elimination period targeted by the noise elimination process in S5.

Referring back to the flowchart in FIG. 30, in the process of S33, the sensor equipment 11 specifies a second peak amplitude in the postprandial period similarly to the process in S31. The sensor equipment 11 specifies the postprandial period, based on the time information of the meal period acquired in the process of S31, and extracts the heart rate data corresponding to the postprandial period. Then, the sensor equipment 11 calculates the maximum heart rate (P2) in the postprandial period by comparing extracted pieces of heart rate data in magnitude, and specifies the calculated maximum heart rate (P2) as the amplitude of the second peak.

In the example of FIG. 41, the maximum heart rate (P2) in the postprandial period is calculated at "83.7". FIG. 42 depicts a correlation between the postprandial period and the maximum heart rate (P2) of the second peak. In FIG. 42, a rectangular area encompassed by a bold broken line indicates the postprandial period, and the heart rate data having the maximum heart rate (P2) exists in an area encircled by a bold line. Note that a rectangular area encompassed by a fine line indicates an elimination period targeted by the noise elimination process in S5.

The sensor equipment 11 temporarily stores, in a predetermined location of the main storage unit 92, the second peak amplitude specified in the process of S33 by being associated with the time zone of the meal and the identifying information of the sensor equipment 11.

(Calculation of Speed Characteristic Quantity)

A calculation of a speed characteristic quantity will hereinafter be described with reference to the flowcharts illustrated in FIGS. 31, 56 and diagrams in FIGS. 43-55. FIGS. 43-49 illustrate examples of the heart rate data from which to have eliminated the rapid rising/restoration variation of the heart rate superposed on the transition of the heart rate pertaining to the meal in the process of S5 in FIG. 27. In the examples of the heart rates in FIGS. 43-49, the detected heart rate per unit time is registered by being associated with the time information when detecting the heart rate. Further, the heart rate per unit time is associated with each of the meal periods. FIGS. 44-50 are graphs of the transition of the heart rate, in which the axis of ordinates indicates the heart rate per unit time, while the axis of abscissa indicates the elapse time (the period of time).

Figure 31:
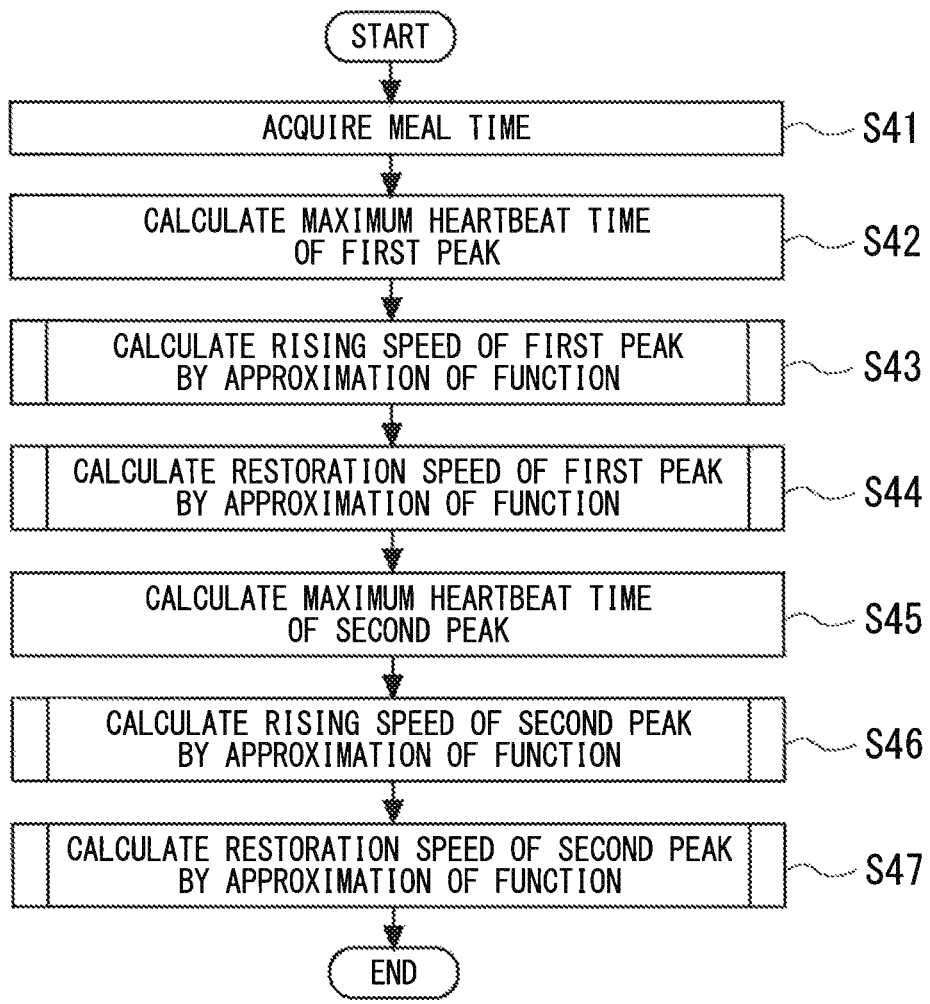
FIG. 31 is a flowchart of a process of calculating speed characteristic quantities in S14 of FIG. 28.

In the flowchart illustrated in FIG. 31, in a process of S41, the sensor equipment 11 acquires the meal period specified in the process of S2 in FIG. 27. The sensor equipment 11 extracts the heart rate data associated with the time information, based on the time information of the meal period acquired in the process of S41. The sensor equipment 11 calculates the maximum heart rate (P1) in the meal period by comparing extracted pieces of heart rate data in magnitude, and acquires time (reaching time) of the calculated maximum heart rate (P1) (S42).

The sensor equipment 11 specifies the heart rate data for calculating the rising/response speed of the first peak from the reaching time of the maximum heart rate (P1) acquired in the process in S42. The sensor equipment 11 performs approximation of function about the specified heart rate data of (Meal Period Start Time–Maximum Heart Rate Reaching Time), thereby calculating the rising/response speed of the first peak (S43).

The approximation of function performed in the process of S43 can be exemplified by the approximation of function using a linear function instanced by "f(t)=αt+β". The approximation of function using the linear function can involve performing the approximation of function suited to approximation target data by obtaining such a combination of parameters (α, β) as to minimize an approximation error (squared error) at each point of time of the approximation target data.

Figure 55:
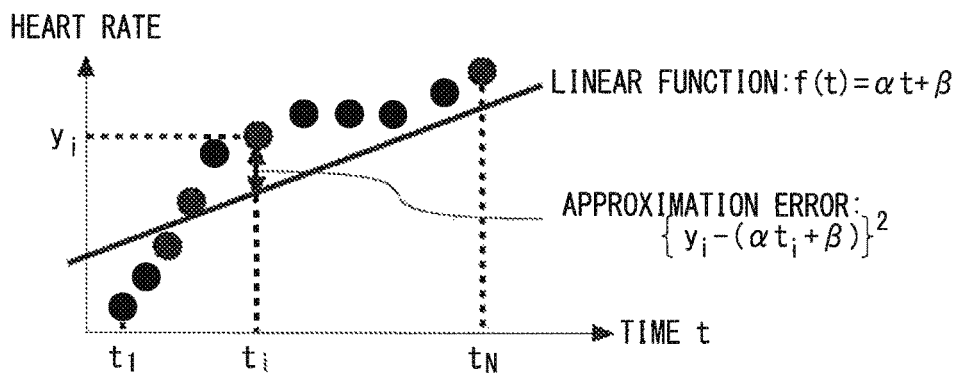
FIG. 55 is an explanatory diagram of an approximation error.

FIG. 55 illustrates an explanatory diagram about the approximation error. In the explanatory diagram illustrated in FIG. 55, the axis of ordinates indicates the heart rate per unit time, while the axis of abscissa indicates the elapse time (the period of time). The approximation target data are assumed to be the heart rate data in a range from the meal start time to the reaching time of the maximum heart rate (P1). Each piece of heart rate data is indicated by a blackened circle "●". In FIG. 55, time: t1 designates the meal start time, and time: tN represents the reaching time of the maximum heart rate (P1). Each heart rate data per time can be expressed by "yi(i=1−N)".

In the explanatory diagram illustrated in FIG. 55, a bold line represents a linear function: f(t)=αt+β, which indicates approximation to the transition of the heart rate data in the range from the meal start time to the reaching time of the maximum heart rate (P1). An approximation error between the heart rate data: yi at the time: ti and the linear function: f(t)=αt+β, can be expressed as a square of {yi−(αti+β)}.

For obtaining an approximation function suited to the transition of the heart rate data from the meal start time to the reaching time of the maximum heart rate (P1), it may be sufficient to obtain such a combination of (α, β) as to minimize a sum of squares of approximation error: {yi−(αti+β)} per heart rate. A mathematical expression 1 illustrates an error function: E(α, β) about an approximation function: f(t)=αt+β.

[Mathematical Expression 1]
$$E(\alpha, \beta) = \sum_{i=1}^{N} \{y_i - (\alpha t_i + \beta)\}^2$$

where

α: a gradient parameter,

β: an intercept parameter, yi: a heart rate of i-th data, ti: time of i-th data, N: data count of target range.

In the mathematical expression 1, "α" represents a gradient parameter of the approximation function, and "β" denotes an intercept parameter of the approximation function. Further, "yi" designates i-th data (heart rate), and "ti" represents time of the i-th data. Note that "N" in the mathematical expression 1 designates an approximation target data count.

For obtaining such a combination of (α, β) as to minimize the sum in the mathematical expression 1, it may be sufficient to obtain such a combination of (α, β) that when performing partial differentiation of the mathematical expression 1 by using any one of "α" and "β" as a variable while using the other as a constant and vice versa, both of values result in "0". A mathematical expression 2 is an example of a function form when performing the partial differentiation of a right side of the mathematical expression 1 by using "α", while a mathematical expression 3 is an example of the function form when performing the partial differentiation by using "β".

[Mathematical Expression 2]
$$\frac{\partial E(\alpha, \beta)}{\partial \alpha} = \sum_{i=1}^{N} (-2t_i)\{y_i - (\alpha t_i + \beta)\}$$
$$= 2\alpha \left(\sum_{i=1}^{N} t_i^2\right) - 2\beta \left(\sum_{i=1}^{N} t_i\right) - 2\left(\sum_{i=1}^{N} y_i t_i\right)$$

[Mathematical Expression 3]

$$\frac{\partial E(\alpha, \beta)}{\partial \beta} = \sum_{i=1}^{N}(-2)\{y_i - (\alpha t_i + \beta)\}$$
$$= 2\alpha\left(\sum_{i=1}^{N} t_i\right) - 2N\beta - 2\left(\sum_{i=1}^{N} y_i\right)$$

When replacing a total sum of "ti2", "ti", "yiti", "yi" in the mathematical expressions 2 and 3 by "C1-C4" as illustrated in a mathematical expression 4, the mathematical expression 2 is transformed into a mathematical expression 5, and the mathematical expression 3 is transformed into a mathematical expression 6.

[Mathematical Expression 4]

$$\left(\sum_{i=1}^{N} t_i^2\right) = C_1 \left(\sum_{i=1}^{N} t_i\right) = C_2 \left(\sum_{i=t}^{n} y_i t_i\right) = C_3 \left(\sum_{i=1}^{N} y_i\right) = C_4$$

[Mathematical Expression 5]

$$C_1 \alpha - C_2 \beta - C_3 = 0$$

[Mathematical Expression 6]

$$C_2 \alpha - N\beta - C_4 = 0$$

The mathematical expression 6 is transformed, whereby "β" is expressed by a mathematical expression 7.

[Mathematical Expression 7]

$$\beta = \frac{C_2 \alpha - C_4}{N}$$

The transformed mathematical expression 7 is substituted into the mathematical expression 5, thereby enabling "α" to be obtained. Further, the obtained "α" is substituted into the mathematical expression 7, thereby enabling "β" to be obtained. As a result, it is feasible to obtain such a combination of (α, β) as to minimize the mathematical expression 1.

[Mathematical Expression 8]

$$\alpha = \frac{NC_3 - C_2 C_4}{NC_1 - C_2^2}$$
$$\beta = \frac{C_3 C_2 - C_1 C_4}{NC_1 - C_2^2}$$

Figure 56:
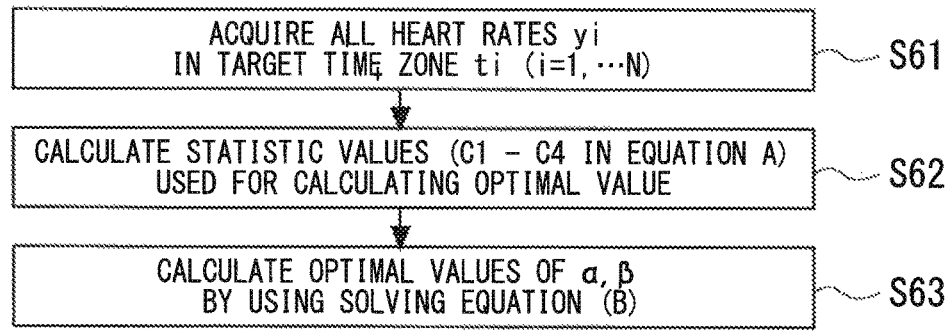
FIG. 56 is a flowchart of a derivation process of parameters α, β of an approximation function.
Figure 57:
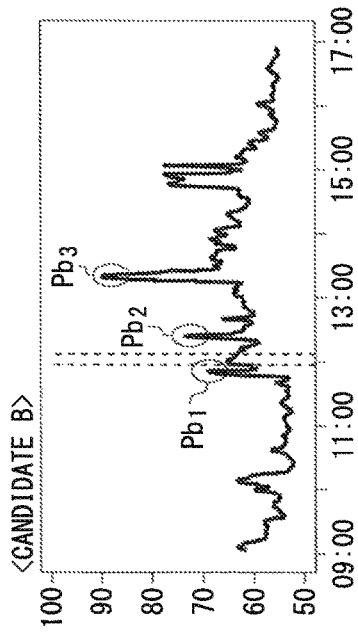
FIG. 57, FIG. 58, FIG. 59 and FIG. 60 are diagrams illustrating examples of experimentally acquired heart rate data.

FIG. 56 illustrates a flowchart of a derivation process of an optimal solution of the parameters α, β of the approximation function: f(t)=αt+β, i.e., the derivation process of the parameters α, β satisfying the mathematical expression 8. Note that a mathematical expression of the total sum related to coefficients C1-C4 given in the mathematical expression 4 and a mathematical expression for deriving the parameters α, β given in the mathematical expression 8, may be previously stored in a predetermined location of the auxiliary storage unit 93. It may be sufficient that the sensor equipment 11 executes the derivation process of S61-S63 by referring to a relation between the mathematical expression 4 and the mathematical expression 8 each stored in the auxiliary storage unit 93 when processing S43 illustrated in FIG. 31.

In a process of S61 in the flowchart illustrated in FIG. 56, the sensor equipment 11 acquires all of the heart rate data in the approximation target period together with the time information associated therewith. Then, the sensor equipment 11 calculates the coefficients C1-C4 given in the mathematical expression 4, based on the heart rate data acquired in the process of S61 (S62). The sensor equipment 11 temporarily stores the calculated coefficients C1-C4 by being associated with the approximate target period in a predetermined location of the main storage unit 92.

In a process of S63, the sensor equipment 11 calculates optimal values of the parameters α, β of the approximation function, based on coefficients C1-C4 calculated in the process of S62. The sensor equipment 11 calculates the optimal values of parameters α, β satisfying the mathematical expression 8 by referring to a relation of the mathematical expression 8 about the parameters α, β, the mathematical expression 8 being stored in the auxiliary storage unit 93. The sensor equipment 11 temporarily stores the calculated parameters α, β by being associated with the approximation target period in a predetermined location of the main storage unit 92.

Figure 43:
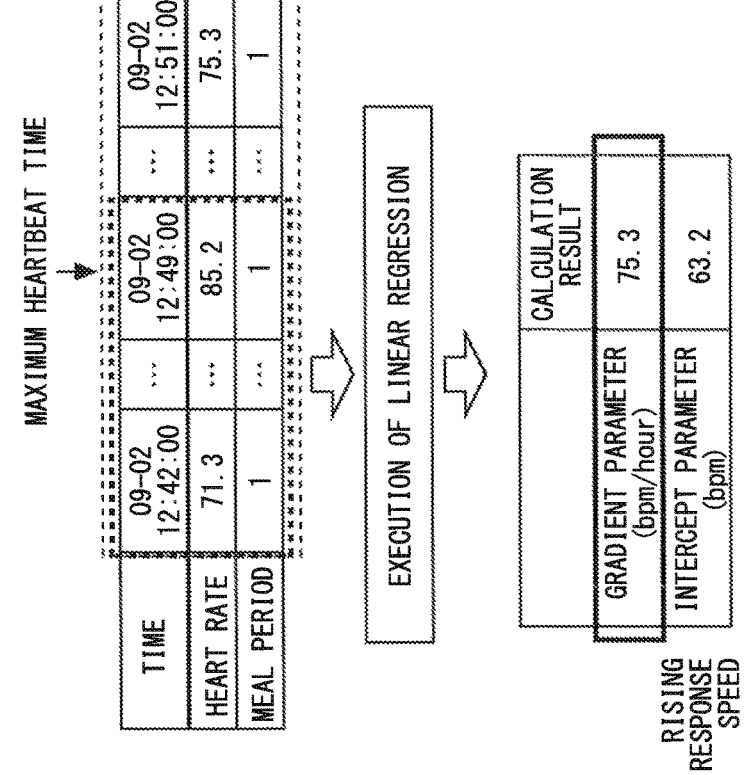
FIG. 43 is an explanatory diagram of calculating a rising response speed of the first peak.

In the explanatory example of FIG. 43, the parameter "α" (gradient parameter) of the approximation function about the heart rate data in the range from the meal period start time to the reaching time of the maximum heart rate as the processing target in S43, is calculated at "75.3 (bpm/hour)". Similarly, the parameter (intercept parameter) of the approximation function is calculated at "63.2 (bpm)".

Figure 44:
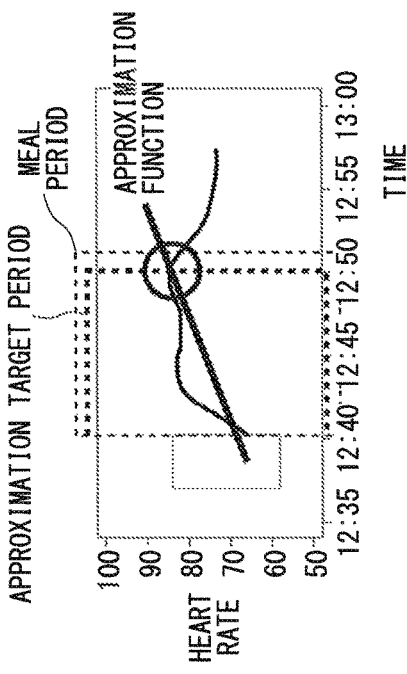
FIG. 44 is an explanatory diagram of a relation between the meal period, the approximation target period and the approximation function.

FIG. 44 illustrates a relation between the meal period, the approximation target period and the approximation function. A rectangular area encompassed by a thin broken line in FIG. 44 represents the meal period; a rectangular area encompassed by a bold broken line represents the approximation target period; and a bold line indicates the approximation function about the transition of the heart rate in the approximation target period. Note that a rectangular area encompassed by a fine line represents the elimination period targeted by the noise elimination process in S5.

Referring back to the flowchart illustrated in FIG. 31, in the process of S44, the sensor equipment 11 calculates the restoration response speed of the first peak by the approximation of function. The sensor equipment 11 specifies the approximation target period for calculating the restoration response speed of the first peak, based on the time information of the meal period acquired in the process of S41.

Figure 45:
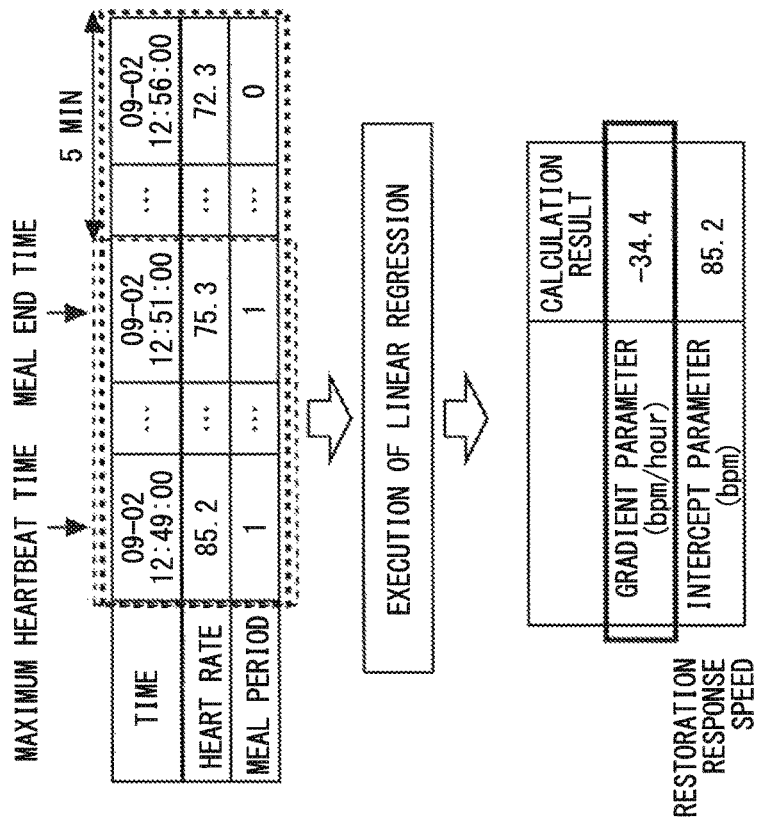
FIG. 45 is an explanatory diagram of calculating a restoration response speed of the first peak.

The approximation target period for calculating the restoration response speed of the first peak can be set to a period from the time when reaching the maximum heart rate to the meal end time inclusive of an addition of a fixed period as seen in the area encompassed by the bold broken line in FIG. 45. FIG. 45 depicts an example of setting, as the approximation target period, "(Maximum Heart Rate Reaching Time)–(Meal End time+5 Min)" by adding a period of "5 minutes" to the meal end time.

The sensor equipment 11 may store the preset "fixed period" in a predetermined location of the auxiliary storage unit 93. Then, the sensor equipment 11 may refer to the "fixed period" stored in the auxiliary storage unit 93 as triggered by executing the process in S44, and may specify the approximation target period, based on the meal end time of the meal period acquired in the process of S41.

The sensor equipment 11 extracts the heart rate data of the specified approximation target period, i.e., "(Maximum Heart Rate Reaching Time)–(Meal End time+5 Min)". Subsequently, the sensor equipment 11 sets the heart rate data of the approximation target period as the processing target data, and thus performs the approximation of function based on the linear function: $f(t)=\alpha t+\beta$. Note that the approximation of function based on the linear function: $f(t)=\alpha t+\beta$ in the process of S44 involves executing the same process as the process in S43.

The approximation of function based on the linear function: $f(t)=\alpha t+\beta$ entails executing the processes in S61-S63 illustrated in FIG. 56, in which the heart rate data of the extracted approximation target period are set as the processing target data. The sensor equipment 11 executes the derivation process of the parameters $\alpha$, $\beta$ in S61-S63 about the heart rate data of the extracted approximation target period, thereby calculating the optimal values of the parameters $\alpha$, $\beta$ to minimize the approximation error through the approximation of function. As a result, the sensor equipment 11 can calculate the restoration response speed of the first peak based on the transition of the heart rate data extracted in the approximation target period.

The sensor equipment 11 temporarily stores, in a predetermined location of the main storage unit 92, the parameters $\alpha$, $\beta$ of the approximation function calculated about the restoration response speed of the first peak by being associated with the approximation target period.

In the explanatory example of FIG. 45, the parameter "$\alpha$" (gradient parameter) of the approximation function about the heart rate data of "(Maximum Heart Rate Reaching Time)–(Meal End time+5 Min)" as the processing target in S44, is calculated at "–34.4 (bpm/hour)". Similarly, the parameter "$\beta$" (intercept parameter) of the approximation function is calculated at "85.2 (bpm)".

Figure 46:
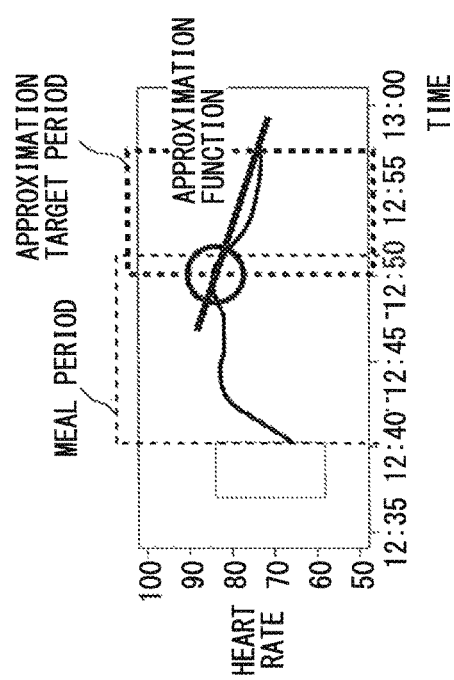
FIG. 46 is an explanatory diagram of a relation between a period from meal start time up to meal end time, the approximation target period and the approximation function.

FIG. 46 depicts a relation between a period from meal start time up to meal end time, the approximation target period and the approximation function. A rectangular area encompassed by a thin broken line in FIG. 46 represents the period up to "(Meal Start Time)–(Meal End time)", and a rectangular area encompassed by a bold broken line represents the approximation target period, and a bold line indicates the approximation function about the transition of the heart rate in the approximation target period. Note that a rectangular area encompassed by a fine line represents the elimination period targeted by the noise elimination process in S5.

Referring back to the flowchart illustrated in FIG. 31, in the processes of S45-S47, the sensor equipment 11 calculates the response speed (the rising response speed, the restoration response speed) of the second peak by performing the approximation of function about a transition variation of the heart rate data similarly to S42-S44.

The process in S45 involves calculating the reaching time of the maximum heart rate (P2) of the second peak in order to specify the target heart rate data for calculating the response speed of the second peak.

The sensor equipment 11 acquires the meal period specified in the process of S2 in FIG. 27. The sensor equipment 11 sets the end time of the acquired meal period as the start time of the postprandial period, and extracts the heart rate data in the postprandial period. The postprandial period is a fixed period (e.g., 4 hours or thereabout) from the end time of the meal period. Incidentally, the postprandial period has already been described in FIG. 7.

The sensor equipment 11 calculates the maximum heart rate (P2) in the postprandial period by comparing extracted pieces of heart rate data in the postprandial period in magnitude, and acquires the time (reaching time) of the calculated maximum heart rate (P2).

Note that the sensor equipment 11 may extract the heart rate data by specifying a period (e.g., a period till an elapse of 30-80 min since the meal start time) with the digestive activity becoming active when calculating the reaching time of the maximum heart rate (P2).

In the process of S46, the sensor equipment 11 calculates the rising response speed of the second peak by performing the approximation of function based on the reaching time of the maximum heart rate (P2) of the second peak, the reaching time being calculated in the process of S45. The sensor equipment 11 specifies an extraction period (approximation target period) of the heart rate data for calculating the rising response speed of the second peak from the reaching time of the maximum heart rate (P2) of the postprandial period acquired in the process of S45. The sensor equipment 11 specifies the approximation target period for calculating the rising response speed of the second peak, based on the start time (the end time of the meal period) of the postprandial period and the reaching time of the maximum heart rate (P2) of the postprandial period. Then, the sensor equipment 11 extracts the heart rate data in the specified approximate period (given by (Postprandial Period Start Time–Maximum Heart Rate (P2) Reaching Time)).

Figure 47:
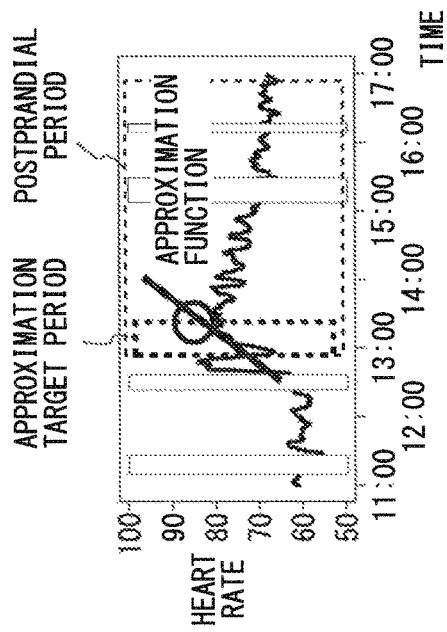
FIG. 47 is an explanatory diagram of calculating a rising response speed of the second peak.

In the example of FIG. 47, an area encompassed by a thin broken line represents the postprandial period starting at the meal end time, and an area encompassed by a bold broken line represents the approximation target period till the reaching time of the maximum heart rate (P2) in the postprandial period since the start time (the meal end time) of the postprandial period. The sensor equipment 11 extracts the heart rate data of the area encompassed by the bold broken line.

The sensor equipment 11 performs the approximation of function targeting in processing on the heart rate data of the extracted approximation target period (given by (Postprandial Period Start Time–Maximum Heart Rate (P2) Reaching Time)), thereby calculating the rising response speed of the second peak. Note that the approximation of function in the process of S46 is performed based in the linear function: $f(t)=\alpha t+\beta$ similarly to the process of S43.

In the approximation of function based on the linear function: $f(t)=\alpha t+\beta$, the sensor equipment 11 executes the derivation process of parameters $\alpha$, $\beta$ in S61-S63 illustrated in FIG. 56 by targeting in processing on the heart rate data of the extracted approximation target period. Through the derivation process in S61-S63 illustrated in FIG. 56, the sensor equipment 11 calculates the optimal values of the parameters $\alpha$, $\beta$ to minimize the approximation error by the linear function: $f(t)=\alpha t+\beta$. As a result, the sensor equipment 11 is thereby enabled to calculate the rising response speed of the second peak based on the transition of the heart rate data extracted in relation to (Postprandial Period Start Time–Maximum Heart Rate (P2) Reaching Time).

The sensor equipment 11 temporarily stores, in a predetermined location of the main storage unit 92, the calculated (optimal values of the) parameters $\alpha$, $\beta$ of the linear function: $f(t)=\alpha t+\beta$ about the rising response speed of the second peak by being associated with the approximation target period.

In the explanatory example in FIG. 47, the parameter "$\alpha$" (gradient parameter) of the linear function about the heart rate data given by (Postprandial Period Start Time–Maximum Heart Rate (P2) Reaching Time) as the processing target in S46, is calculated at "17.1 (bpm/hour)". Similarly, the parameter "$\beta$" (intercept parameter) of the linear function is calculated at "66.9 (bpm)".

Figure 48:
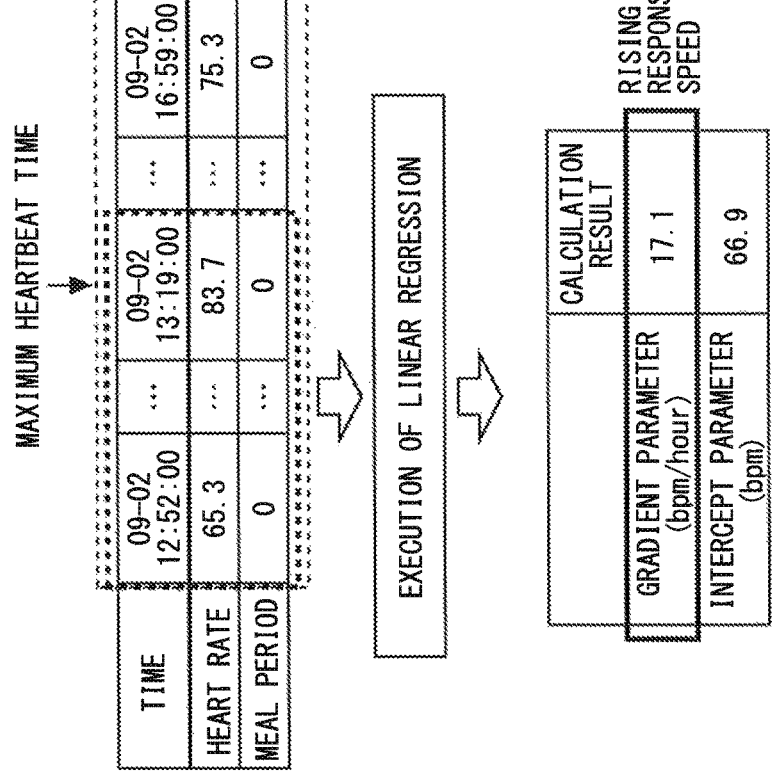
FIG. 48 is an explanatory diagram of a relation between the postprandial period, the approximation target period and the approximation function.

FIG. 48 depicts a relation between the postprandial period, the approximation target period and the approximation function. A rectangular area encompassed by a thin broken line in FIG. 48 represents the postprandial period, a rectangular area encompassed by a bold broken line represents the approximation target period, and a bold line indicates the approximation function about the transition of the heart rate in the approximation target period. Note that a rectangular area encompassed by a fine line indicates an elimination period targeted by the noise elimination process in S5.

Referring back to the flowchart illustrated in FIG. 31, in the process of S47, the sensor equipment 11 calculates, based on the reaching time of the maximum heart rate (P2) of the second peak that is calculated in the process of S45, the restoration response speed of the second peak by the approximation of function. The sensor equipment 11 specifies the extraction period (approximation target period) of the heart rate data for calculating the restoration response speed of the second peak from the reaching time of the maximum heart rate (P2) in the postprandial period acquired in the process of S45. The sensor equipment 11 specifies the approximation target period for calculating the restoration response speed of the second peak, based on the reaching time of the maximum heart rate (P2) in the postprandial period and the end time of the postprandial period. Then, the sensor equipment 11 extracts the heart rate data of the specified approximation period (a period given by (Maximum Heart Rate (P2) Reaching Time of Postprandial Period–Postprandial Period End Time)).

Figure 49:
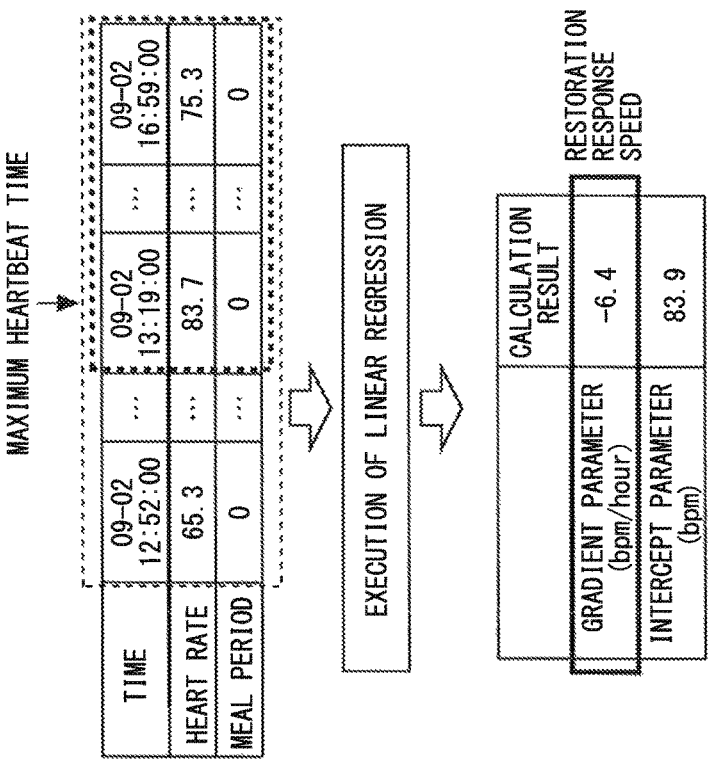
FIG. 49 is an explanatory diagram of calculating a restoration response speed of the second peak.

In the example of FIG. 49, an area encompassed by a thin broken line represents the postprandial period, an area encompassed by a bold broken line represents the approximation target period till the end time of the postprandial period since the reaching time of the maximum heart rate (P2). The sensor equipment 11 extracts the heart rate data of, e.g., the area encompassed by the bold broken line.

The sensor equipment 11 calculates the restoration response speed of the second peak by performing the approximation of function, targeting in processing on the heart rate data of the extracted approximation target period (Maximum Heart Rate (P2) Reaching Time–Postprandial Period End Time). Note that the approximation of function in the process of S47 is performed based on the linear function: $f(t)=\alpha t+\beta$ similarly to the process in S43.

The approximation of function based on the linear function: $f(t)=\alpha t+\beta$ entails executing the derivation process of the parameters $\alpha$, $\beta$ in S61-S63 illustrated in FIG. 56 by targeting in processing on the heart rate data of the extracted approximation target period. Through the derivation process in S61-S63 illustrated in FIG. 56, the sensor equipment 11 calculates the optimal values of the parameters $\alpha$, $\beta$ to minimize the approximation error by the linear function: $f(t)=\alpha t+\beta$. As a result, the sensor equipment 11 is thereby enabled to calculate the restoration response speed of the second peak based on the transition of the heart rate data extracted in relation to approximation target period (Maximum Heart Rate (P2) Reaching Time–Postprandial Period End Time).

The sensor equipment 11 temporarily stores, in a predetermined location of the main storage unit 92, the calculated (optimal values of the) parameters $\alpha$, $\beta$ of the linear function: $f(t)=\alpha t+\beta$ about the restoration response speed of the second peak by being associated with the approximation target period.

In the explanatory example in FIG. 49, the parameter "$\alpha$" (gradient parameter) of the linear function about the heart rate data given by (Maximum Heart Rate (P2) Reaching Time–Postprandial Period End Time) as the processing target in S47, is calculated at "−6.4 (bpm/hour)". Similarly, the parameter "$\beta$" (intercept parameter) of the linear function is calculated at "83.9 (bpm)".

Figure 50:
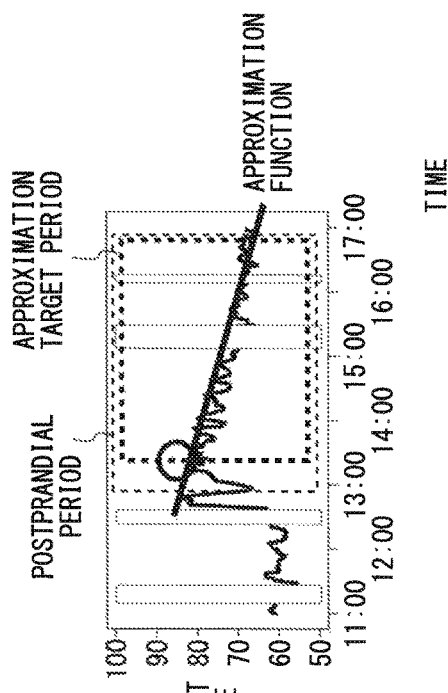
FIG. 50 is an explanatory diagram of a relation between the postprandial period, the approximation target period and the approximation function.

FIG. 50 depicts a relation between the postprandial period, the approximation target period and the approximation function. A rectangular area encompassed by a thin broken line in FIG. 50 represents the postprandial period, a rectangular area encompassed by a bold broken line represents the approximation target period, and a bold line indicates the approximation function about the transition of the heart rate in the approximation target period. Note that a rectangular area encompassed by a fine line indicates an elimination period targeted by the noise elimination process in S5.

(Calculation of Time Characteristic Quantity)

A calculation of the time characteristic quantity will hereinafter be described with reference to the flowcharts illustrated in FIGS. 32 and 56 and the diagrams in FIGS. 39-42 and 51-54. FIGS. 51-54 are graphs of the transition of the heart rate, in which the axis of ordinates indicates the heart rate per unit time, while the axis of abscissa indicates the elapse time (the period of time).

Figure 32:
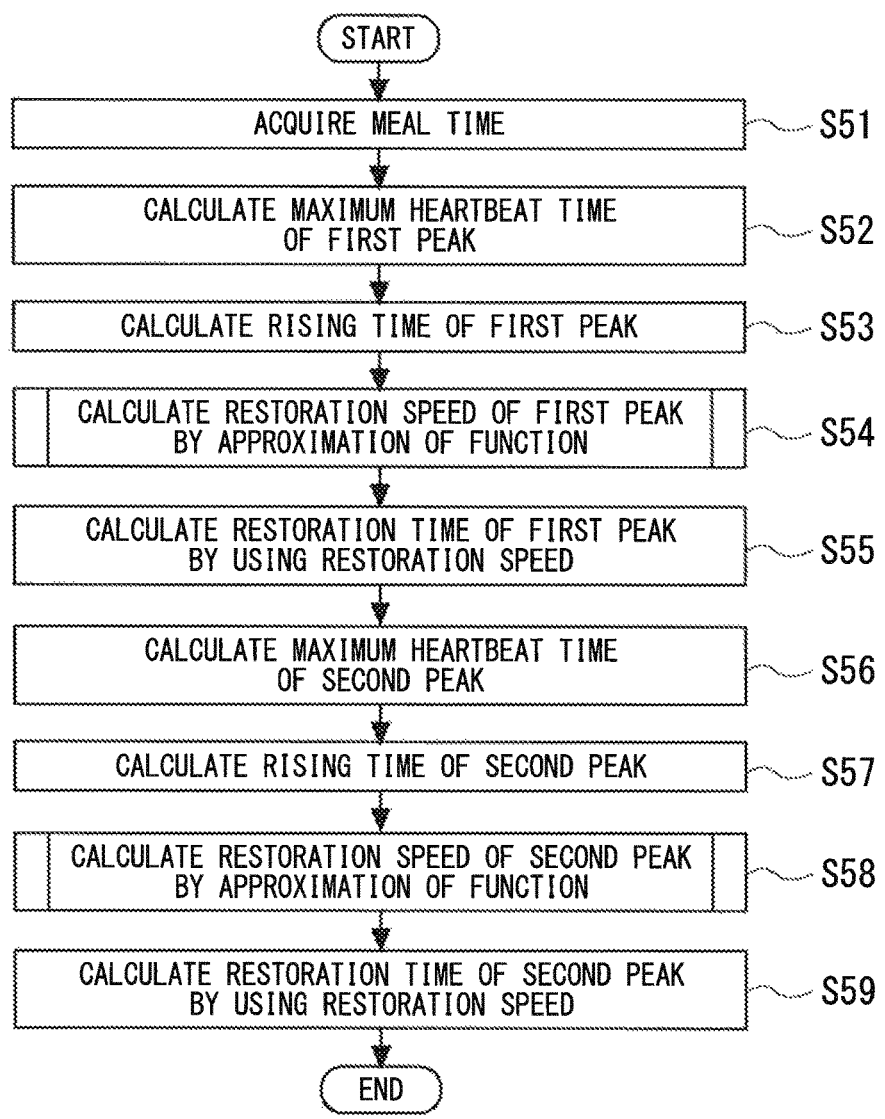
FIG. 32 is a flowchart of a process of calculating time characteristic quantities in S15 of FIG. 28.

In the flowchart illustrated in FIG. 32, the sensor equipment 11 specifies the time when reaching the maximum heart rate (P1) of the first peak in the meal period in order to calculate the rising response time and the restoration response time of the first peak. The sensor equipment 11 calculates the rising response time and the restoration response time of the first peak, based on the specified reaching time of the maximum heart rate (P1) of the first peak. Note that the restoration response time of the first peak is calculated based on the gradient parameter "$\alpha$" of the approximation function, the maximum heart rate (P1) of the first peak and the baseline heart rate, which are explained in the process of S44 illustrated in FIG. 31.

With respect to the second peak, the sensor equipment 11 likewise specifies the time when reaching the maximum heart rate (P2) of the second peak in the postprandial period in order to calculate the rising response time and the restoration response time of the second peak. Subsequently, the sensor equipment 11 calculates the rising response time and the restoration response time of the second peak, based on the specified reaching time of the maximum heart rate (P2) of the second peak. Note that the restoration response time of the second peak is calculated based on the gradient parameter "$\alpha$" of the approximation function, the maximum heart rate (P2) of the second peak and the baseline heart rate, which are explained in the process of S47 illustrated in FIG. 31.

In the flowchart illustrated in FIG. 32, in the process of S51, the sensor equipment 11 acquires the meal period specified in the process of S2 in FIG. 27. The sensor equipment 11 extracts the heart rate data associated with the time information, based on the time information of the meal period acquired in the process of S51. Then, the sensor equipment 11 calculates the maximum heart rate (P1) in the meal period by comparing extracted pieces of heart rate data in magnitude, and thus acquires the time (reaching time) of the heart rate data of the maximum heart rate (P1) (S52).

The sensor equipment 11 calculates the rising response time of the first peak from the meal period start time acquired in the process of S51 and the reaching time of the maximum heart rate (P1) acquired in the process of S52 (S53). The sensor equipment 11 temporarily stores, in a predetermined location of the main storage unit 92, the rising response time of the first peak calculated in the process of S53 by being associated with, e.g., the time zone of the meal and the identifying information of the sensor equipment 11.

In the explanatory diagram illustrated in FIG. 39, the rising response time of the first peak from the meal period start time to the reaching time of the maximum heart rate (P1), is calculated at "7 (min)".

Referring back to the flowchart illustrated in FIG. 32, in the process of S54, the sensor equipment 11 calculates the restoration response speed of the first peak by the approximation of function in order to calculate the restoration response time of the first peak. Incidentally, the process in S54 is the same as the process in S44 depicted in FIG. 31, and hence its explanation is omitted. The sensor equipment 11 calculates the gradient parameter "α" of the approximation function (the linear function: $f(t)=\alpha t+\beta$) by executing the process in S44 illustrated in FIG. 31.

In the process of S55, the sensor equipment 11 calculates the restoration response time of the first peak on the basis of the gradient parameter "α" of the approximation function, the parameter "α" being calculated in the process of S54. The restoration response time of the first peak can be, as described in FIG. 13, detected as the period till the heart rate of the restoration reaches the baseline heart rate (BL1) with the elapse of time from the maximum heart rate (P1) of the first peak.

The baseline heart rate (BL1) is, as explained in FIG. 35 and other equivalent drawings, set to the minimum heart rate of the predetermined period (e.g., 0-30 min) before the meal start time. Note that the baseline heart rate (BL1) may be, as explained in FIG. 2, the heart rate at the meal start time and may also be the average value of the heart rates, which is acquired in the meal anterior period. A method of setting the baseline heart rate (BL1) may be sufficient if common between or among the plurality of subject persons.

Figures 51, 52:
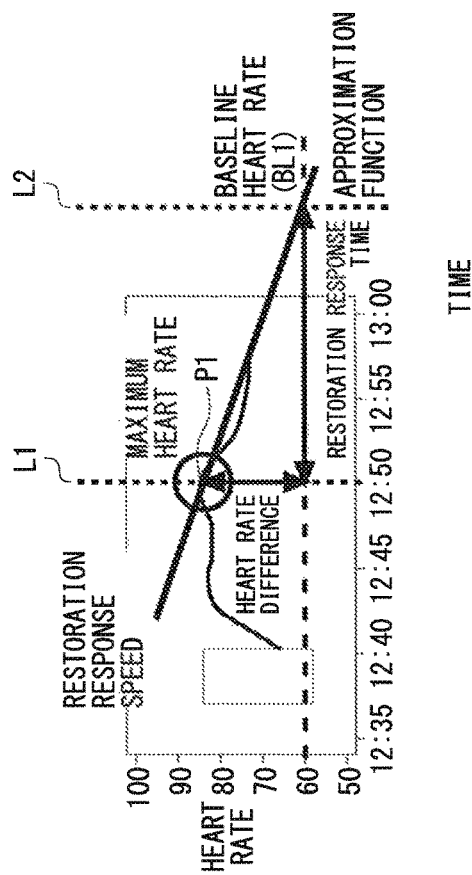
FIGS. 51 and 52 are explanatory diagrams of calculating a restoration response time of the first peak.

FIG. 51 illustrates a relation between the maximum heart rate (P1) of the first peak, the baseline heart rate (BL1) and the restoration response speed of the first peak, which is approximated by the linear function. A broken line L1 parallel to the axis of ordinates in FIG. 51 indicates the reaching time of the maximum heart rate (P1) of the first peak, and a broken line L2 indicates the time when the linear function of the restoration response speed of the first peak intersects the baseline heart rate (BL1). A solid line marked with arrows at both ends in parallel to the axis of ordinates indicates a difference between the baseline heart rate (BL1) and the maximum heart rate (P1) of the first peak, and a solid line marked with arrows at both ends in parallel to the axis of abscissa indicates the restoration response time of the first peak.

As illustrated in FIG. 51, the restoration response time of the first peak is calculated as a value (time) obtained by dividing the difference between the baseline heart rate (BL1) and the maximum heart rate (P1) of the first peak by the gradient parameter "α" of the approximation function (the linear function).

The sensor equipment 11 calculates the baseline heart rate (BL1) as explained in the process of S22 in FIG. 29. Then, the sensor equipment 11 calculates the difference between the maximum heart rate (P1) of the first peak calculated in the process of S52 and the baseline heart rate (BL1). The sensor equipment 11 calculates the restoration response time of the first peak by dividing the heart rate difference calculated above by the gradient parameter "α" calculated in the process of S54.

In the example of FIG. 51, the maximum heart rate (P1) of the first peak is "85.2 (bpm)"; the baseline heart rate (BL1) is "59.0 (bpm)"; and the heart rate difference is "26.2 (bpm)". Further, the gradient parameter "α" of the linear function to approximate the restoration response speed of the first peak is "−34.4 (bpm/hour)", and the restoration response time of the first peak is calculated at "45.7 (min)" by "(Heart Rate Difference)/(Gradient Parameter "α")".

The sensor equipment 11 temporarily stores, in a predetermined location of the main storage unit 92, the restoration response time of the first peak that is calculated in the process of S55 by being associated with the time zone of the meal and the identifying information of the sensor equipment 11.

Referring back to the flowchart illustrated in FIG. 32, in the processes of S56-S59, the sensor equipment 11 executes the same processes as S52-S55 about the second peak, thereby calculating the rising response time and the restoration response time of the second peak. In the process of S56, the sensor equipment 11 calculates the reaching time of the maximum heart rate (P2) of the second peak in order to calculate the rising response time and the restoration response time of the second peak.

The sensor equipment 11 acquires the meal period specified in the process of S2 in FIG. 27. The sensor equipment 11 sets the acquired meal period end time as the start time of the postprandial period, and extracts the heart rate data in the postprandial period. The postprandial period is a fixed period (e.g., 4 hours or thereabout) since the end time of the meal period. Incidentally, the postprandial period has already been described in FIG. 7.

The sensor equipment 11 calculates the maximum heart rate (P2) in the postprandial period by comparing the extracted pieces of heart rate data in the postprandial period in terms of the magnitude, thereby acquiring the time (the reaching time) of the calculated maximum heart rate (P2).

Note that the sensor equipment 11 may extract the heart rate data by specifying a period (e.g., a period till an elapse of 30-80 min since the meal start time) with the digestive activity becoming active when calculating the reaching time of the maximum heart rate (P2).

The sensor equipment 11 calculates the rising response time of the second peak from the meal period end time acquired in the process of S51 and the reaching time of the maximum heart rate (P2) acquired in the process of S56 (S57). The sensor equipment 11 temporarily stores, in a predetermined location of the main storage unit 92, the rising response time of the second peak that is calculated in the process of S57 by being associated with the time zone of the meal and the identifying information of the sensor equipment 11.

In the explanatory diagram illustrated in FIG. 41, the rising response time of the second peak till the reaching time of the maximum heart rate (P2) since the start time of the postprandial period, is calculated at "27 (min)".

Referring back to the flowchart illustrated in FIG. 32, in the process of S58, the sensor equipment 11 executes calculates the restoration response speed of the second peak by performing the approximation of function in order to calculate the restoration response time of the second peak. Note that the process in S58 is the same as the process in S46 illustrated in FIG. 31, and hence its explanation is omitted. The sensor equipment 11 executes the process in S46 illustrated in FIG. 31, thereby calculating the gradient parameter "α" about the approximation function (the linear function: $f(t)=\alpha t+\beta$).

In the process of S59, the sensor equipment 11 calculates the restoration response time of the second peak, based on the gradient parameter "α" of the approximate function, the parameter "a" being calculated in the process of S58. The restoration response time of the second peak can be, as described in FIG. 14, detected as the period till the heart rate of the restoration reaches the baseline heart rate (BL1) with the elapse of time from the maximum heart rate (P2) of the second peak. The baseline heart rate (BL1) has already been explained in the process of S55.

Figures 53, 54:
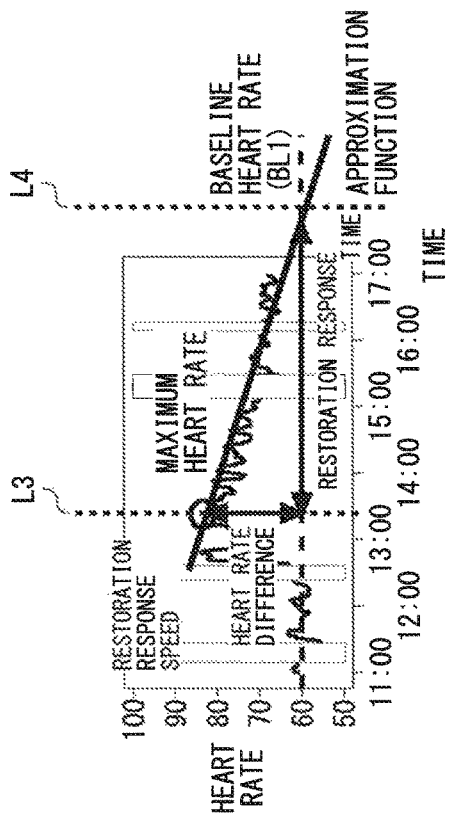
FIG. 53 and FIG. 54 are explanatory diagrams of calculating a restoration response time of the second peak.

FIG. 53 illustrates a relation between the maximum heart rate (P2) of the second peak, the baseline heart rate (BL1) and the restoration response time of the second peak, which is approximated by the linear function. A broken line L3 parallel to the axis of ordinates in FIG. 53 indicates the reaching time of the maximum heart rate (P1) of the first peak, and a broken line L4 indicates the time when the linear function of the restoration response speed of the second peak intersects the baseline heart rate (BL1). A solid line marked with arrows at both ends in parallel to the axis of ordinates indicates a difference between the baseline heart rate (BL1) and the maximum heart rate (P2) of the second peak, and a solid line marked with arrows at both ends in parallel to the axis of abscissa indicates the restoration response time of the second peak.

As illustrated in FIG. 53, the restoration response time of the second peak is calculated as a value (time) obtained by dividing the difference between the baseline heart rate (BL1) and the maximum heart rate (P2) of the second peak by the gradient parameter "α" of the approximation function (the linear function).

The sensor equipment 11 calculates the baseline heart rate (BL1) as explained in the process of S22 in FIG. 29. Then, the sensor equipment 11 calculates the difference between the maximum heart rate (P2) of the second peak calculated in the process of S56 and the baseline heart rate (BL1). The sensor equipment 11 calculates the restoration response time of the second peak by dividing the heart rate difference calculated above by the gradient parameter "α" calculated in the process of S58.

In the example of FIG. 53, the maximum heart rate (P2) of the second peak is "83.7 (bpm)"; the baseline heart rate (BL1) is "59.0 (bpm)"; and the heart rate difference is "24.7 (bpm)". Further, the gradient parameter "α" of the linear function to approximate the restoration response speed of the second peak is "−6.4 (bpm/hour)", and the restoration response time of the second peak is calculated at "231.5 (min)" by "(Heart Rate Difference)/(Gradient Parameter "α")".

The sensor equipment 11 temporarily stores, in a predetermined location of the main storage unit 92, the restoration response time of the second peak that is calculated in the process of S59 by being associated with the time zone of the meal and the identifying information of the sensor equipment 11.

The eleven characteristic quantities of four categories, which are calculated in the processes of FIGS. 28-32, are output as the meal characteristic quantity table illustrated in FIG. 26 to the network N. In the meal characteristic quantity table illustrated in FIG. 26, the calculated eleven characteristic quantities of four categories are registered by being associated with the categories of the meal characteristic quantities.

A value "0.82" calculated in the processes of S21-S25 in FIG. 29 is registered in the field of "area size ratio" of the meal characteristic quantity table illustrated in FIG. 26. Similarly, a value "85.2" calculated in the process of S32 in FIG. 30 is registered in the field of "first peak amplitude", and a value "83.7" calculated in the process of S33 is registered in the field of "second peak amplitude".

Similarly, a value "75.3" calculated in the process of S43 in FIG. 31 is registered in the field of "first peak rising response speed", and a value "−34.4" calculated in the process of S44 is registered in the field of "second peak restoration response speed". Moreover, a value "17.1" calculated in the process of S46 in FIG. 31 is registered in the field of "second peak rising response speed", and a value "−6.4" calculated in the process of S47 is registered in the field of "second peak restoration response speed".

Similarly, a value "7" calculated in the process of S53 in FIG. 32 is registered in the field of "first peak rising response time", and a value "45.7" calculated in the process of S55 is registered in the field of "first peak restoration response time". Moreover, a value "27" calculated in the process of S57 in FIG. 32 is registered in the field of "second peak rising response time", and a value "231.5" calculated in the process of S59 is registered in the field of "second peak restoration response time".

Note that the categories of the meal characteristic quantities calculated by the sensor equipment 11 are set per sensor equipment 11 beforehand as described in FIG. 28. Consequently, the meal characteristic quantities not being processed by the sensor equipment 11 are output to the network N so that the storage fields of the records of the relevant meal characteristic quantities are each in a null status.

(Subject Person Narrowing Process)

A subject person narrowing process in S10 illustrated in FIG. 27 will hereinafter be described with reference to the flowchart depicted in FIG. 33. In the subject person narrowing process illustrated in FIG. 33, the information processing apparatus 10 checks the meal characteristic quantities output from the sensor equipment 11 with the meal characteristic quantities of the plurality of candidates, which are previously registered in the meal characteristic quantity DB 201. For example, the information processing apparatus 10 determines whether values of the meal characteristic quantities output from the sensor equipment 11 fall within the unique range of the meal characteristic quantities of each candidate, which are registered in the meal characteristic quantity DB 201. Made is the determination for every characteristic quantity about whether the values of the meal characteristic quantities output from the sensor equipment 11 fall within the unique range of the meal characteristic quantities of each candidate, which are registered in the meal characteristic quantity DB 201. The information processing apparatus 10 narrows down the candidates who can be deemed to be the subject persons of the meal characteristic quantities detected by the sensor equipment 11 from within the plurality of candidates on the basis of a result of the checking with the unique range of the meal characteristic quantities with respect to all of the candidates registered previously in the meal characteristic quantity DB 201. Note that the meal characteristic quantities output from the sensor equipment 11 will be referred to also as "observation characteristic quantities" in the following discussion.

Figure 33:
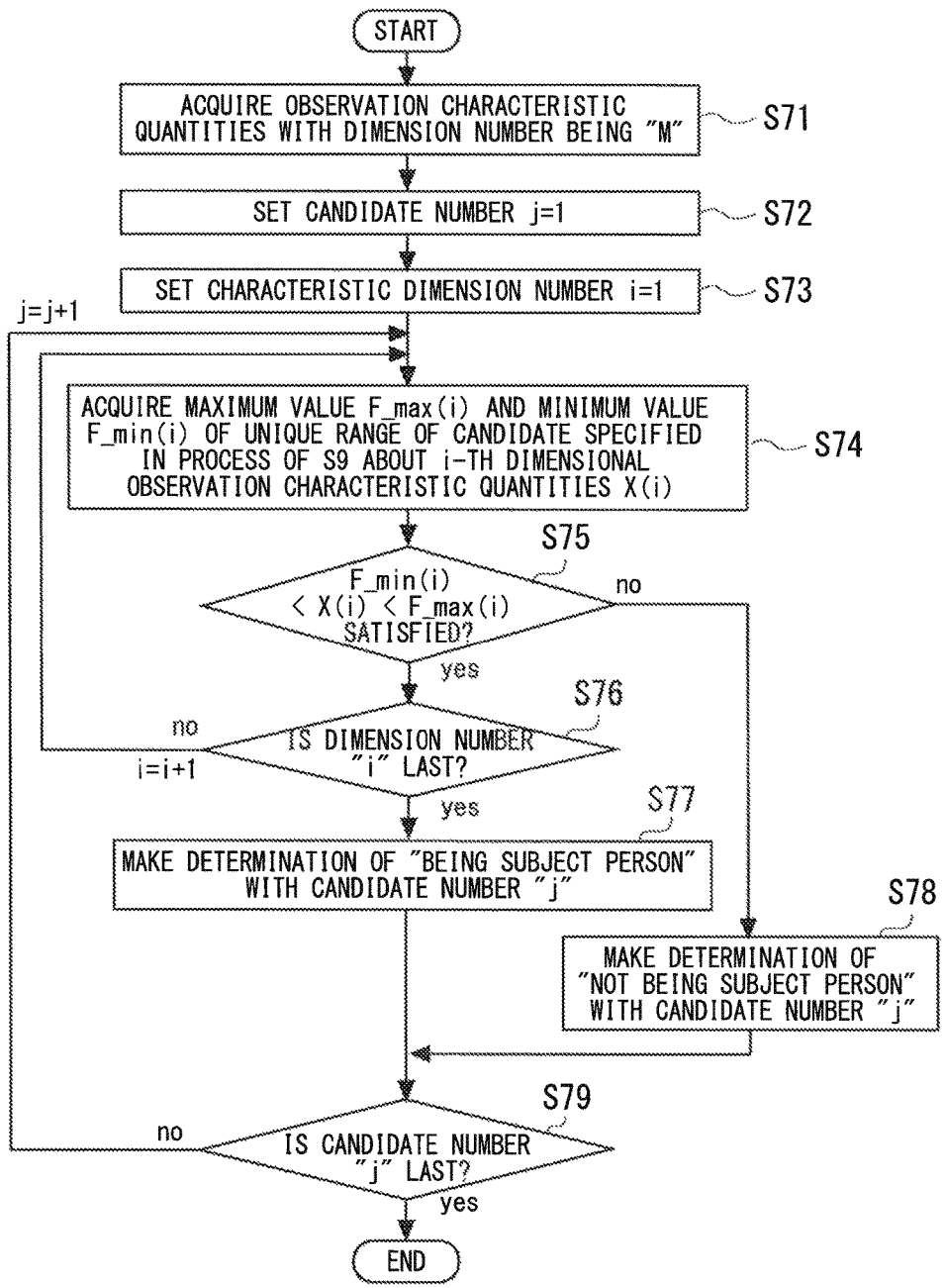
FIG. 33 is a flowchart of a subject person narrowing process in S10 of FIG. 27.

In the flowchart illustrated in FIG. 33, in a process of S71, the information processing apparatus 10 acquires the meal characteristic quantities (observation characteristic quantities) output from the sensor equipment 11 in the process of S7 in FIG. 27. The observation characteristic quantities contain the time zone of the meal and the identification number of the sensor equipment 11. Note that the observation characteristic quantities acquired in the process of S71 have eleven categories (dimensions) at the maximum, and the sensor equipment 11 sets the number of categories. A numerical quantity of the observation characteristic quantities acquired in the process of S71 is designated by "M(1-11)". The information processing apparatus 10 temporarily stores the acquired observation characteristic quantities in a predetermined location of the main storage unit 92.

In the process of S72, the information processing apparatus 10 sets the identification number (j=1 . . . N, where "N" is the number of candidates) for executing the narrowing process for the individual candidates with the unique range of the meal characteristic quantities being specified in the process of S9 illustrated in FIG. 27. In the process of S73, the information processing apparatus 10 sets the identification number (i=1–M≤11) for narrowing down each category of the meal characteristic quantity. The information processing apparatus 10 narrows down the candidate who can be deemed as the subject persons about the observation characteristic quantities from within the plurality of candidates by repeating the processes in S74-S79 per candidate and per characteristic quantity.

In the process of S74, the information processing apparatus 10 acquires the unique range of the candidate "j" with the unique range of the meal characteristic quantities being determined in the process of S9 in FIG. 27 with respect to an i-th dimensional observation characteristic quantities: X(i) in M-th dimensional observation characteristic quantities acquired in the process of S71. For example, let "F_max(i)" be the maximum value and "F_min(i)" be the minimum value of the unique range of the meal characteristic quantities. The information processing apparatus 10 acquires the maximum value "F_max(i)" and the minimum value "F_min(i)" of the i-th dimensional observation characteristic quantities of the candidate "j".

In the process of S75, the information processing apparatus 10 makes a comparison between a magnitude of each of the maximum value "F_max(i)" and the minimum value "F_min(i)" of the i-th dimensional meal characteristic quantities of the candidate "j" and a magnitude of the i-th dimensional observation characteristic quantities "X(i)", thereby determining whether a relation of "F_min(i)<X(i)<F_max(i)" is satisfied.

When the relation of "F_min(i)<X(i)<F_max(i)" is satisfied as a result of the comparison between magnitude of the observation characteristic quantities "X(i)" and the magnitude of the i-th dimensional meal characteristic quantities of the candidate "j" (S75, yes), the information processing apparatus 10 shifts the processing to S76. Whereas when the relation of "F_min(i)<X(i)<F_max(i)" is not satisfied as a result of the comparison between magnitude of the observation characteristic quantities "X(i)" and the magnitude of the i-th dimensional meal characteristic quantities of the candidate "j" (S75, no), the information processing apparatus 10 shifts to the process in S79.

In the process of S76, the information processing apparatus 10 determines whether the i-th dimension of the processing target meal characteristic quantities is the last dimension. When the i-th dimension of the meal characteristic quantities is not the last dimension (S76, no), the information processing apparatus 10 increments the i-th dimension of the processing target meal characteristic quantities by "1", and shifts to the process in S74. Whereas when the i-th dimension of the meal characteristic quantities is the last dimension (S76, yes), the information processing apparatus 10 shifts to the process in S77, then determines that the candidate "j" is the "subject person", and further shifts to the process in S79.

In the process of S79, the information processing apparatus 10 determines whether the processing target candidate "j" is the last candidate. The information processing apparatus 10, when the processing target candidate "j" is not the last candidate (S79, no), increments an identifier "j" of the processing target candidate, and shifts to the process in S74. Whereas when the processing target candidate "j" is the last candidate (S79, yes), the information processing apparatus 10 temporarily stores the candidate "j" determined to be the "subject person" in a predetermined location of the main storage unit 92, and finishes the subject person narrowing process.

The information processing apparatus 10 outputs, upon being triggered by finishing the subject person narrowing process illustrated in FIG. 33, all of the candidates determined to be the "subject persons" to the output unit 95 of the information processing apparatus 10 by being associated with the identification number and other equivalent information of the sensor equipment 11.

As described above, the sensor equipment 11 according to the embodiment calculates the heart rate characteristics associated with the meal as the eleven characteristic quantities of four categories, and is thereby enabled to specify the transition of the variation of the heart rate pertaining to the meal.

The sensor equipment 11 according to the embodiment obtains the area size ratio between the first peak area and the second peak area, whereby the activity load ratio between the peristaltic movement and the digestive activity pertaining to the meal unique to the candidate can be transformed into the numerical values. Further, the sensor equipment 11 according to the embodiment obtains the maximum heart rate of the first peak and the maximum heart rate of the second peak, and is thereby enabled to specify and transform the variation width of the heart rate pertaining to the meal unique to the candidate into the numerical value.

The sensor equipment 11 according to the embodiment obtains the rising response speed of the first peak, and is thereby enabled to specify and transform the rising variation of the heart rate due to the peristaltic movement pertaining to the meal unique to the candidate. The sensor equipment 11 according to the embodiment further obtains the restoration response speed of the first peak, and is thereby enabled to specify and transform the restoration variation of the heart rate due to the peristaltic movement pertaining to the meal unique to the candidate.

The sensor equipment 11 according to the embodiment obtains the rising response speed of the second peak, and is thereby enabled to specify and transform the rising variation of the heart rate due to the digestive activity pertaining to the meal unique to the candidate into the numerical value. Further, the sensor equipment 11 according to the embodiment obtains the restoration response speed of the second peak, and is thereby enabled to specify and transform the restoration variation of the heart rate due to the digestive activity pertaining to the meal unique to the candidate into the numerical value.

The sensor equipment 11 according to the embodiment obtains the rising response time of the first peak, and is thereby enabled to specify and transform transition time of the rising variation of the heart rate due to the peristaltic movement pertaining to the meal unique to the candidate into the numerical value. Moreover, the sensor equipment 11 according to the embodiment obtains the restoration response speed of the first peak, and is thereby enabled to specify and transform the transition time of the restoration variation of the heart rate due to the peristaltic movement pertaining to the meal unique to the candidate into the numerical value.

The sensor equipment 11 according to the embodiment obtains the rising response time of the second peak, and is thereby enabled to specify and transform transition time of the rising variation of the heart rate due to the digestive activity pertaining to the meal unique to the candidate into the numerical value. Moreover, the sensor equipment 11 according to the embodiment obtains the restoration response speed of the second peak, and is thereby enabled to specify and transform the transition time of the restoration variation of the heart rate due to the digestive activity pertaining to the meal unique to the candidate into the numerical value.

The sensor equipment 11 according to the embodiment transforms the eleven meal characteristic quantities of four categories into the numerical values, and is thereby enabled to quantitatively process the transition of variation of the heart rate pertaining to the meal unique to the candidate. For example, the information processing apparatus 10 according to the embodiment associates continuous variation widths of the transformed numerical values of the eleven meal characteristic quantities of four categories with the maximum values and the minimum values of the respective sets of meal characteristic quantities, and can thus specify the meal characteristic quantities as the unique range of every candidate. The information processing apparatus 10 according to the embodiment checks the unique range of the meal characteristic quantities specified per candidate with the observation characteristic quantities detected by the sensor equipment 11, and is thereby enabled to narrow down the candidates who can be deemed to be the subject persons for the observation characteristic quantities from within the plurality of candidates. As a result, the embodiment enables the provision of a technology of improving extraction accuracy of the candidates who can be deemed to be the subject persons from within the plurality of candidates.

Modified Example 1

The subject person narrowing process using the characteristics of heartbeats pertaining to the meal can be combined with the subject person specifying method using other biological features. It is feasible to combine, e.g., a subject person specifying method using the resting heart rate, a subject person specifying method using the electrocardiographic waveforms, and a subject person specifying method using motion characteristics instanced by walking characteristics and a positional history.

Figure 34:
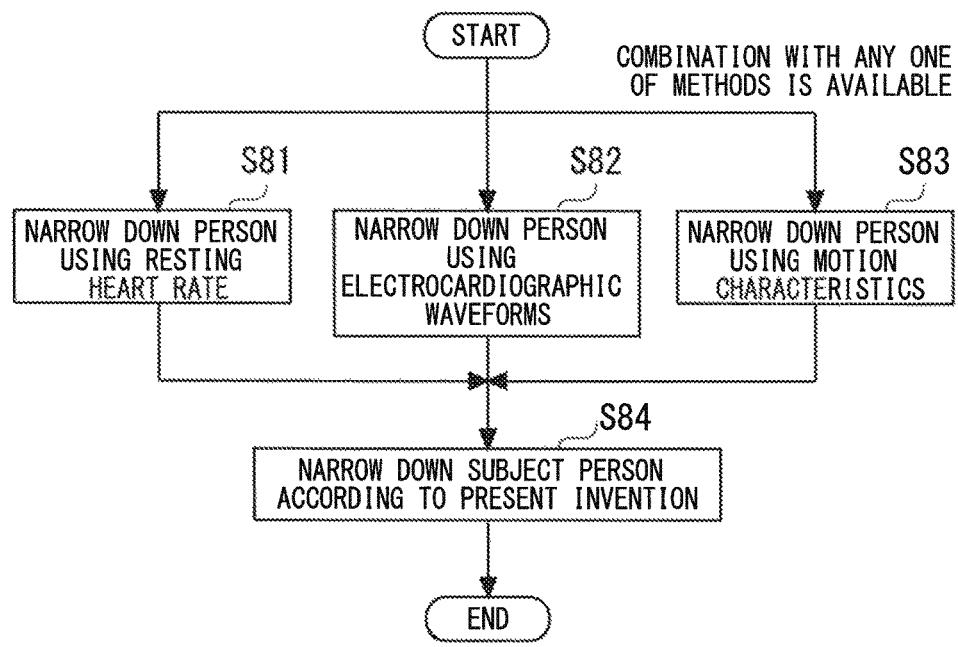
FIG. 34 is a flowchart of processes in a modified example 1.

FIG. 34 illustrates a flowchart of the subject person specifying process in a first modified example (modified example 1). FIG. 34 illustrates an example in which the subject person specifying method using other biological features is attained by combining the subject person specifying method using the resting heart rate, the subject person specifying method using the electrocardiographic waveforms, and the subject person specifying method using the motion characteristics instanced by the walking characteristics and the positional history. In a process of S84 in FIG. 34, the subject person specifying process illustrated in FIGS. 27-33 is executed properly corresponding to the characteristic quantities of the heartbeats pertaining to the meal of the subject person.

The subject person narrowing process in the modified example 1 involves narrowing down the candidates by using the resting heart rates of the plurality of candidates (S81). The information processing apparatus 10 narrows down the subject persons using the characteristics of the heartbeats pertaining to the meal (S84). Similarly, the information processing apparatus 10 narrows down the candidates by using the electrocardiographic waveforms (S82), or alternatively narrows down the candidates by using the motion characteristics (S83). Then, the information processing apparatus 10 narrows down the subject persons by using the characteristics of the heartbeats pertaining to the meal according to the embodiment.

It can be expected in the subject person narrowing process in the modified example 1 to improve the accuracy of narrowing down the candidates owing to increased characteristic quantities having different natures by use of other biological features. Further, owing to the use of other biological features, it can be expected to restrain intentional impersonation of the candidate because of combining a plurality of biological features.

Modified Example 2

The sensor equipment 11 is configured to include processing functions of a candidate unique range generating unit 103 and a subject person narrowing unit 104 of the information processing apparatus 10 illustrated in FIG. 21, and is thereby enabled to execute the subject person specifying process.

Figure 67:
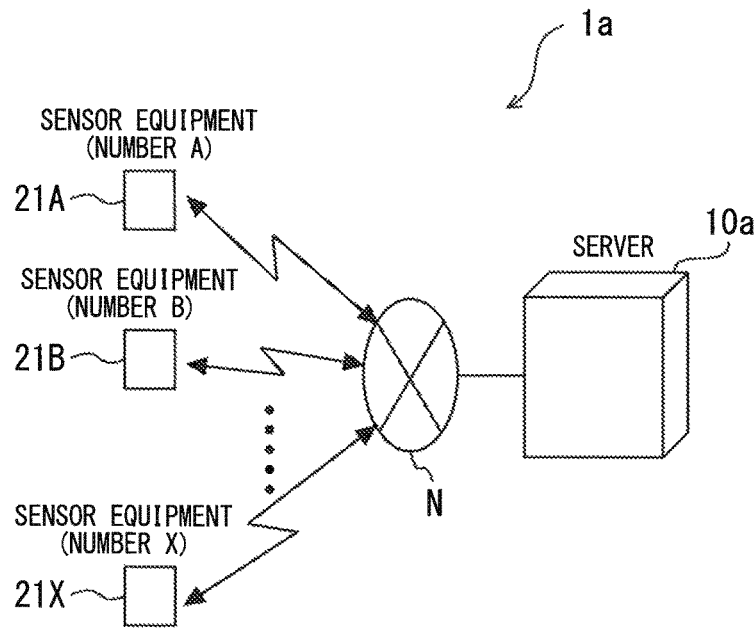
FIG. 67 is a diagram illustrating an information processing system in a modified example 2.
Figure 68:
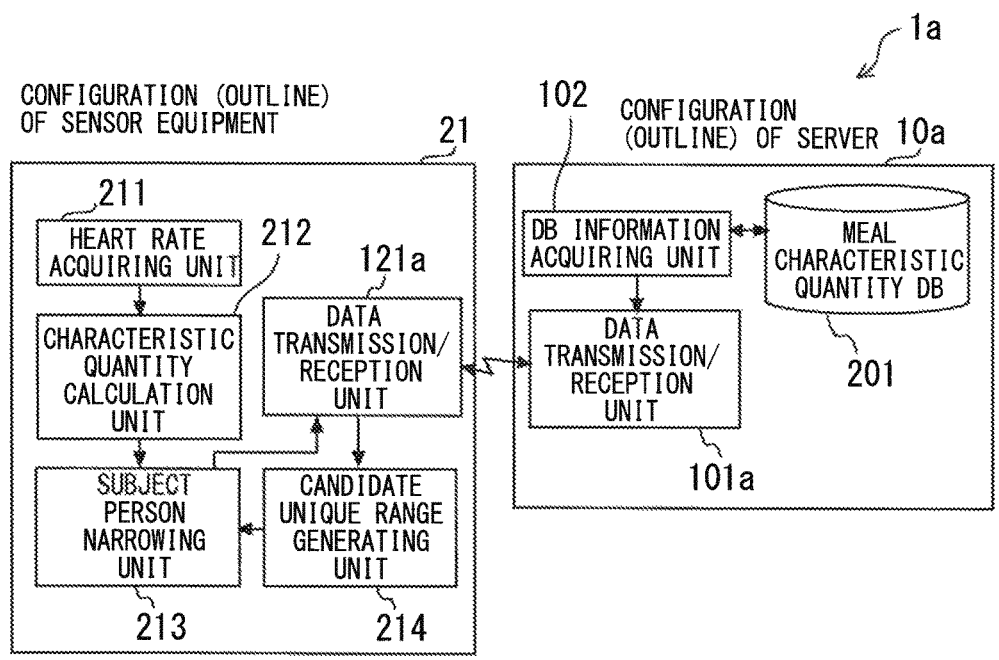
FIG. 68 is an explanatory diagram of a configuration of functions of the information processing system in the modified example 2.

FIGS. 67 and 68 illustrate an embodiment of a second modified example (modified example 2) including processing functions of the candidate unique range generating unit 103 and the subject person narrowing unit 104 on the side of the sensor equipment. In an information processing system 1a in the modified example 2 illustrated in FIG. 67, for example, sensor equipments 21 (21A, 21B, . . . , 21X) worn to a plurality of patients and other equivalent persons and an information processing apparatus 10a instanced by a server and other equivalent apparatuses are interconnected via the network N. The information processing apparatus 10a includes the DB information acquiring unit 102 and the meal characteristic quantity DB 210 illustrated in FIG. 21. Note that the sensor equipment 21 is allocated with an identification number (numbers A, B, . . . , X) or other equivalent numbers for uniquely identifying the wearer of the sensor equipment 21.

FIG. 68 illustrates an explanatory diagram of processing blocks of the information processing apparatus 10a and the sensor equipment 21 of the information processing system 1a. In the example of FIG. 68, the information processing apparatus 10a includes processing units, i.e., a data transmission/reception unit 101a and the DB information acquiring unit 102, and further includes the meal characteristic quantity DB 201 in the auxiliary storage unit 13. The meal characteristic quantity DB 201 stores the history values of the meal characteristic quantities per patient.

The data transmission/reception unit 101a illustrated in FIG. 68 receives, as established items of data, the various categories of characteristic quantities of the patient and other equivalent persons narrowed down by the sensor equipment 21, and periodically transmits a history of the various categories of characteristic quantities per patient to the sensor equipment 21, these characteristic quantities being acquired by the DB information acquiring unit 102. Note that the history of the various categories of characteristic quantities per patient is transmitted at an interval of, e.g., the time zone of the meal.

In the example of FIG. 68, the sensor equipment 21 includes respective processing units, i.e., a heart rate acquiring unit 211, a characteristic quantity calculation unit 212, a subject person narrowing unit 213, a candidate unique range generating unit 214, and a data transmission/reception unit 121a.

The heart rate acquiring unit 211 in FIG. 68 corresponds to, e.g., the sensor wearing determination unit 111, the heart rate data acquiring unit 112, the acceleration data acquiring unit 113, the exercise period determination unit 114, the meal period determination unit 115, and the noise heart rate eliminating unit 116 of the sensor equipment 11 illustrated in FIG. 21. Further, the characteristic quantity calculation unit 212 corresponds to, e.g., the area size characteristic quantity calculation unit 117, the amplitude characteristic quantity calculation unit 118, the speed characteristic quantity calculation unit 119, and the time characteristic quantity calculation unit 120 of the sensor equipment 11 illustrated in FIG. 21.

The subject person narrowing unit 213 in FIG. 68 corresponds to the subject person narrowing unit 104 provided in the information processing apparatus 10 illustrated in FIG. 21, and the candidate unique range generating unit 214 similarly corresponds to the candidate unique range generating unit 103 provided in the information processing apparatus 10 illustrated in FIG. 21. Note that the data transmission/reception unit 121a transmits, as the established items of data, the various categories of characteristic quantities of the patient and other equivalent persons narrowed down to the information processing apparatus 10a, and periodically receives the history of the various categories of characteristic quantities per patient, the history of the characteristic quantities being transmitted from the information processing apparatus 10a. The received history of various categories of characteristic quantities per patient is temporarily stored in a predetermined location of the main storage unit 92.

The candidate unique range generating unit 214 of the sensor equipment 21 generates the unique range per characteristic quantity on the basis of the history of various categories of characteristic quantities per patient, the history being periodically transmitted from the information processing apparatus 10a. Furthermore, the characteristic quantities unique to the patients wearing the sensor equipments 21 corresponding to the eleven characteristic quantities of four categories of the heart rates pertaining to the meals, are specified by processes of the heart rate acquiring unit 211 and the characteristic quantity calculation unit 212 of the sensor equipment 21.

The sensor equipment 21 checks the characteristic quantities unique to the wearer with the unique range per characteristic quantity, which is generated based on the history of various categories of characteristic quantities per patient, thereby determining whether the wearer of the sensor equipment 21 is the true wearer. Note that when the wearer of the sensor equipment 21 is the true wearer, the sensor equipment 21 transmits, to the information processing apparatus 10a, the eleven characteristic quantities of four categories of the heart rates pertaining to the meals specified by being associated with the time zones of the meals. The information processing apparatus 10a updates the data of the meal characteristic quantity DB 201, based on the eleven characteristic quantities of four categories transmitted from the sensor equipment 21.

As described above, the sensor equipment 21 in the modified example 2 illustrated in FIGS. 67 and 68 enables the target server specifying process on the side of the sensor equipment 21, thereby making it possible to determine whether the wearer of the sensor equipment 21 is the true wearer.

Modified Example 3

Figure 69:
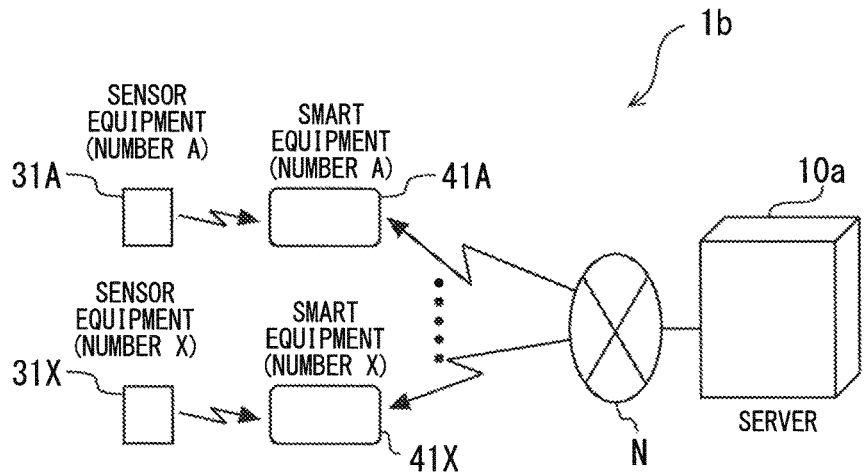
FIG. 69 is a diagram illustrating the information processing system in a modified example 3.
Figure 70:
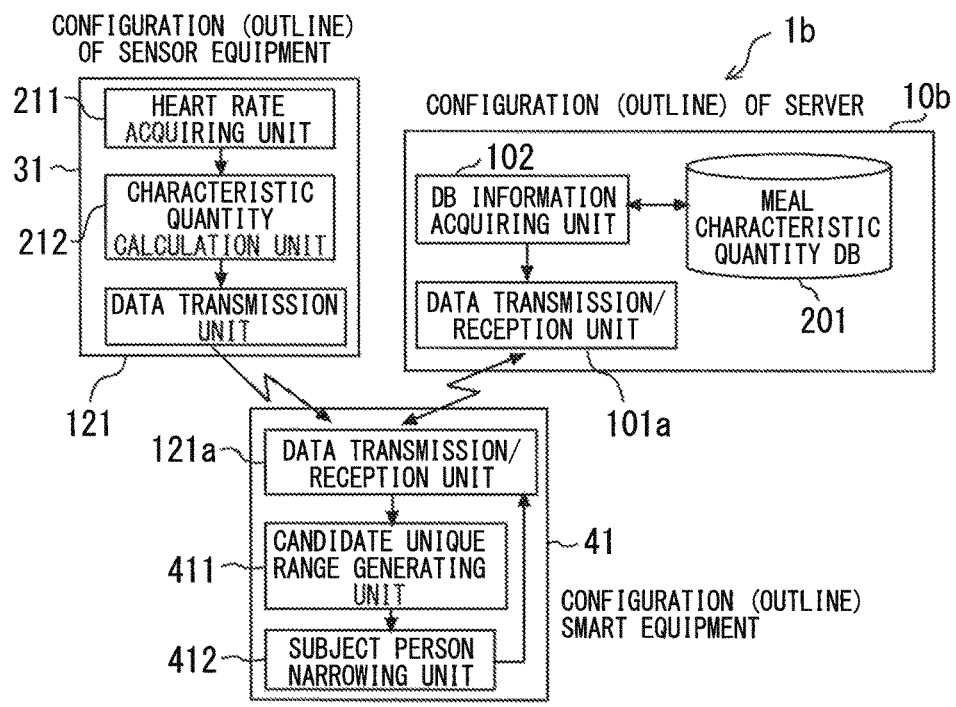
FIG. 70 is an explanatory diagram of a configuration of functions of the information processing system in a modified example 3.

An available mode of the information processing system executing the subject person specifying process based on the eleven characteristic quantities of four categories of the heart rates pertaining to the meals, is a mode including an information processing equipment 41 instanced by a smartphone illustrated in FIGS. 69 and 70. Herein, the information processing equipment 41c can be exemplified by a tablet PC (Personal Computer), a PDA (Personal Data Assistance), a notebook PC and other equivalent equipments other than the smartphone.

For example, such a mode is assumed that the information processing equipment provided on a bed and other equivalent facilities used by the patients and other equivalent person manages the characteristic quantities of the heart rates pertaining the meals, the characteristic quantities being acquired by the sensor equipments worn to the patients and other equivalent persons. An information processing system 1b illustrated in FIGS. 69 and 70 is an exemplification of an embodiment of the modified example 3 including the sensor equipment worn to the patient, the information processing equipment (smart equipment) provided on the bed and other equivalent facilities and an information processing apparatus 10b to manage the characteristic quantities pertaining to the meals per patient.

In the information processing system 1b according to the modified example 3 illustrated in FIG. 69, a sensor equipment 31 and the information processing equipment 41 establish a one-to-one connection via communication functions thereof. The sensor equipment 31 and the information processing equipment 41 are allocated with identification numbers (numbers A, B, . . . , X) for uniquely identifying the wearer of the sensor equipment 31. The plurality of information processing equipments 41 (41A, . . . , 41X) and an information processing apparatus 10b instanced by the server and other equivalent apparatuses are interconnected via the network N. The information processing equipment 41 can execute the subject person specifying process for the patient and other equivalent persons wearing the sensor equipments 31 by including the processing functions of the candidate unique range generating unit 103 and the subject person narrowing unit 104 of the information processing apparatus 10 illustrated in FIG. 21.

FIG. 70 illustrates an explanatory diagram of processing blocks of the information processing apparatus 10b, the sensor equipment 31 and the information processing equipment 41 of the information processing system 1b. In the example of FIG. 70, the information processing apparatus 10b includes processing units, i.e., the data transmission/reception unit 101a and the DB information acquiring unit 102, and further includes the meal characteristic quantity DB 201 in the auxiliary storage unit 13. The meal characteristic quantity DB 201 stores the history values of the meal characteristic quantities per patient.

The data transmission/reception unit 101a illustrated in FIG. 70 receives, as established items of data, the various categories of characteristic quantities of the patient and other equivalent persons narrowed down on the side of the information processing equipment 41, and periodically transmits a history of the various categories of characteristic quantities per patient to the information processing equipment 41, these characteristic quantities being acquired by the DB information acquiring unit 102. The history of the various categories of characteristic quantities per patient is transmitted at an interval of, e.g., the time zone of the meal.

In the explanatory diagram of FIG. 70, the sensor equipment 31 includes the heart rate acquiring unit 211 and the characteristic quantity calculation unit 212 illustrated in FIG. 70, and further includes the data transmission unit 121 depicted in FIG. 21. The sensor equipment 31 specifies the characteristic quantities unique to the patients wearing the sensor equipments 31 corresponding to the eleven characteristic quantities of four categories of the heart rates pertaining to the meals through the processes of the heart rate acquiring unit 211 and the characteristic quantity calculation unit 212, and transmits the specified characteristic quantities to the information processing equipment 41.

The information processing equipment 41 includes respective processing units, i.e., a candidate unique range generating unit 411, a subject person narrowing unit 412, and the data transmission/reception unit 121a illustrated in FIG. 68. the data transmission/reception unit 121a transmits, as the established items of data, the various categories of characteristic quantities of the patient and other equivalent persons narrowed down to the information processing apparatus 10b, and periodically receives the history of the various categories of characteristic quantities per patient, the history of the characteristic quantities being transmitted from the information processing apparatus 10b. The received history of various categories of characteristic quantities per patient is temporarily stored in a predetermined location of the main storage unit 92. Note that the data transmission/reception unit 121a receives the characteristic quantities unique to the patient, which are transmitted from the sensor equipment 31 connected via the communication function, and temporarily stores the received characteristic quantities in a predetermined location of the main storage unit 92.

The candidate unique range generating unit 411 corresponds to the candidate unique range generating unit 103 provided in the information processing apparatus 10 illustrated in FIG. 21, and similarly the subject person narrowing unit 412 corresponds to the subject person narrowing unit 104 provided in the information processing apparatus 10 illustrated in FIG. 21. The candidate unique range generating unit 411 of the information processing equipment 41 generates the unique range per characteristic quantity, based on the history of various categories of characteristic quantities per patient, which are periodically transmitted from the information processing apparatus 10b.

The information processing equipment 41 checks the characteristic quantities unique to the patient, which are received from the sensor equipment 31, with the unique range per characteristic quantity, the unique range being generated based on the history of various categories of characteristic quantities per patient, which are received from the information processing apparatus 10b. The information processing equipment 41 determines whether the wearer of the sensor equipment 31 is the true wearer. Note that when the wearer of the sensor equipment 31 is the true wearer, the information processing equipment 41 transmits, to the information processing apparatus 10b, the eleven characteristic quantities of four categories of the heart rates pertaining to the meals specified by being associated with the time zones of the meals. The information processing apparatus 10b updates the data of the meal characteristic quantity DB 201, based on the eleven characteristic quantities of four categories transmitted from the information processing equipment 41.

As described above, the information processing equipment 41 in the modified example 3 illustrated in FIGS. 69 and 70 is enabled to execute the subject person specifying process based on the eleven characteristic quantities of four categories transmitted from the sensor equipment 31, and can determine whether the wearer of the sensor equipment 31 is the true wearer.

Experimental Example

An experimental example of narrowing down the subject person by use of the eleven characteristic quantities of four categories of the heart rates pertaining to the meals, which are acquired from the four candidates, will hereinafter be described with reference to FIGS. 57-66. The four candidates, who are all males in distinction of sex, are a candidate A (in his early 30s in age), a candidate B (in his 50s), a candidate C (in his 40s), and a candidate D (in his late 30s). The time zone of the meal is set at the lunch (11:00-17:00), and the data of the heart rates pertaining to the meals for about 12 days per candidate are acquired while varying eating conditions instanced by an eating speed, a content of the meal (a degree of load on digestion) and a meal quantity.

FIGS. 57-60 illustrate examples of the heart rate data acquired from the candidates A-D. FIGS. 57-60 are graphs of the transition of the heart rate in the time zone at the lunch, in which the axis of ordinates indicates the heart rate (bpm) per unit time, while the axis of abscissa indicates the elapse time (the period of time). The heart rate data illustrated in FIGS. 57-60 examples. Note that a period interposed by broken lines parallel to the axis of ordinates represents the meal period.

As depicted in FIGS. 57-60, the peak (the first peak) of the heart rate occurs per candidate in the meal period interposed by the broken lines. When overlooking the transition of the heart rate of each candidate as illustrated in FIGS. 57-60, it is recognized that there exists an individual difference between the transitions of the heart rates. For instance, it is understood that the heart rates of the candidates C and D transition at a relatively high level (e.g., 70 (bpm) or higher), while the heart rate of the candidate B transitions at a relatively low level (e.g., 70 (bpm) or lower). It is also recognized that the transition of the heart rate of the candidate A exhibits a sharper variation than the transitions of the heart rates of other candidates.

Note that peaks Pb1, Pb2 of the heart rate occur anterior and posterior to the meal period indicated by the broken lines in the graph example of the candidate B. The occurrence of the peaks Pb1, Pb2 of the heart rate in the graph example of the candidate B is derived from walking exercises performed before and after the meal. Further in the graph example of the candidate B, a peak Pb3 of the heart rate with the peak value being in the vicinity of 90 (bpm) occurs in the postprandial period of "13:00-14:00". The occurrence of the peak Pb3 of the heart rate is derived from going up and down the stairs when the candidate B moves to a meeting room on another floor for attending the meeting.

Figure 58:
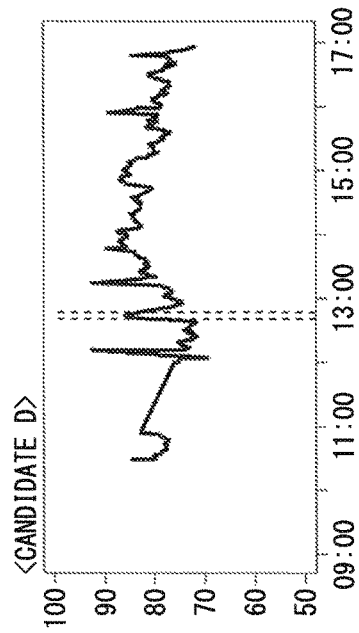
Figure 59:
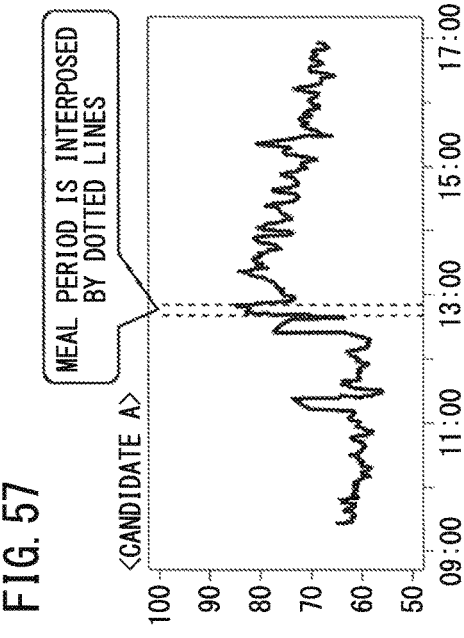
Figure 60:
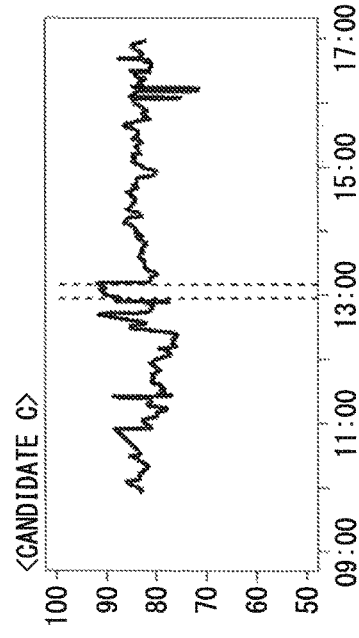

In order to eliminate influence, occurring in the heart rate data of the candidate B in FIG. 58, of the rise and receiver of the heart rate due to the kinetic activity, the sensor equipment 11 according to the embodiment executes the noise heart rate elimination process in S5 in the subject person specifying process illustrated in FIG. 27. The sensor equipment 11 according to the embodiment calculates the eleven meal characteristic quantities of four categories targeting on the heart rate data from which to have eliminated the influence of the rise and restoration of the heart rate due to the kinetic activity, and is thereby enabled to extract the characteristic quantities of the heartbeats pertaining to the meal.

The subject person specifying process according to the embodiment entails specifying the unique range based on the maximum value and the minimum value per meal characteristic quantity in the eleven meal characteristic quantities of four categories acquired per candidate. FIG. 61 illustrates a unique range (characteristic quantity range) list calculated from the eleven meal characteristic quantities of four categories acquired from the candidates in FIGS. 57, 58, 59 and 60. The information processing apparatus 10 according to the embodiment generates the unique range list of the meal characteristic quantities illustrated in FIG. 61 by executing the process in S9 depicted in FIG. 27.

In the unique range list illustrated in FIG. 61, the unique ranges calculated with respect to the candidates (persons) A and B in the experimental example are stored for each of the eleven meal characteristic quantities of four categories. Note that the unique range of every meal characteristic quantity is expressed by "[a, b]", in which a symbol "a" represents the maximum value and "b" designates the minimum value of the relevant meal characteristic quantities in the example of FIG. 61. Additionally, a target period for calculating the unique range is a period (12 days) for acquiring the meal characteristic quantities.

As indicated in the unique range list illustrated in FIG. 61, an area size ratio of the meal characteristic quantities of the candidate A is calculated at [0.62, 1.00]; a first peak amplitude (bpm) is calculated at [71.3, 92.1]; a first peak rising response time (min) is calculated at [4, 9.5]; a first peak rising response speed (bpm/hour) is calculated at [58.9, 86.3]; and a first peak restoration response time (min) is calculated at [31, 50]. Further, a first peak restoration response speed (bpm/hour) is calculated at [−43.7, −34.0]; a second peak amplitude (bpm) is calculated at [83.7, 91.1]; a second peak rising response time (min) is calculated at [27, 40]; and a second peak rising response speed (bpm/hour) is calculated at [11.2, 17.1]. Still further, a second peak restoration response time (min) is calculated at [156.5, 231.5]; and a second peak restoration response speed (bpm/hour) is calculated at [−10.7, −3.4].

With respect to the candidate B, the area size ratio of the meal characteristic quantities is calculated at [1.32, 1.60]; the first peak amplitude (bpm) is calculated at [62.1, 70.0]; the first peak rising response time (min) is calculated at [3, 9.5]; the first peak rising response speed (bpm/hour) is calculated at [50.3, 90.3]; and the first peak restoration response time (min) is calculated at [32, 38]. Further, the first peak restoration response speed (bpm/hour) is calculated at [−43.2, −29.5]; the second peak amplitude (bpm) is calculated at [57.1, 65.8]; the second peak rising response time (min) is calculated at [36, 50]; and the second peak rising response speed (bpm/hour) is calculated at [2.3, 5.6]. Still further, the second peak restoration response time (min) is calculated at [128.5, 421]; and the second peak restoration response speed (bpm/hour) is calculated at [−3.7, −0.7].

Figure 62:
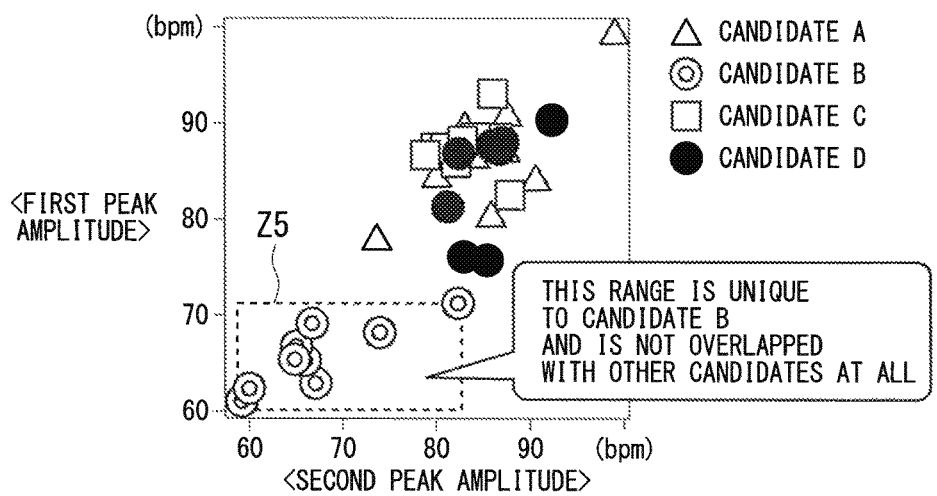
FIG. 62 is a diagram illustrating a plotted example using two sets of meal characteristic quantities.

FIG. 62 depicts a plotted example of the meal characteristic quantities of the candidates A-D by using the first peak amplitude and the second peak amplitude. FIG. 62 depicts the example of plotting samples containing the maximum values and the minimum values of the individual candidates, in which the axis of ordinates indicates the first peak amplitude (bpm), while the axis of abscissa indicates the second peak amplitude (bpm). In FIG. 62, the sample of the candidate A is marked with "Δ"; the sample of the candidate B is marked with "⊙"; the sample of the candidate C is marked with "□"; and the sample of the candidate D is marked with "●".

It is recognized in the example of FIG. 62 that the samples detected about the candidate B are grouped based on the first peak amplitude being in the vicinity of "70 (bpm)" or under and the second peak amplitude being in the vicinity of "80 (bpm)" or under. It is also recognized that the meal characteristic quantities of other candidates are not contained in the area Z5 configured by combining the unique range of the first peak amplitude (maximum value−minimum value) and the unique range of the second peak amplitude (maximum value−minimum value), which are detected about the candidate B.

In the combination of the meal characteristic quantities of the first and second peak amplitudes, the area Z5 configured by combining the unique ranges of the meal characteristic quantities detected about the candidate B, becomes a unique area to the candidate B. In other words, the candidate B can be narrowed down from within the individual candidates by using the unique range of the first peak amplitude and the unique range of the second peak amplitude of the individual candidates with respect to the detected meal characteristic quantities of the first and second peak amplitudes.

Figure 63:
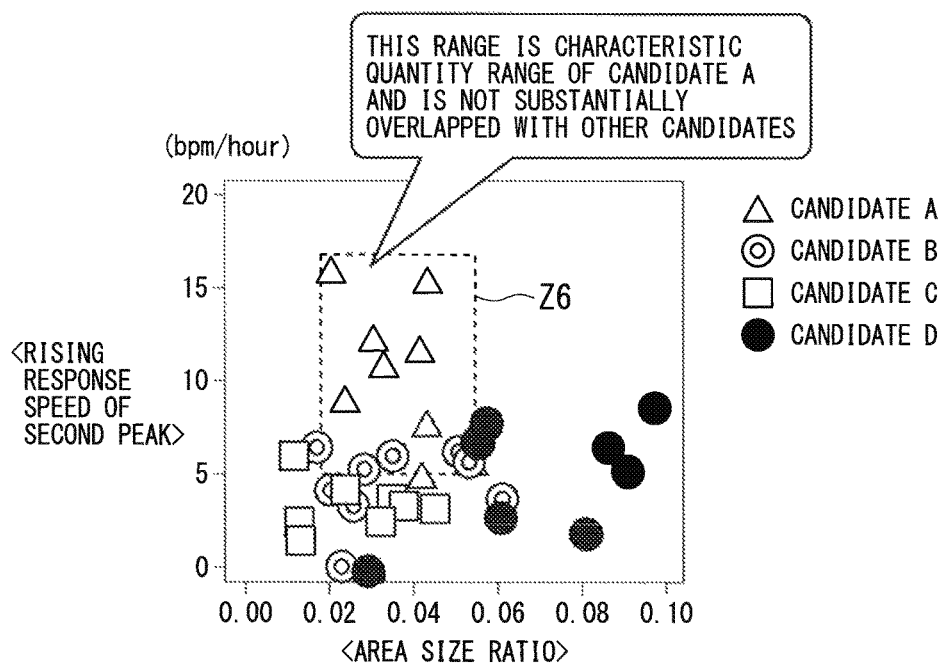
FIG. 63 is a diagram illustrating a plotted example using the two sets of meal characteristic quantities.

FIG. 63 illustrates a plotted example of the meal characteristic quantities about the candidates A-D by using the rising response speed of the second peak and the area size ratio. FIG. 63 illustrates the example of plotting the samples containing the maximum values and the minimum values of the individual candidates, in which the axis of ordinates indicates the second peak amplitude (bpm/hour), while the axis of abscissa indicates the area size ratio. The symbols representing the samples of the individual candidates in FIG. 63 are the same as the symbols in FIG. 62.

In the example of FIG. 63, it is understood that the samples detected about the candidate A are grouped into a range of the second peak rising response speed being in the vicinity of "5 (bpm/hour)" or higher and a range of the area size ratio being "in the vicinity of 0.02 but less than 0.06". An area Z6 configured by combining the unique range of the second peak rising response speed (maximum value−minimum value) and the area size ratio (maximum value−minimum value), which are detected about the candidate A, contains an area overlapped with the meal characteristic quantities of other candidates with the second peak rising response speed being in the vicinity of "5 (bpm/hour)". Other candidates overlapped with the area Z6 are the candidates B and D. The overlapped area between the candidates B and D is an edge portion of the area Z6, and hence, in the combination of the meal characteristic quantities related to the second peak rising response speed and the meal characteristic quantities related to the area size ratio, the area Z6 configured by combining the unique ranges of the meal characteristic quantities detected about the candidate B is said to be the unique area about the candidate B. It is feasible to narrow down the candidate A from within the individual candidates by using the unique range of the second peak rising response speed and the unique range of the area size ratio of each candidate with respect to the detected meal characteristic quantities related to the second peak rising response speed and the detected meal characteristic quantities related to the area size ratio.

Figure 64:
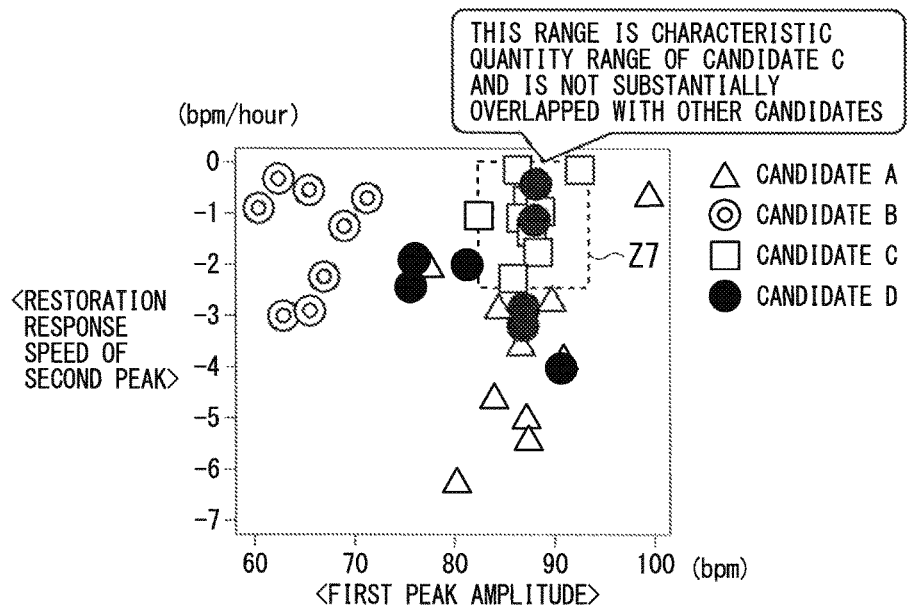
FIG. 64 is a diagram illustrating a plotted example using the two sets of meal characteristic quantities.

FIG. 64 illustrates a plotted example of the meal characteristic quantities about the candidates A-D by using the restoration response speed of the second peak and the first peak amplitude. FIG. 64 illustrates the example of plotting the samples containing the maximum values and the minimum values of the individual candidates, in which the axis of ordinates indicates the second peak restoration response speed (bpm/hour), while the axis of abscissa indicates the first peak amplitude (bpm). The symbols representing the samples of the individual candidates in FIG. 64 are the same as the symbols in FIG. 62.

In the example of FIG. 64, it is understood that the samples detected about the candidate C are grouped into a range of the second peak restoration response speed being in the vicinity of "−3 (bpm/hour)" or higher and a range of the first peak amplitude being "in the vicinity of 80 through 90 (bpm)". An area Z7 configured by combining the unique range of the second peak restoration response speed (maximum value−minimum value) and the first peak amplitude (maximum value−minimum value), which are detected about the candidate C, contains an area overlapped with the candidate D with the second peak restoration response speed being in the vicinity of "−2 (bpm/hour)" or higher. In the combination of the meal characteristic quantities related to the second peak restoration response speed and the meal characteristic quantities related to the first peak amplitude, the area Z7 has a substantially small area range, and hence the area Z7 configured by combining the unique ranges of the meal characteristic quantities detected about the candidate C is said to be the unique area about the candidate C. It is feasible to narrow down the candidate C from within the individual candidates by using the unique range of the second peak restoration response speed and the unique range of the first peak amplitude of each candidate with respect to the detected meal characteristic quantities related to the second peak restoration response speed and the detected meal characteristic quantities related to the first peak amplitude.

Figure 65:
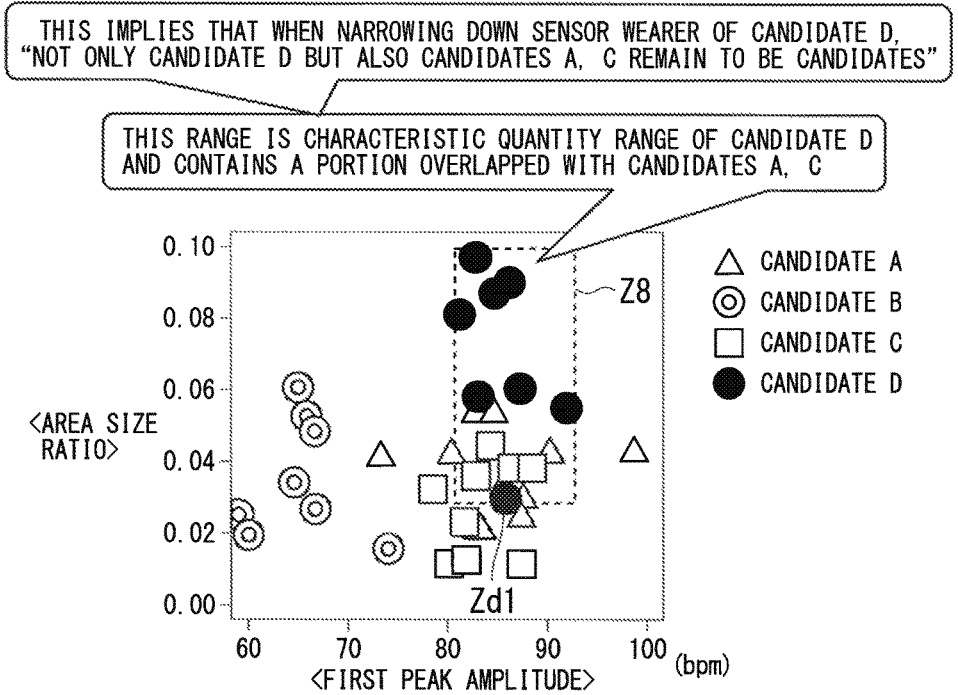
FIG. 65 is a diagram illustrating a plotted example using the two sets of meal characteristic quantities.

FIG. 65 illustrates a plotted example of the meal characteristic quantities about the candidates A-D by using the area size ratio and the first peak amplitude. FIG. 65 illustrates the example of plotting the samples containing the maximum values and the minimum values of the individual candidates, in which the axis of ordinates indicates the area size ratio, while the axis of abscissa indicates the first peak amplitude (bpm). The symbols representing the samples of the individual candidates in FIG. 65 are the same as the symbols in FIG. 62.

In the example of FIG. 65, it is understood that the samples detected about the candidate D are grouped into a range of the area size ratio being "in the vicinity of 0.03 through 0.10" and a range of the first peak amplitude being "in the vicinity of 80 through 90 (bpm)". An area Z8 configured by combining the unique range of the area size ratio (maximum value−minimum value) and the first peak amplitude (maximum value−minimum value), which are detected about the candidate D, contains an area overlapped with the candidates A, C in a range of the area size ratio being "in the vicinity of 0.03 but less than 0.06.

In the area Z8 about the candidate D, the samples exclusive of a sample Zd1 are grouped into a range of the area size ratio being "in the vicinity of 0.05" or larger. Therefore, in the combination of the meal characteristic quantities related to the area size ratio and the meal characteristic quantities related to the first peak amplitude, the area Z8 configured by combining the unique ranges of the meal characteristic quantities detected about the candidate D is said to be a unique area about the candidate D. It is feasible to narrow down the candidate D from within the individual candidates by using the unique range of the area size ratio and the unique range of the first peak amplitude of each candidate with respect to the detected meal characteristic quantities related to the area size ratio and the detected meal characteristic quantities related to the first peak amplitude.

The accuracy of narrowing down the candidates C and D can be improved by adding the unique range of the meal characteristic quantities related to the second peak rising response speed illustrated in FIG. 63 to the area size ratio and the first peak amplitude in FIG. 65. Further, the accuracy of narrowing down the candidates A and D can be improved by adding the unique range of the meal characteristic quantities related to the second peak amplitude illustrated in FIG. 62 to the area size ratio and the first peak amplitude in FIG. 65. It can be expected that the accuracy of narrowing down the candidates A, C and D can be improved by adding the unique ranges of the meal characteristic quantities related to the second peak rising response speed and the second peak amplitude to the area size ratio and the first peak amplitude in FIG. 65. As already described in the plotted examples of FIGS. 62-65, the accuracy of extracting the candidates who can be deemed to be the subject persons from within the plurality of candidates by the combinations (11 combinations at the maximum) of the unique ranges of the meal characteristic quantities specified about the individual candidates.

For example, such a mis-wearing case is assumed that a sensor equipment 67 to be worn to the patient A is mistakenly worn to the patient B, while a sensor equipment 11B to be worn to the patient B is mistakenly worn to the patient A as illustrated in FIG. 19. It is also assumed that the sensor equipment 11B outputs the meal characteristic quantities (observation characteristic quantities) illustrated in FIG. 26 to the network N. The information processing apparatus 10 narrows down the subject person about the observation characteristic quantities by determining a magnitude relation between the observation characteristic quantities illustrated in FIG. 26 and the unique ranges of the meal characteristic quantities acquired from the individual candidates A-D.

Figure 66:
FIG. 66 is a diagram illustrating an example of a narrowing result table in an experimental example.

FIG. 66 illustrates a table structured by adding the observation characteristic quantities in FIG. 26 to the characteristic quantity range list of the candidates illustrated in FIG. 61. In an example of the table in FIG. 66, the observation characteristic quantities illustrated in FIG. 26 are registered in a "observation characteristic quantity" column. The characteristic quantity range of the candidate A illustrated in FIG. 61 is registered in a "candidate A unique characteristic quantity range" column, and a characteristic quantity range of the candidate B is registered in a "candidate B unique characteristic quantity range" column. Moreover, a determination result of the magnitude relation between the meal characteristic quantity range of the candidate A and the observation characteristic quantities is registered in a "determination result of candidate A" column, and a determination result of the magnitude relation between the meal characteristic quantity range of the candidate B and the observation characteristic quantities is registered in a "determination result of candidate B" column.

In an example of the table in FIG. 66, the area size ratio of the observation characteristic quantity is "0.82", and the candidate A unique characteristic quantity range is "[0.62, 1.00]". The area size ratio of the observation characteristic quantity satisfies a relation of "0.62<0.82<1.00" defined as a determination condition of the process in S75 of FIG. 33. Consequently, in the information processing apparatus 10, the area size ratio of the observation characteristic quantity leads to a determination of being "candidate A", and a mark "○" is registered in a "candidate A determination result" field in FIG. 66.

On the other hand, a candidate B unique characteristic quantity range is "[1.32, 1.60]", and the area size ratio of the observation characteristic quantities becomes "0.82<1.32", which does not satisfy the determination condition of the process in S75 of FIG. 33. Consequently, in the information processing apparatus 10, the area size ratio of the observation characteristic quantity leads to a determination of not being "candidate B", and a mark "x" is registered in a "candidate B determination result" field in FIG. 66.

For example, the information processing apparatus 10 executes the aforementioned processes per meal characteristic quantity, and registers the determination results in a "candidate A determination result" field and a "candidate B determination result" field, respectively. As a result, as illustrated in FIG. 66, a mark "○" is registered in the "candidate A determination result" field associated with every meal characteristic quantity. Further, the mark "x" is registered in the "candidate B determination result" field associated with the meal characteristic quantities of the area size ratio, the first peak amplitude, the first peak restoration response time, the second peak amplitude, the second peak rising response speed and the second peak restoration response speed.

In the narrowing process executed by the information processing apparatus 10, when all of the characteristic quantities (eleven characteristic quantities at the maximum) observed on the sensor equipment 11 are contained in the characteristic quantity range of the candidate being processed in progress, the candidate can be determined to be the wearer (subject person) of the sensor equipment 11. In the example of FIG. 66, the information processing apparatus 10 can determine that the wearer of the sensor equipment 11, who has the observation characteristic quantities illustrated in FIG. 26, is the "candidate A".

The subject person specifying apparatus can improve the accuracy of specifying the individual based on the heart rate.

<<Computer Readable Non-Transitory Recording Medium>>

A program, for making a computer, other machines and apparatuses (which will hereinafter be referred to as the computer and other equivalent apparatuses) attain anyone of the functions, can be recorded on a non-transitory recording medium readable by the computer and other equivalent apparatuses. Then, the computer and other equivalent apparatuses are made to read and execute the program on this non-transitory recording medium, whereby the function thereof can be provided.

Herein, the non-transitory recording medium readable by the computer and other equivalent apparatuses connotes a non-transitory recording medium capable of accumulating information instanced by data, programs and other equivalent information electrically, magnetically, optically, mechanically or by chemical action, which can be read from the computer and other equivalent apparatuses. Among these non-transitory recording mediums, the mediums removable from the computer and other equivalent apparatuses are exemplified by a flexible disc, a magneto-optic disc, a CD-ROM, a CD-R/W, a DVD, a Blu-ray disc, a DAT, an 8 mm tape, and a memory card like a flash memory. Further, a hard disc, a ROM (Read-Only Memory) and other equivalent recording mediums are given as the non-transitory recording mediums fixed within the computer and other equivalent apparatuses.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An apparatus for specifying a person, comprising:
a processor; and
a memory configured to store a program causing the processor to execute:
acquiring characteristic quantity of variations of heart rate of a subject person related to a meal of the subject person generated from heart rate data of the subject person detected by a sensor and an identifier of the sensor, wherein the characteristic quantity is calculated from the heart rate data obtained for at least one of a first period and a second period, the first period containing a rise of heart rate of the subject person and the second period containing a rise of heart rate of the subject person immediately after the first period;
calculating a distribution range of history values of the characteristic quantity associated with a plurality of candidates;
extracting one of the plurality of candidates corresponding to the subject person from within the plurality of candidates, based on a relation between the generated characteristic quantity and the distribution range of the history values of the characteristic quantity; and
determining whether an identifier of a sensor associated with the one of the plurality of candidates is coincident with the identifier of the sensor or not, and outputting an alert when the identifier of the sensor associated with the one of the plurality of candidates is not coincident with the identifier of the sensor.

2. The apparatus according to claim 1, wherein the characteristic quantity is calculated from heart rate data obtained for the first period containing a time zone of the meal.

3. The apparatus according to claim 2, wherein the first period contains a predetermined period from meal start time up to when the heart rate finishes falling after rising posterior to the meal start time.

4. The apparatus according to claim 1, wherein the characteristic quantity is calculated from the heart rate data obtained for the second period containing a period immediately after the time zone of the meal.

5. The apparatus according to claim 4, wherein the second period contains a predetermined period from end time of the first period up to when the heart rate finishes falling after rising posterior to the end time.

6. The apparatus according to claim 4, wherein the characteristic quantity contains a total ratio of a total of heart rates for the first period of the subject person to a total of heart rates for the second period of the subject person.

7. The apparatus according to claim 2, wherein the characteristic quantity contains a first maximum heart rate for the first period of the subject person.

8. The apparatus according to claim 4, wherein the characteristic quantity contains a second maximum heart rate for the second period of the subject person.

9. The apparatus according to claim 2, wherein the characteristic quantity contains a speed till reaching a first maximum heart rate for the first period since start time of the first period with respect to the subject person.

10. The apparatus according to claim 2, wherein the characteristic quantity contains a speed till reaching an end of the first period since when reaching a first maximum heart rate for the first period with respect to the subject person.

11. The apparatus according to claim 4, wherein the characteristic quantity contains a speed till reaching a second maximum heart rate for the second period since start time of the second period with respect to the subject person.

12. The apparatus according to claim 4, wherein the characteristic quantity contains a speed till reaching an end of the second period since when reaching a second maximum heart rate for the second period with respect to the subject person.

13. The apparatus according to claim 2, wherein the characteristic quantity contains a period till reaching a first maximum heart rate for the first period since the start time of the first period with respect to the subject person.

14. The apparatus according to claim 2, wherein the characteristic quantity contains a period till a first maximum heart rate is restored to a predetermined heart rate at the speed till reaching the end time of the first period since when reaching the first maximum heart rate for the first period with respect to the subject person.

15. The apparatus according to claim 4, wherein the characteristic quantity contains a period till reaching a second maximum heart rate for the second period since the start time of the second period with respect to the subject person.

16. The apparatus according to claim 4, wherein the characteristic quantity contains a period till a second maximum heart rate is restored to a predetermined heart rate at the speed till reaching the end time of the second period since when reaching the second maximum heart rate for the second period with respect to the subject person.

17. A non-transitory computer-readable recording medium having stored therein a program for causing a computer to execute a process comprising:

acquiring characteristic quantity of variations of heart rate of a subject person related to a meal of the subject person generated from heart rate data of the subject person detected by a sensor and an identifier of the sensor, wherein the characteristic quantity is calculated from the heart rate data obtained for at least one of a first period and a second period, the first period containing a rise of heart rate of the subject person and the second period containing a rise of heart rate of the subject person immediately after the first period;

calculating a distribution range of history values of the characteristic quantity associated with a plurality of candidates;

extracting one of the plurality of candidates corresponding to the subject person from within the plurality of candidates, based on a relation between the generated characteristic quantity and the distribution range of the history values of the characteristic quantity; and determining whether an identifier of a sensor associated with the one of the plurality of candidates is coincident with the identifier of the sensor or not, and outputting an alert when the identifier of the sensor associated with the one of the plurality of candidates is not coincident with the identifier of the sensor.

18. A method for specifying a person, comprising:

acquiring characteristic quantity of variations of heart rate of a subject person related to a meal of the subject person generated from heart rate data of the subject person detected by a sensor and an identifier of the sensor, wherein the characteristic quantity is calculated from the heart rate data obtained for at least one of a first period and a second period, the first period containing a rise of heart rate of the subject person and the second period containing a rise of heart rate of the subject person immediately after the first period;

calculating a distribution range of history values of the characteristic quantity associated with a plurality of candidates;

extracting one of the plurality of candidates corresponding to the subject person from within the plurality of candidates, based on a relation between the generated characteristic quantity and the distribution range of the history values of the characteristic quantity; and determining whether an identifier of a sensor associated with the one of the plurality of candidates is coincident with the identifier of the sensor or not, and outputting an alert when the identifier of the sensor associated with the one of the plurality of candidates is not coincident with the identifier of the sensor.

* * * * *